United States Patent
Miller et al.

(10) Patent No.: US 10,857,203 B2
(45) Date of Patent: *Dec. 8, 2020

(54) METHODS AND COMPOSITIONS FOR TREATING HUNTINGTON'S DISEASE

(71) Applicant: Sangamo Therapeutics, Inc., Richmond, CA (US)

(72) Inventors: Jeffrey C. Miller, Richmond, CA (US); Edward J. Rebar, Richmond, CA (US); H. Steve Zhang, Richmond, CA (US)

(73) Assignee: Sangamo Therapeutics, Inc., Brisbane, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/587,428

(22) Filed: Sep. 30, 2019

(65) Prior Publication Data
US 2020/0030408 A1 Jan. 30, 2020

Related U.S. Application Data

(63) Continuation of application No. 16/291,708, filed on Mar. 4, 2019, now Pat. No. 10,471,123, which is a continuation of application No. 15/294,062, filed on Oct. 14, 2016, now Pat. No. 10,265,377, which is a continuation of application No. 14/446,189, filed on Jul. 29, 2014, now Pat. No. 9,499,597, which is a continuation of application No. 13/781,176, filed on Feb. 28, 2013, now Pat. No. 8,841,260.

(60) Provisional application No. 61/605,028, filed on Feb. 29, 2012.

(51) Int. Cl.
*A61K 38/17* (2006.01)
*C07K 14/47* (2006.01)
*C12N 15/90* (2006.01)

(52) U.S. Cl.
CPC ...... *A61K 38/1709* (2013.01); *C07K 14/4703* (2013.01); *C12N 15/907* (2013.01); *C07K 2319/00* (2013.01); *C07K 2319/70* (2013.01); *C07K 2319/71* (2013.01); *C07K 2319/81* (2013.01)

(58) Field of Classification Search
None
See application file for complete search history.

(56) References Cited

U.S. PATENT DOCUMENTS

| | | |
|---|---|---|
| 5,356,802 A | 10/1994 | Chandrasegaran |
| 5,436,150 A | 4/1995 | Chandrasegaran |
| 5,487,994 A | 1/1996 | Chandrasegaran |
| 5,789,538 A | 8/1998 | Pabo et al. |
| 5,925,523 A | 7/1999 | Dove et al. |
| 6,007,988 A | 12/1999 | Choo et al. |
| 6,013,453 A | 1/2000 | Choo et al. |
| 6,140,081 A | 10/2000 | Barbas |
| 6,140,466 A | 10/2000 | Carlos, III et al. |
| 6,200,759 B1 | 3/2001 | Dove et al. |
| 6,242,568 B1 | 6/2001 | Barbas et al. |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,503,717 B2 | 1/2003 | Case et al. |
| 6,534,261 B1 | 3/2003 | George, III et al. |
| 6,599,692 B1 | 7/2003 | Case et al. |
| 6,607,882 B1 | 8/2003 | George, III et al. |
| 6,689,558 B2 | 2/2004 | Case |
| 6,794,136 B1 | 9/2004 | Eisenberg et al. |
| 6,824,978 B1 | 11/2004 | George, III et al. |
| 6,903,185 B2 | 6/2005 | Kim et al. |
| 6,933,113 B2 | 8/2005 | Case et al. |
| 6,979,539 B2 | 12/2005 | Case et al. |
| 7,013,219 B2 | 3/2006 | Case et al. |
| 7,030,215 B2 | 4/2006 | Jamieson et al. |
| 7,067,317 B2 | 6/2006 | Rebar et al. |
| 7,070,934 B2 | 7/2006 | Case et al. |
| 7,153,949 B2 | 12/2006 | Kim et al. |
| 7,163,824 B2 | 1/2007 | Case et al. |
| 7,253,273 B2 | 8/2007 | Collingwood |
| 7,262,054 B2 | 8/2007 | Jamieson et al. |
| 7,361,635 B2 | 4/2008 | Collingwood et al. |
| 2003/0134350 A1 | 7/2003 | Takashi |
| 2003/0232410 A1 | 12/2003 | Aspland et al. |
| 2004/0002092 A1 | 1/2004 | Arnould et al. |
| 2005/0026157 A1 | 2/2005 | Baltimore et al. |

(Continued)

FOREIGN PATENT DOCUMENTS

| | | |
|---|---|---|
| EP | 2441774 A1 | 10/2003 |
| GB | 2338237 A | 8/1998 |

(Continued)

OTHER PUBLICATIONS

Alvarez, et al., "Development of ALN-TTR, An RNAI Therapeutic for the Treatment of Transthyretin-Mediated Amyloidosis," *Alnylam Pharmaceuticals and Medtronic*. University of Kentucky, KY (Jan. 19, 2010).

Beerli, et al., "Engineering Polydactyl Zinc-Finger Transcription Factors," *Nat. Biotechnol.* 20:135-141 (2002).

Bitinaite, et al., "FOKL Dimerization is Required for DNA Cleavage," *PNAS USA* 95:10570-10575 (1998).

Boch, et al., "Breaking the Code of DNA Binding Specificity of TAL-Type III Effectors," *Science* 326:1509-1512 (2009).

Bonas, et al., "Genetic and Structural Characterization of the Avirulence Gene AVRBS3 From Xanthomonas Campestris pv. Vesicatoria," *Mol. Gen. Genet.* 218:127-136 (1989).

(Continued)

Primary Examiner — Adam Weidner
(74) Attorney, Agent, or Firm — Pasternak Patent Law

(57) ABSTRACT

Disclosed herein are compositions comprising non-naturally occurring zinc finger domains, fusion proteins comprising these zinc finger domains, polynucleotides encoding these proteins, cells expressing these proteins and pharmaceutical compositions comprising these proteins or polynucleotides as well as methods of modifying an Htt gene using these compositions for treating or preventing Huntington's Disease.

7 Claims, 34 Drawing Sheets

Specification includes a Sequence Listing.

(56) References Cited

U.S. PATENT DOCUMENTS

| | | |
|---|---|---|
| 2005/0064474 A1 | 3/2005 | Holmes et al. |
| 2005/0208489 A1 | 9/2005 | Carroll et al. |
| 2006/0063231 A1 | 3/2006 | Li et al. |
| 2006/0078552 A1 | 4/2006 | Arnould et al. |
| 2006/0153826 A1 | 7/2006 | Arnould et al. |
| 2006/0188987 A1 | 8/2006 | Guschin et al. |
| 2006/0206949 A1 | 9/2006 | Arnould et al. |
| 2007/0060606 A1 | 3/2007 | Robertson et al. |
| 2007/0117128 A1 | 5/2007 | Hellinga et al. |
| 2007/0218528 A1 | 9/2007 | Miller |
| 2008/0015164 A1 | 1/2008 | Collingwood |
| 2008/0131962 A1 | 6/2008 | Miller |
| 2008/0159996 A1 | 7/2008 | Ando et al. |
| 2009/0068164 A1 | 3/2009 | Barbas et al. |
| 2010/0003756 A1 | 1/2010 | Collingwood et al. |
| 2010/0299768 A1 | 11/2010 | Perrin et al. |
| 2011/0082093 A1 | 4/2011 | Gregory et al. |
| 2011/0201055 A1 | 8/2011 | Doyon et al. |
| 2011/0301073 A1 | 12/2011 | Gregory et al. |

FOREIGN PATENT DOCUMENTS

| | | |
|---|---|---|
| WO | WO 1995/19431 A1 | 7/1995 |
| WO | WO 1996/06166 A1 | 2/1996 |
| WO | WO 1998/37186 A1 | 8/1998 |
| WO | WO 1998/53057 A1 | 11/1998 |
| WO | WO 1998/53058 A1 | 11/1998 |
| WO | WO 1998/53059 A1 | 11/1998 |
| WO | WO 1998/53060 A1 | 11/1998 |
| WO | WO 1998/54311 A1 | 12/1998 |
| WO | WO 2000/27878 A1 | 5/2000 |
| WO | WO 2001/60970 A2 | 8/2001 |
| WO | WO 2001/88197 A2 | 11/2001 |
| WO | WO 2002/016536 A1 | 2/2002 |
| WO | WO 2002/077227 A2 | 10/2002 |
| WO | WO 2002/099084 A2 | 12/2002 |
| WO | WO 2005/068633 A1 | 7/2005 |
| WO | WO 2006/094106 A2 | 9/2006 |
| WO | WO 2007/014275 A2 | 2/2007 |
| WO | WO 2003/016496 A2 | 2/2008 |
| WO | WO 2009007855 A2 | 1/2009 |
| WO | WO 2009/042163 A2 | 4/2009 |
| WO | WO 2010/079430 A1 | 7/2010 |
| WO | WO 2011/016840 A1 | 2/2011 |
| WO | WO 2011/146121 A1 | 11/2011 |
| WO | WO 2013/130824 A1 | 9/2013 |

OTHER PUBLICATIONS

Butler, et al., "Lipophilic Sirna Delivery by Reconstituted Lipoprotein Particles in Vivo," *Alnylam Pharmaceuticals and Medtronic.* University of Kentucky, KY (Jan. 19, 2010).

Cha, et al., "Altered Brain Neurotransmitter Receptors in Transgenic Mice Expressing a Portion of an Abnormal Human Huntington Disease Gene," *Proc. Natl. Acad. Sci.* 95:6480-6485 (1998).

Chandwani, et al., "Induction of DARP-32 by Brain-Derived Neurothrophic Factor in Striatal Neurons in Vitro is Modified by Histone Deacetylase Inhibitors and NAB2," *PLOS ONE* 8(10):epage76842 (2013).

Choo, et al., "Advances in Zinc Finger Engineering," *Curr. Opin. Struct. Biol.* 10:411-416 (2000).

Christian, et al., "TAL Effector Nucleases Create Targeted DNA Double-Strand Breaks," *Genetics* epub 10.1534/genetics.110.120717 (2010).

Davies and Rubinsztein, "Polyalanine and Polyserine Frameshift Products in Huntington's Disease," *Journal of Medical Genetics* 43:893-896 (2006).

Elbashir, et al., "Comprehensive Evaluation of Canonical vs. Dicer-Substrate Sirnas in Vitro and in Vivo,"*Alnylam Pharmaceuticals and Medtronic.* University of Kentucky, KY (Jan. 19, 2010).

Garriga-Canut, et al., "Synthetic Zinc Finger Repressors Reduce Mutant Huntingtin Expression in the Brain of R6/2 Mice," *PNAS* 109(45):E3136-E3145 (2012).

Ghosh and Regan, "Antiparallel Leucine Zipper-Directed Protein Reassembly: Application to the Green Fluorescent Protein," *J. Am. Chem. Soc.* 122:5658-5659 (2000).

Gisecke, et al., "Synthetic Protein-Protein Interaction Domains Created by Shuffling CYS2HIS2 Zinc-Fingers," *Mol. Sys. Biol.* 2:2006-2011 (2006).

Graham, et al., "Cleavage at the Caspase-6 Site is Required for Neuronal Dysfunction and Degeneration Due to Mutant Huntingtin," *Cell* 125:1179-1191 (2006).

Hebb, et al., "Striatal Phosphodiesterase MRNA and Protein Levels are Reduced in Huntington's Disease Transgenic Mice Prior to the Onset of Motor Symptoms," *Neuroscience* 123:967-981 (2004).

Heuer, et al., "Repeat Domain Diversity of AVRBS3-Like Genes in Ralstonia Solanacearum Strains and Association With Host Preferences in the Field," *Appl. and Enviro. Micro.* 73(13):4379-4384 (2007).

Isalan, et al., "A Rapid, Generally Applicable Method to Engineer Zinc Fingers Illustrated by Targeting the HIV-1 Promoter," *Nat. Biotechnol.* 19:656-660 (2001).

Jinek, et al., "RNA-Programmed Genome Editing in Human Cells," *eLife* 2:e00471 (2013).

Jinek, et al., "A Programmable Dual-RNA—Guided DNA Endonuclease in Adaptive Bacterial Immunity," *Science* 337:816-821 (2012).

Kay, et al., "A Bacterial Effector Acts as a Plant Transcription Factor and Induces a Cell Size Regulator," *Science* 318:648-651 (2007).

Kells, et al., "AAV-Mediated Gene Delivery of BDNF or GDNF is Neuroprotective in a Model of Huntington Disease," *Molecular Therapy* 9(5):682-688 (2004).

Kim, et al., "Insertion and Deletion Mutants of FOKI Restriction Endonuclease," *J. Biol. Chem.* 269:31978-31982 (1994b).

Kim et al., "Chimeric Restriction Endonuclease," *PNAS USA* 91:883-887 (1994a).

Li et al., "Functional Domains in FOKI Restriction Endonuclease," *PNAS USA* 89:4275-4279 (1992).

Li, et al., "Alteration of the Cleavage Distance of FOKI Restriction Endonuclease by Insertion Mutagenesis," *PNAS USA* 90:2764-2768 (1993).

McClain, et al., "Design and Characterization of a Heterodimeric Coiled Coil That Forms Exclusively With an Antiparallel Relative Helix Orientation," *J. Am. Chem. Soc.* 123:3151-3152 (2001).

Menalled, et al., "Time Course of Early Motor and Neuropathological Anomalies in a Knock-In Mouse Model of Huntington's Disease With 140 CAG Repeats," *J. Comp. Neurol.* 465(1):11-26 (2003).

Mittelman et al., "Zinc-Finger Directed Double-Strand Breaks Within CAG Repeat Tracts Promote Repeat Instability in Human Cells," *PNAS USA* 106(24):9607-9612 (2009).

Moscou and Bogdanov, "A Simple Cipher Governs DNA Recognition by TAL Effectors," *Science* 326:1501 (2009).

Pabo, et al., "Design and Selection of Novel CYS2HIS2 Zinc Finger Proteins" *Ann. Rev. Biochem.* 7:313-340 (2001).

Papworth, et al., "Designer Zinc-Finger Proteins and Their Applications," *Gene* 356(1): 27-38 (2006).

Perez et al., "Establishment of HIV-1 Resistance in CD4+ T Cells by Genome Editing Using Zinc-Finger Nucleases," *Nat. Biotechno.* 26(7):808-816 (2008).

Prospero and Fischbeck, "Therapeutics Development for Triplet Repeat Expansion Diseases," *Nat. Rev. Gen.* 6:756-765 (2005).

Rajeev, et al., "Carbohydrate Conjunction to SIRNA for Tissue and Cell Specific Delivery," *Alnylam Pharmaceuticals and Medtronic.* University of Kentucky, KY (Jan. 19, 2010).

Sah, et al., "Developing RNAI Therapeutics Targeting Huntington With Direct CNS Delivery,"*Alnylam Pharmaceuticals and Medtronic.* University of Kentucky, KY (Jan. 19, 2010).

Schornak, et al., "Gene-For-Gene-Mediated Recognition of Nuclear-Targeted AVRBS3-Like Bacterial Effector Proteins," *J. Plant Physiol.* 163(3):256-272 (2006).

Segal, et al., "Custom DNA-Binding Proteins Come of Age: Polydactyl Zinc-Finger Proteins," *Curr. Opin. Biotechnol.* 12:632-637 (2001).

Segal, "Bacteria Herald a New Era of Gene Editing," *eLife* 2:e00563 (2013).

Tan, et al., "Zinc-Finger Protein-Targeted Gene Regulation: Genomewide Single-Gene Specificity," *Proceedings of the National Academy of Sciences* 100(21):11997-12002 (2003).

(56) References Cited

OTHER PUBLICATIONS

Urnov, et al., "Highly Efficient Endogenous Human Gene Correction Using Designed Zinc-Finger Nucleases," *Nature* 435(7042):646-651 (2005).
Walker, "Huntington's Disease ," *Lancet* 369:218-228 (2007).
Wheeler, et al., "Length-Dependent Gametic CAG Repeat Instability in the Huntington's Disease Knock-In Mouse," *Hum. Mol. Genet.* 8:115-122 (1999).
Zuccato, et al., "Progressive Loss of BDNF in a Mouse Model of Huntington's Disease and Rescue by BDNF Delivery," *Pharmacological Research* 52(2):133-139 (2005).
Ahmad, et al., "Human Brain Pet Imaging of PDE10A in Parkinson's and Huntington's Disease," Eur. J. Nucl. Med. Mol. Imaging, vol. 40(Suppl. 2):S143; OP613 (2013).
Ehrlich, Michelle E., "Huntington's Disease and the Striatal Medium Spiny Neuron: Cell-Autonomous and Non-Cell-Autonomous Mechanisms of Disease," Neurotherapeutics, vol. 9, pp. 270-287 (2012).
Kim, et al., "Selective Ablation of D1 Receptor-Expressing Neurons in the Striatum Is Associated With Parkinsonism But Not Dystonia," J. Neurochem., vol. 110 (Suppl.2):259; FR10-19 (2009).

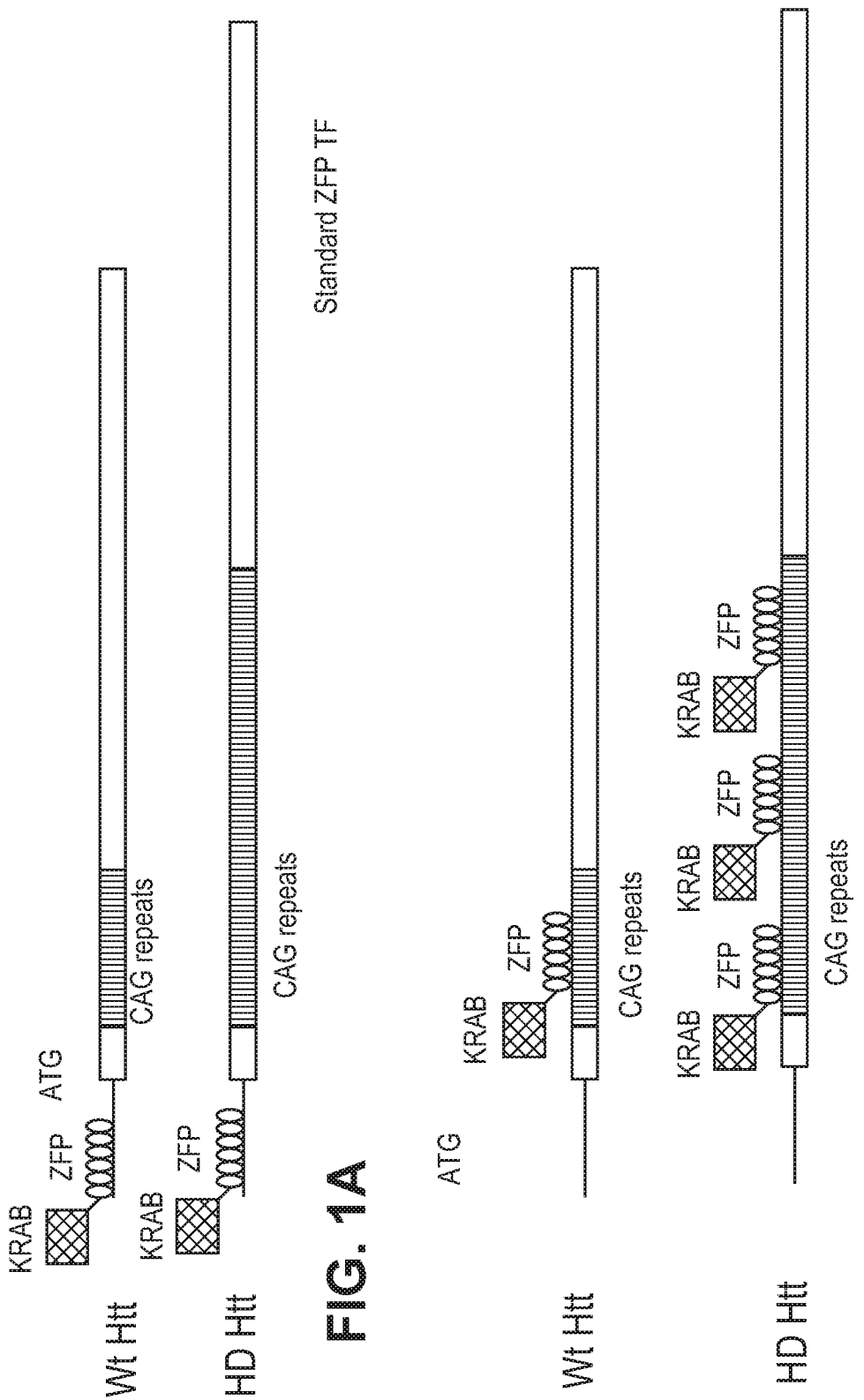

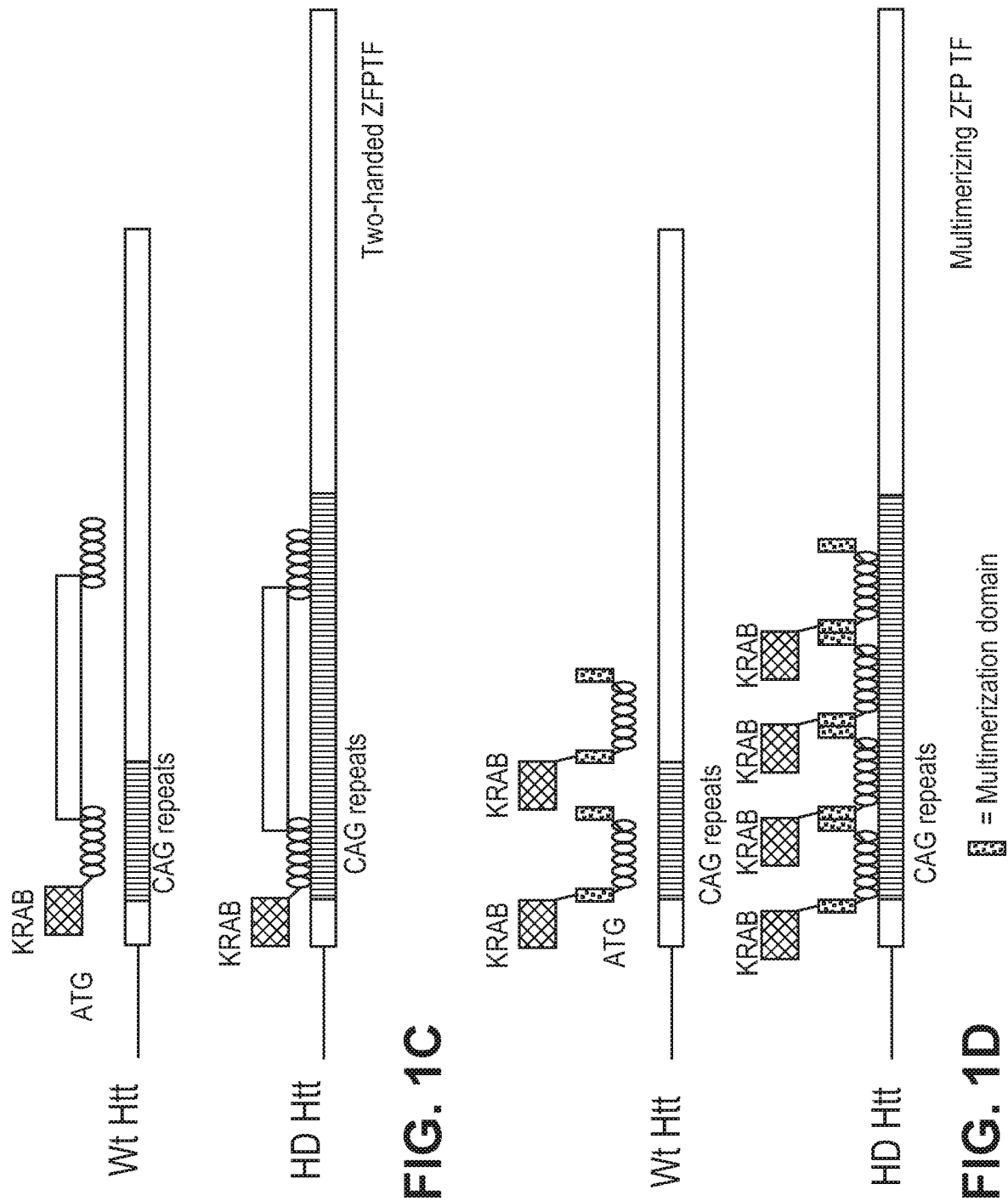

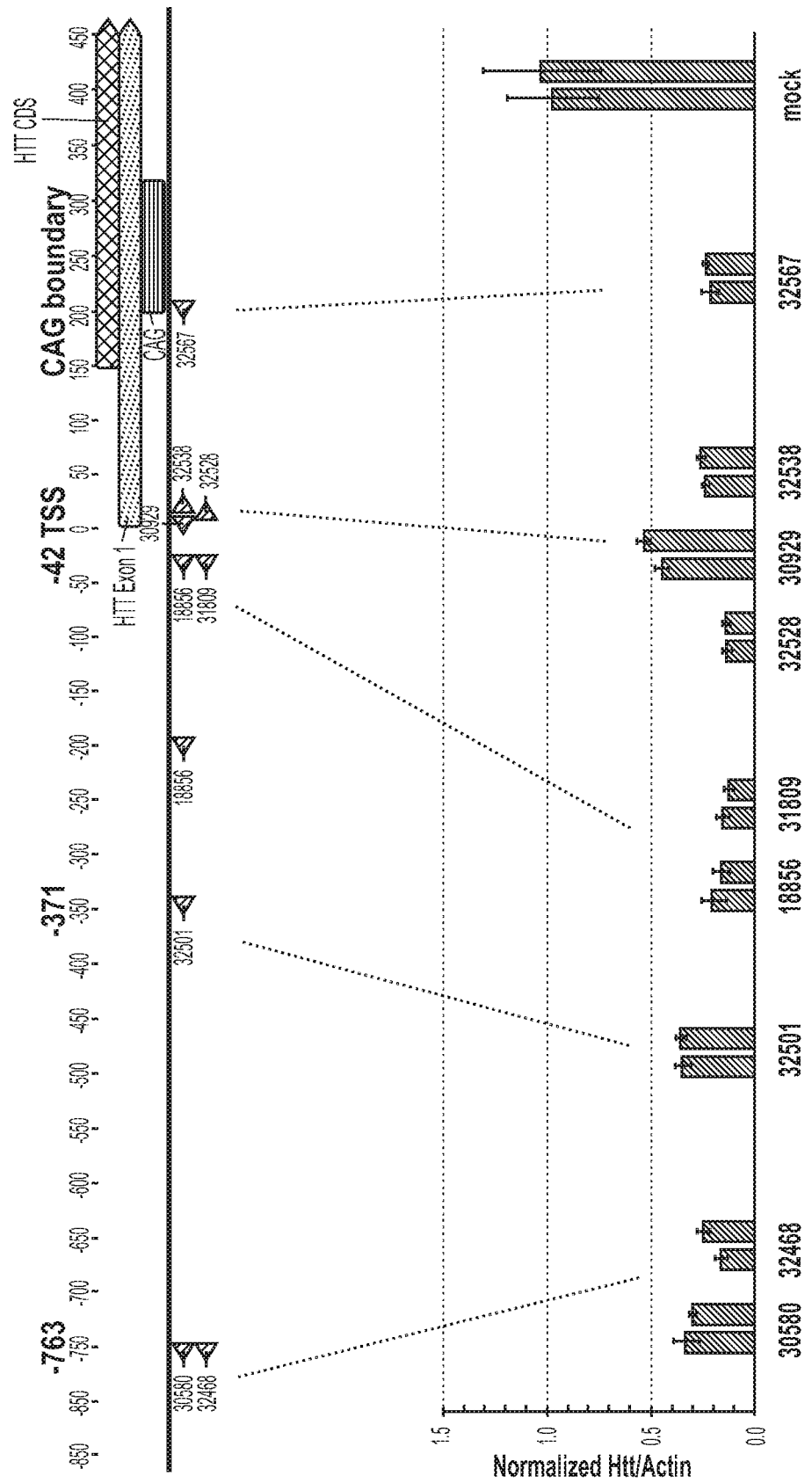

FIG. 2B
1:3 dilution of lysate
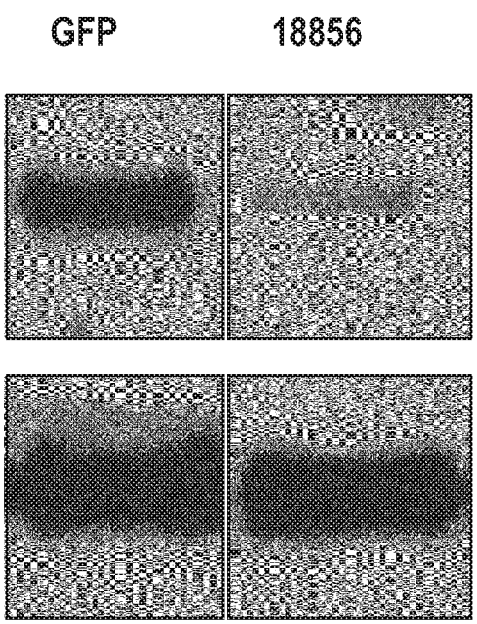
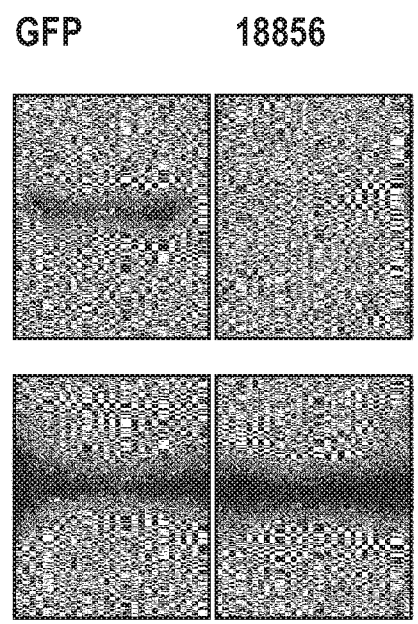
GFP  18856    GFP  18856
Htt
P65

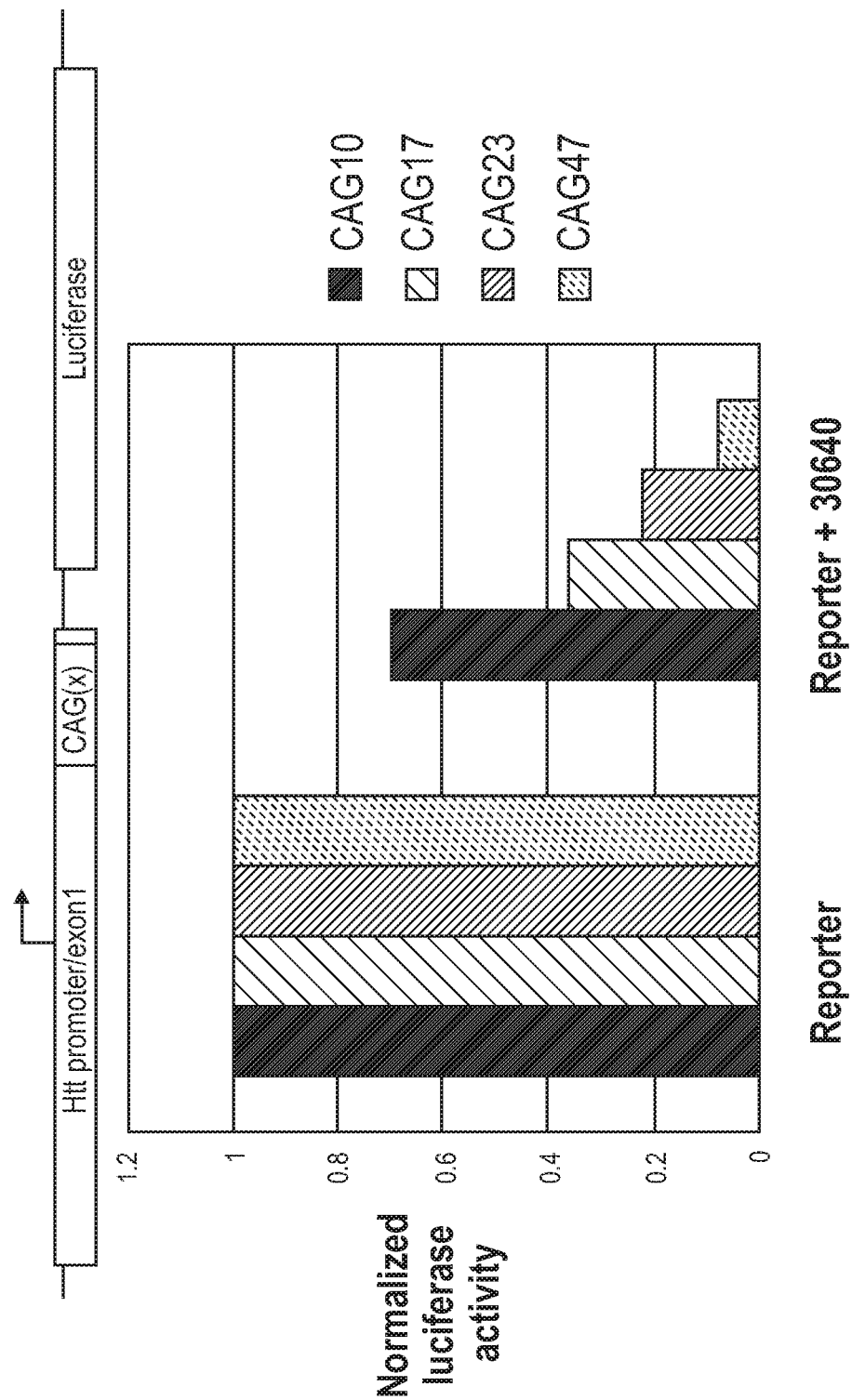

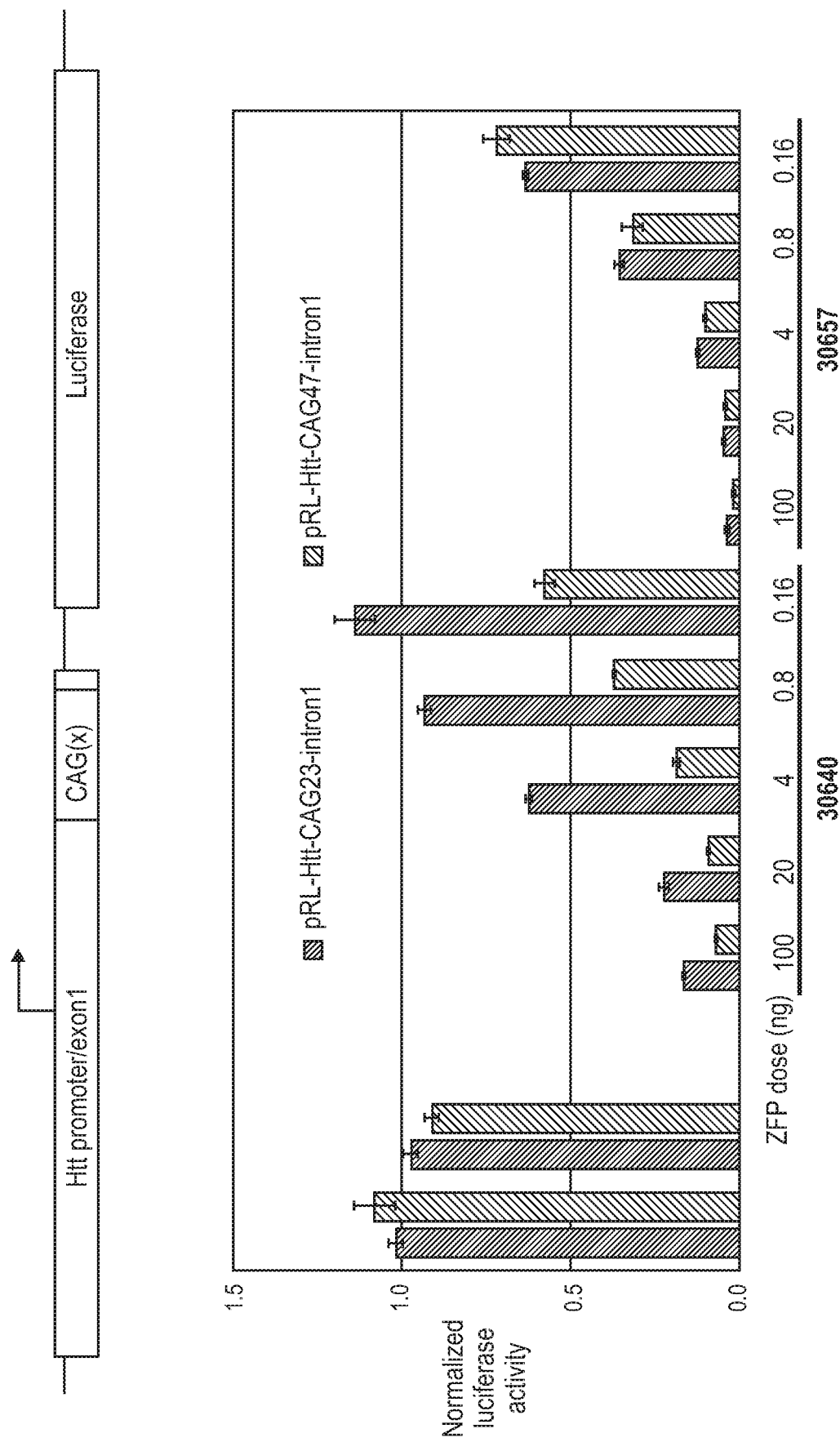

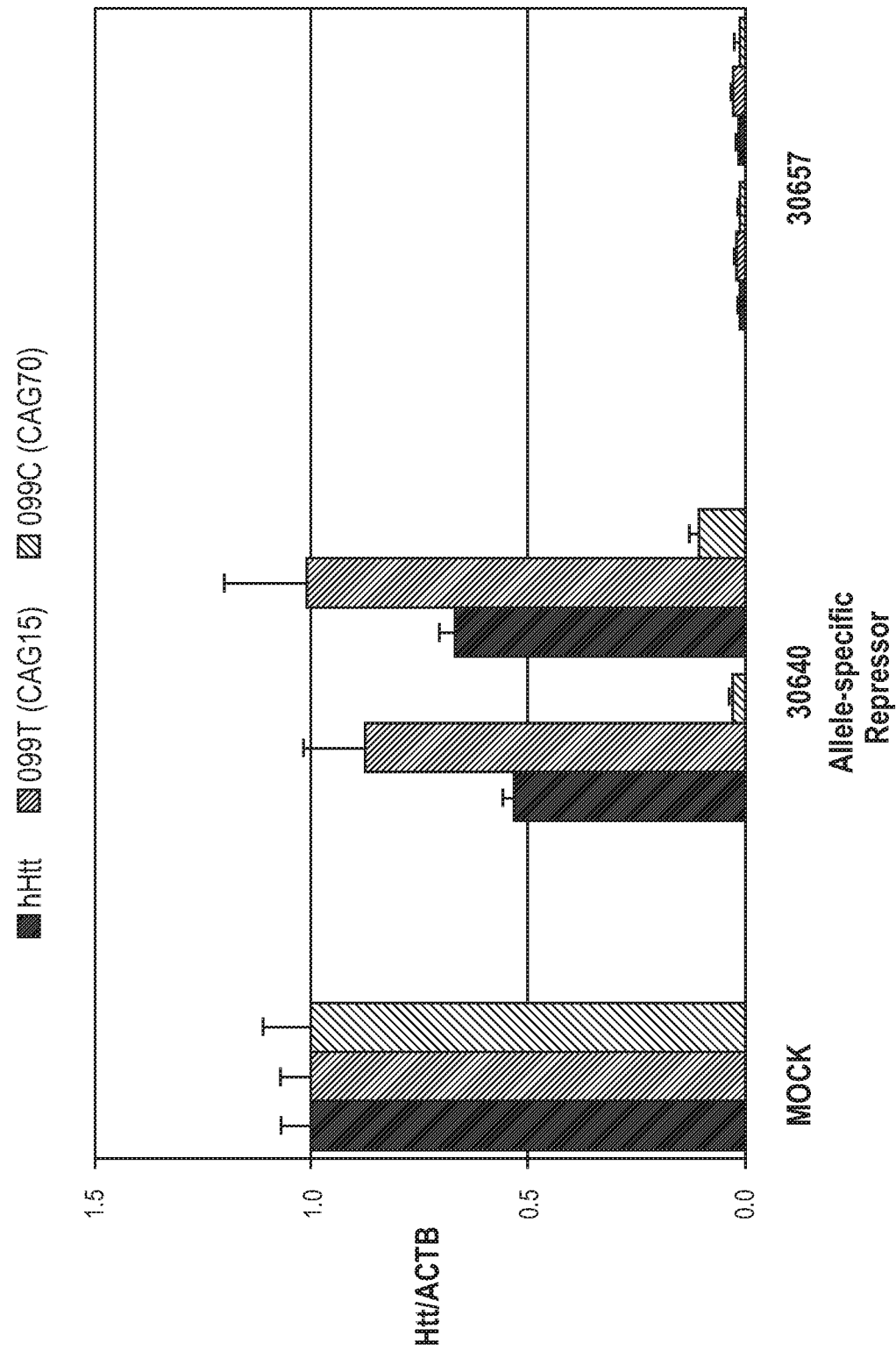

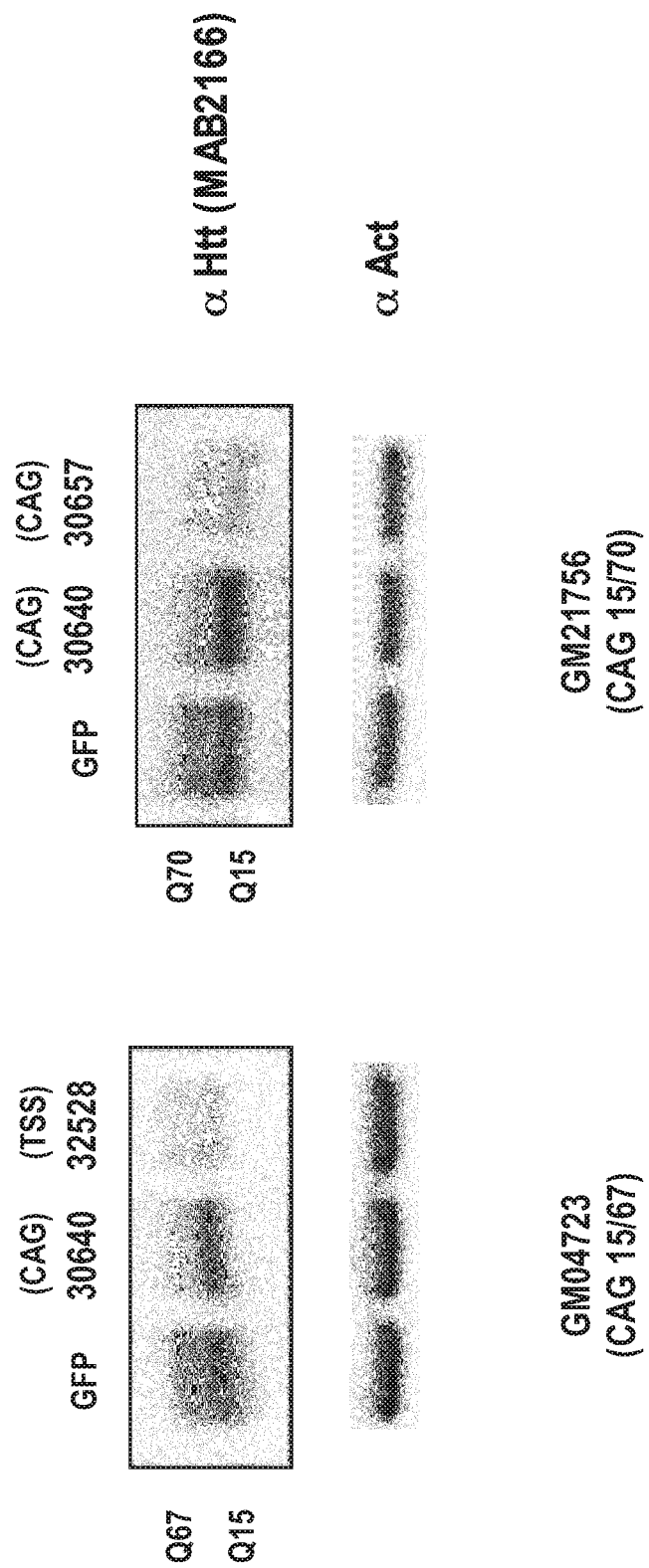

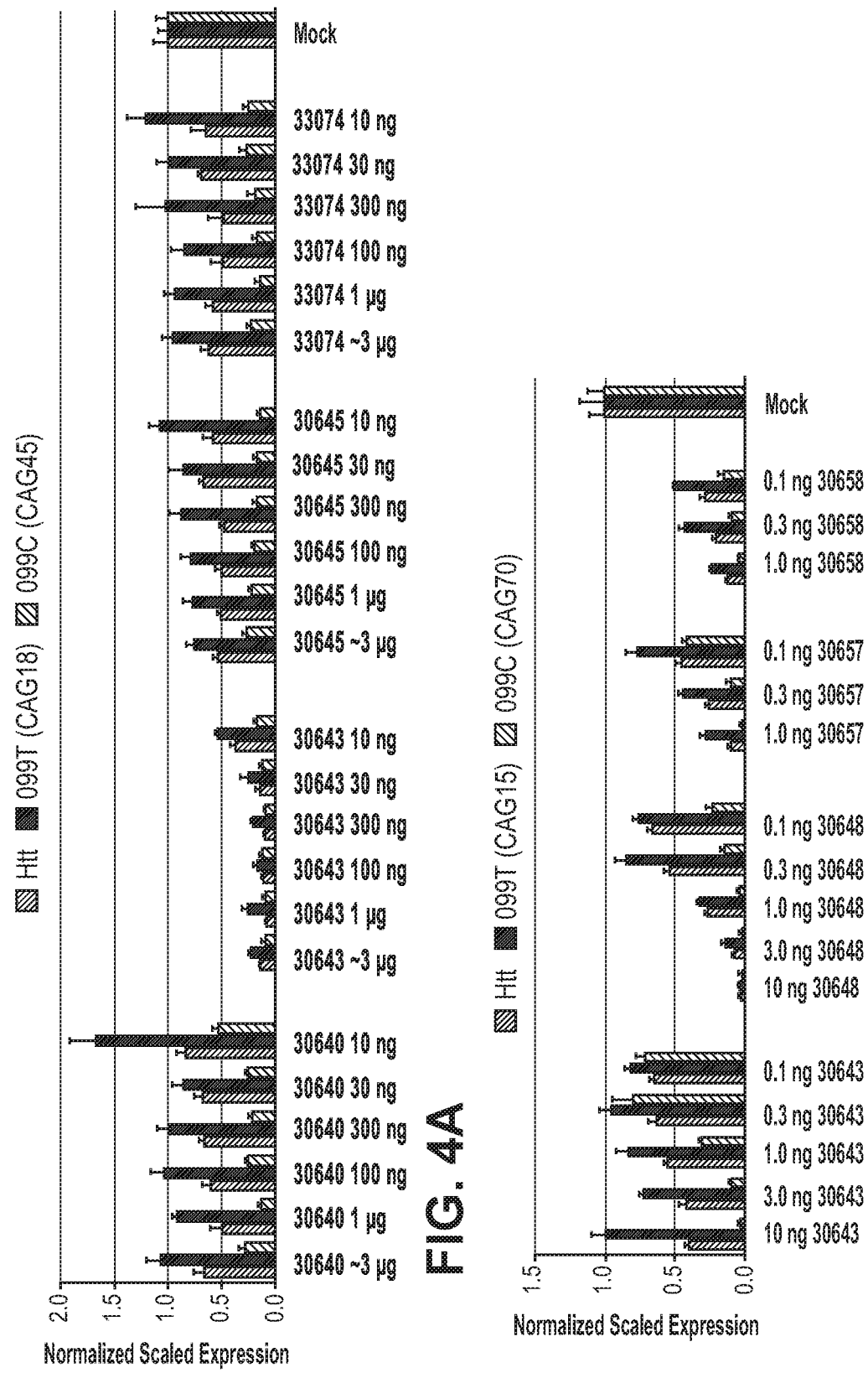

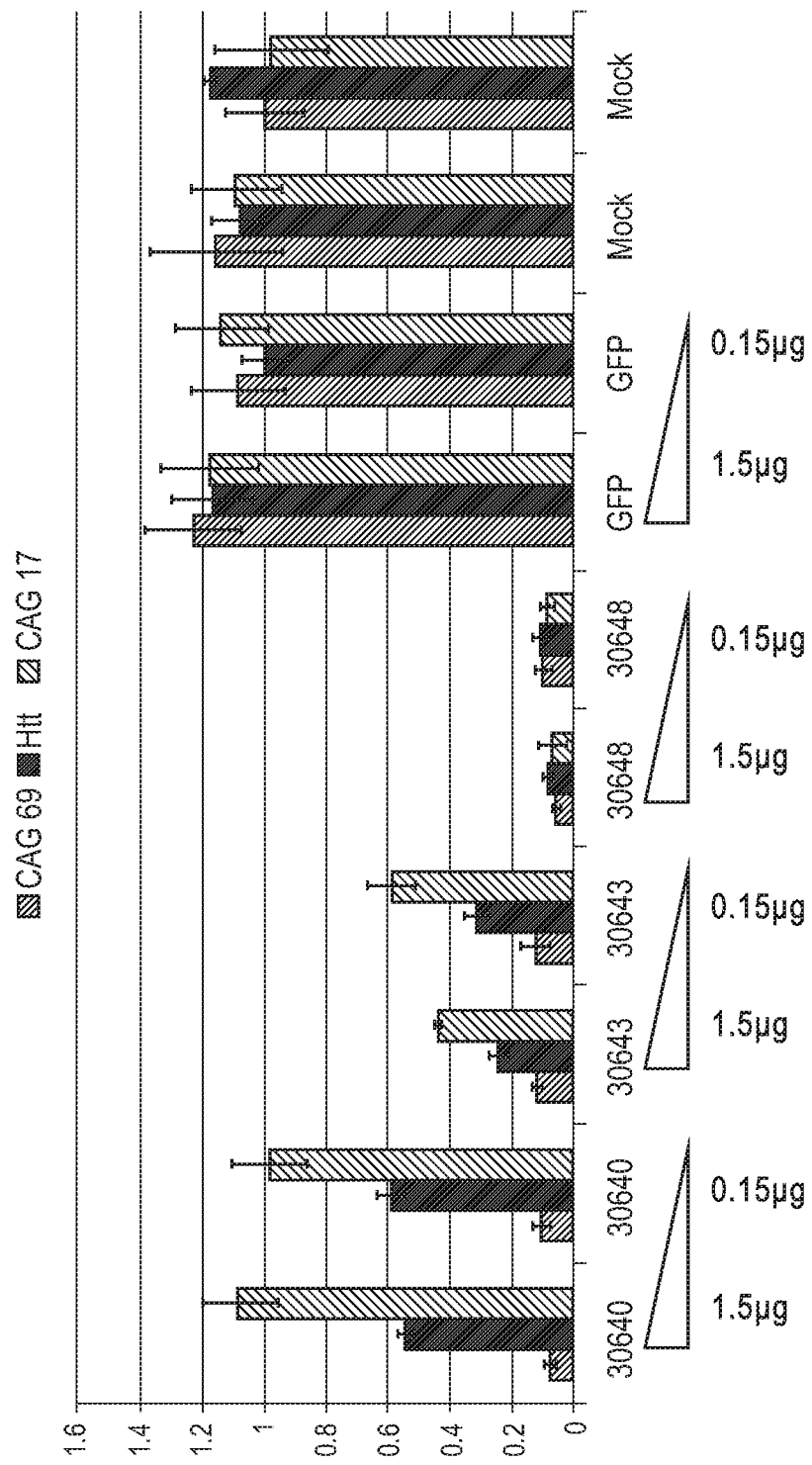

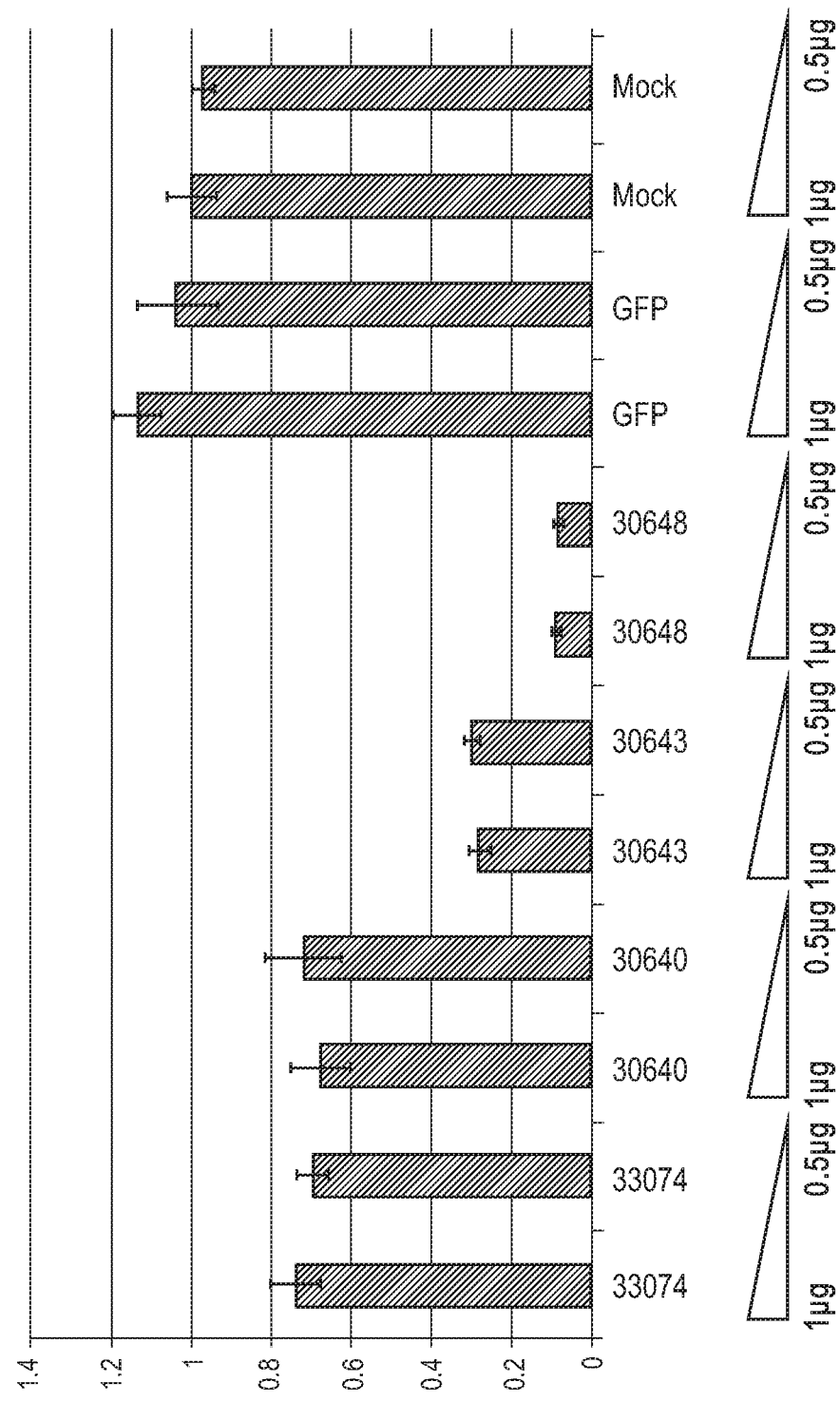

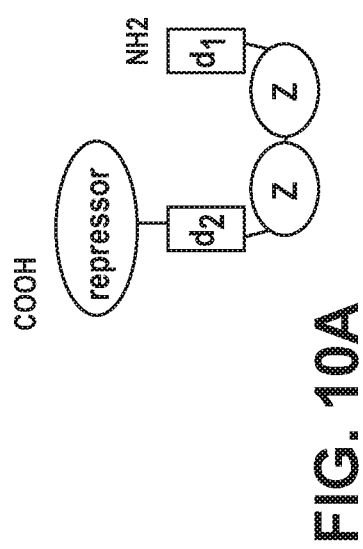
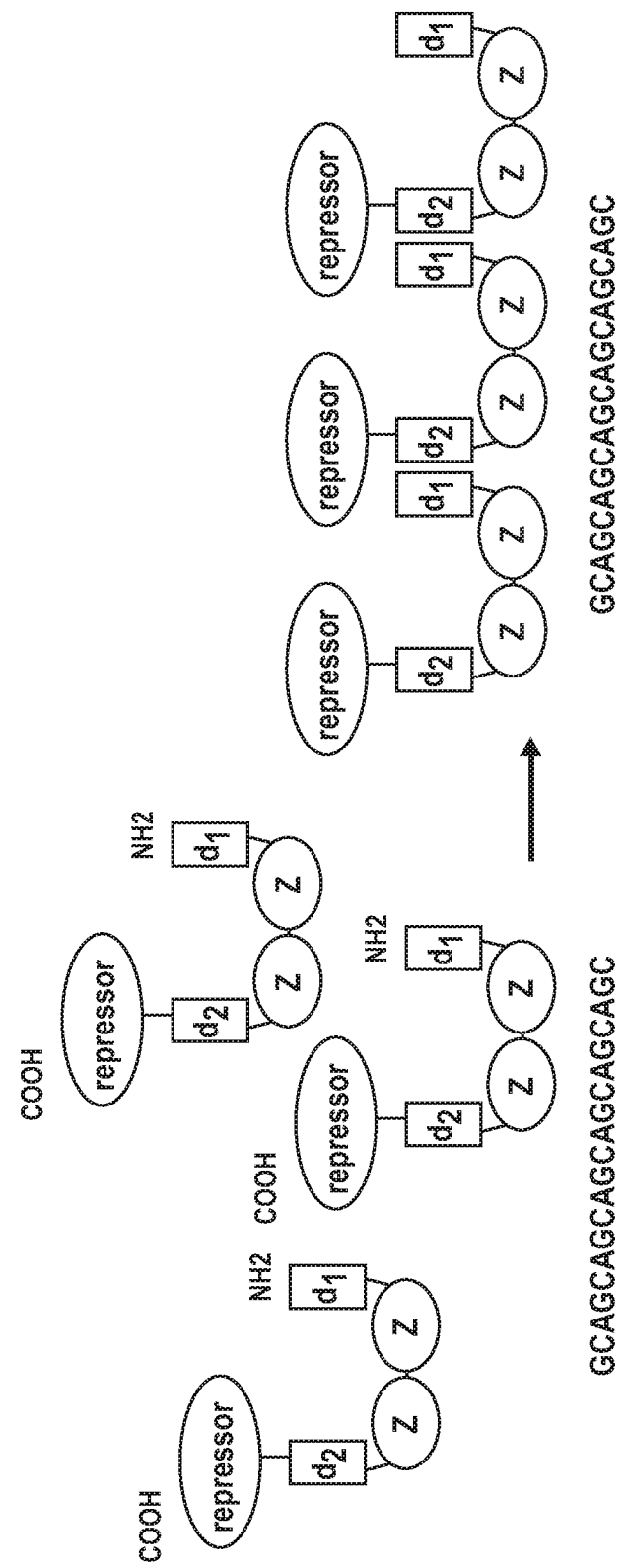
FIG. 10A
FIG. 10B

*MAPKKKRKVGIHGVLRGAATKCVHCGIVFLDEVMYALHMSCHGFRDPFECNICGYHSQDRYEFSSHIVRGEHSGVP*[ZFP] GSGGTKCVHCGIVFLDEVMYALHMSCHGFRDPFECNICGYHSQDRYEFSSHIVRGEHLRQKDAARSRSGMDAKSLTAWSRT LVTFKDVFVDFTREEWKLLDTAQQIVYRNVMLENYKNLVSLGYQLTKPDSETAFEIKSSVDYKDDDDK

DZ#2:

*MAPKKKRKVGIHGVLRGAAFKCEHCRILFLDHVMFTIHMGCHGFRDPFKCNMCGEKCDGPVGLFVHMARNAHSGVP*[ZFP] GSGGTKCVHCGIVFLDEVMYALHMSCHGFRDPFECNICGYHSQDRYEFSSHIVRGEHLRQKDAARSRSGMDAKSLTAWSRT LVTFKDVFVDFTREEWKLLDTAQQIVYRNVMLENYKNLVSLGYQLTKPDVILRLEKGEEPWLVEREIHQETHPDSETAFEIKSSVDYKDDDDK

DZ#3:

*MAPKKKRKVGIHGVLRGAAFKCEHCRILFLDHVMFTIHMGCHGFRDPFKCNMCGEKCDGPVGLFVHMARNAHSGVP*[ZFP] GSGGHHCQHCDMYFADNILYTIHMGCHGYENPFECNICGYHSQDRYEFSSHIVRGEHLRQKDAARSRSGMDAKSLTAWSRTLVTFKDVFVDF TREEWKLLDTAQQIVYRNVMLENYKNLVSLGYQLTKPDVILRLEKGEEPWLVEREIHQETHPDSETAFEIKSSVDYKDDDDK

DZ#4:

*MAPKKKRKVGIHGVLRGAAHHCQHCDMYFADNILYTIHMGCHSCDDVFKCNMCGEKCDGPVFKCNMCGEKCDGPVGLFVHMARNAHGEKPTKCVHCGIVFLD* EVMYALHMSCHGFRDPFECNICGYHSQDRYEFSSHIVRGEHSGVP[ZFP]GSGGFKCEHCRILFLDHVMFTIHMGCHGFRDPFKCNMC GEKCDGPVGLFVHMARNAHGEKPFYCEHCEITFRDVMYSLHKGYHGFRDPFECNICGYHSQDRYEFSSHIVRGEHLRQKDAARSRSGM DAKSLTAWSRTLVTFKDVFVDFTREEWKLLDTAQQIVYRNVMLENYKNLVSLGYQLTKPDVILRLEKGEEPWLVEREIHQETHPDSETAF EIKSSVDYKDDDDK

*MAPKKKRKVGIHG*VLRGAAGGAQLEKELQALEWENQALEKELAQLKWKLQALK
KKLAQGGLRQKDAARSRSGMDAKSLTAWSRTLVTFKDVFVDFTREEWKLLDTAQQIVYRNVMLENYKNLVSLGYQLTKPDVILRLEKGEEP
WLVEREIHQETHPDSETAFEIKSSVDYKDDDDK

CC#2:

*MAPKKKRKVGIHG*VLRGAAGGEQLEKKLQALEKKLQANKKELAQLKWELQALKKK
ELAQGGLRQKDAARSRSGMDAKSLTAWSRTLVTFKDVFVDFTREEWKLLDTAQQIVYRNVMLENYKNLVSLGYQLTKPDVILRLEKGEEPW
LVEREIHQETHPDSETAFEIKSSVDYKDDDDK

CC#3:

*MAPKKKRKVGIHG*VLRGAAGGEQLEKKLAQLEWKNQALEKKLAQGGSGVP[ZFP]GSGGELQANKKELAQLKWELQALKKELAQGGL
RQKDAARSRSGMDAKSLTAWSRTLVTFKDVFVDFTREEWKLLDTAQQIVYRNVMLENYKNLVSLGYQLTKPDVILRLEKGEEPWLVEREI
HQETHPDSETAFEIKSSVDYKDDDDK

CC#4:

*MAPKKKRKVGIHG*VLRGAAGGEQLEKKLAQLEWKNQAGGSGVP[ZFP]GSGGQANKKELAQLKWELQALKKELAQGGLRQKD
AARSRSGMDAKSLTAWSRTLVTFKDVFVDFTREEWKLLDTAQQIVYRNVMLENYKNLVSLGYQLTKPDVILRLEKGEEPWLVEREIHQE
THPDSETAFEIKSSVDYKDDDDK.

FIG. 10D (CONT.)

CC2-ZFP-KOX:
*MAPKKKRKVGIHGVLAAGGEQLEKKLQALEKKLAQLEWKNQALEKKLAQGSGGVP[ZFP]GSGGALKKELQANKKELAQLKWELQALKKELAQGS
GMDAKSLTAWSRTLVTFKDVFVDFTREEWKLLDTAQQIVYRNVMLENYKNLVSLGYQLTKPDVILRLEKGEEPWLVEREIHQETHPDSETAFEI
KSSVDYKDDDDK*

CC5-ZFP-KOX:
*MAPKKKRKVGIHGVLAAGGEQLEKKLQALEKKLAQLEWKNQALEKKLAQGVP[ZFP]GSGGALKKELQANKKELAQLKWELQALKKELAQGS
GMDAKSLTAWSRTLVTFKDVFVDFTREEWKLLDTAQQIVYRNVMLENYKNLVSLGYQLTKPDVILRLEKGEEPWLVEREIHQETHPDSETAF
EIKSSVDYKDDDDK*

CC6-ZFP-KOX:
*MAPKKKRKVGIHGVLAAGGEQLEKKLQALEKKLAQLEWKNQALEKKLAQGGSGVP[ZFP]GSALKKELQANKKELAQLKWELQALKKELAQGS
GMDAKSLTAWSRTLVTFKDVFVDFTREEWKLLDTAQQIVYRNVMLENYKNLVSLGYQLTKPDVILRLEKGEEPWLVEREIHQETHPDSETAF
EIKSSVDYKDDDDK*

CC7-ZFP-KOX:
*MAPKKKRKVGIHGVLAAGGEQLEKKLQALEKKLAQLEWKNQALEKKLAQGVP[ZFP]GSALKKELQANKKELAQLKWELQALKKELAQGS
GMDAKSLTAWSRTLVTFKDVFVDFTREEWKLLDTAQQIVYRNVMLENYKNLVSLGYQLTKPDVILRLEKGEEPWLVEREIHQETHPDSETA
FEIKSSVDYKDDDDK*

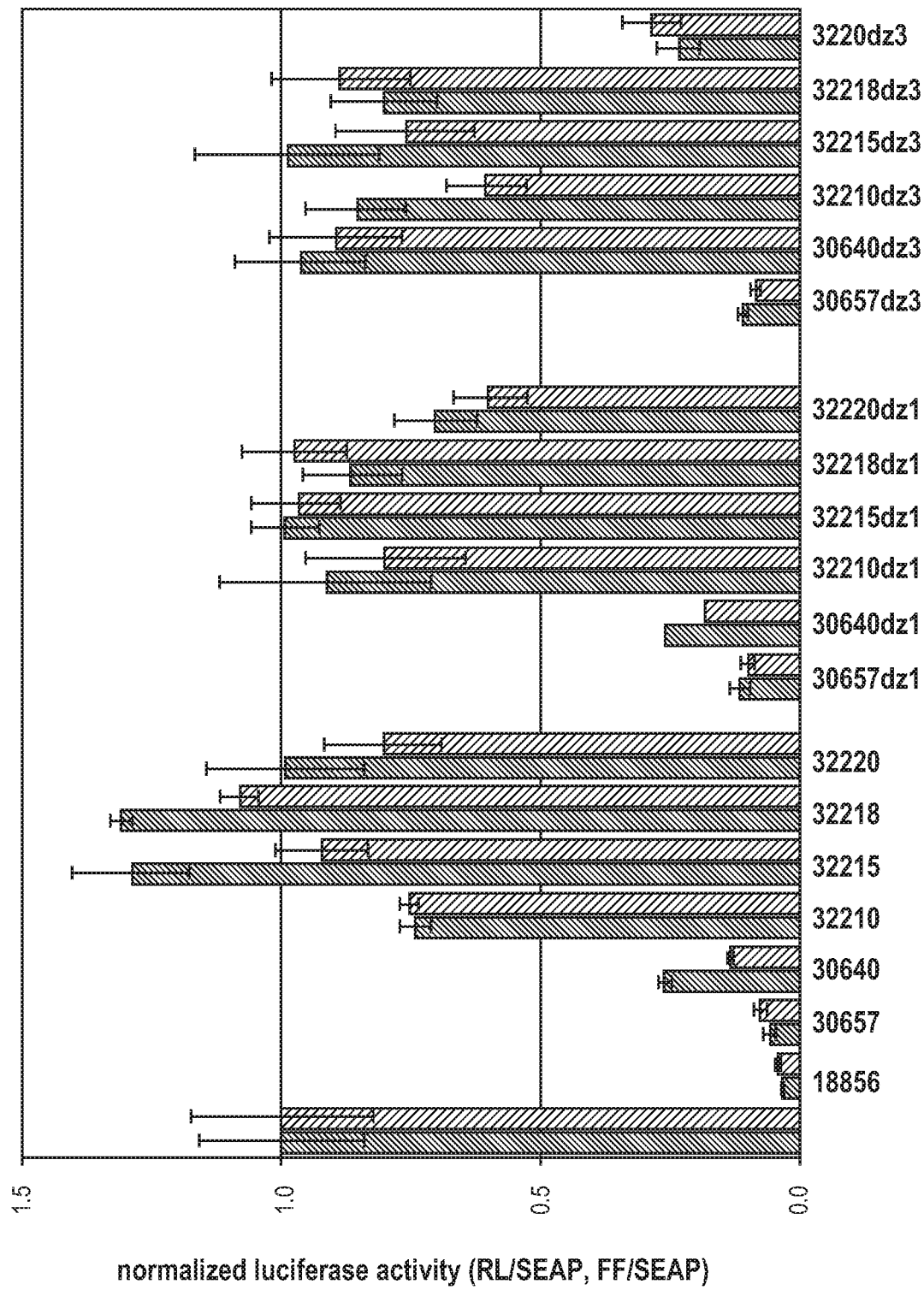

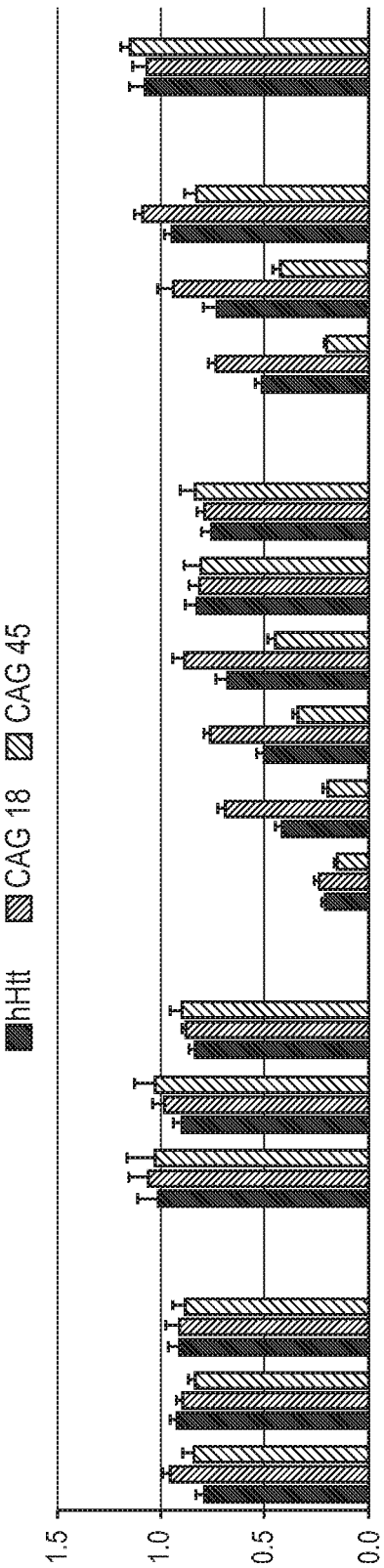
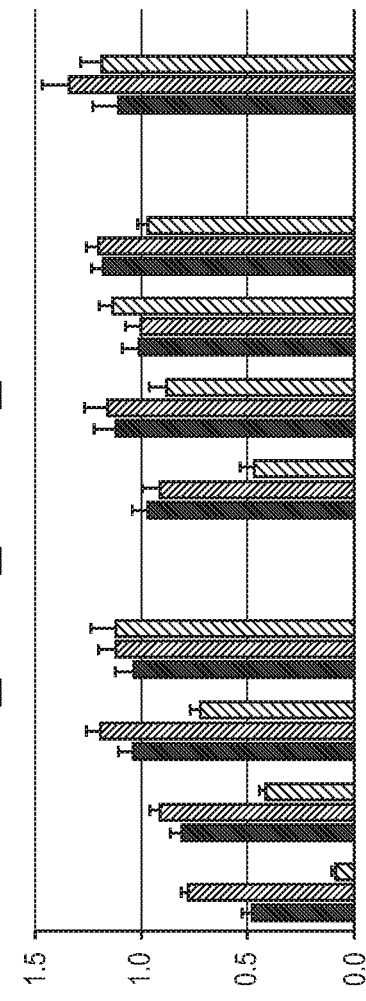
FIG. 12A
FIG. 12B a: 29627/29628
b: 29631/29632
c: 29637/29638 d: 25917/25916
e: 25921/25920
f: 25923/25922

METHODS AND COMPOSITIONS FOR TREATING HUNTINGTON'S DISEASE

CROSS-REFERENCE TO RELATED APPLICATIONS

The present application is a continuation of U.S. patent application Ser. No. 16/291,708, filed Mar. 4, 2019, which is a continuation of U.S. patent application Ser. No. 15/294,062, filed Oct. 14, 2016, now U.S. Pat. No. 10,265,377, which is a continuation of U.S. patent application Ser. No. 14/446,189, filed Jul. 29, 2014, now U.S. Pat. No. 9,499,597, which is a continuation of U.S. patent application Ser. No. 13/781,176, filed Feb. 28, 2013, now U.S. Pat. No. 8,841,260, which claims the benefit of U.S. Provisional Patent Application No. 61/605,028, filed Feb. 29, 2012, the disclosures of which are hereby incorporated by reference in their entireties.

SEQUENCE LISTING

The instant application contains a Sequence Listing which has been submitted in ASCII format via EFS-Web and is hereby incorporated by reference in its entirety.

TECHNICAL FIELD

The present disclosure is in the fields of gene expression and genome editing.

BACKGROUND

Huntington's Disease (HD), also known as Huntington's Chorea, is a progressive disorder of motor, cognitive and psychiatric disturbances. The mean age of onset for this disease is age 35-44 years, although in about 10% of cases, onset occurs prior to age 21, and the average lifespan post-diagnosis of the disease is 15-18 years. Prevalence is about 3 to 7 among 100,000 people of western European descent.

Huntington's Disease is an example of a trinucleotide repeat expansion disorders were first characterized in the early 1990s (see Di Prospero and Fischbeck (2005) *Nature Reviews Genetics* 6:756-765). These disorders involve the localized expansion of unstable repeats of sets of three nucleotides and can result in loss of function of the gene in which the expanded repeat resides, a gain of toxic function, or both. Trinucleotide repeats can be located in any part of the gene, including non-coding and coding gene regions. Repeats located within the coding regions typically involve either a repeated glutamine encoding triplet (CAG) or an alanine encoding triplet (CGA). Expanded repeat regions within non-coding sequences can lead to aberrant expression of the gene while expanded repeats within coding regions (also known as codon reiteration disorders) may cause mis-folding and protein aggregation. The exact cause of the pathophysiology associated with the aberrant proteins is often not known. Typically, in the wild-type genes that are subject to trinucleotide expansion, these regions contain a variable number of repeat sequences in the normal population, but in the afflicted populations, the number of repeats can increase from a doubling to a log order increase in the number of repeats. In HD, repeats are inserted within the N terminal coding region of the large cytosolic protein Huntingtin (Htt). Normal Htt alleles contain 15-20 CAG repeats (SEQ ID NO: 226), while alleles containing 35 or more repeats (SEQ ID NO: 227) can be considered potentially HD causing alleles and confer risk for developing the disease. Alleles containing 36-39 repeats (SEQ ID NO: 228) are considered incompletely penetrant, and those individuals harboring those alleles may or may not develop the disease (or may develop symptoms later in life) while alleles containing 40 repeats or more (SEQ ID NO: 259) are considered completely penetrant. In fact, no asymptomatic persons containing HD alleles with this many repeats have been reported. Those individuals with juvenile onset HD (<21 years of age) are often found to have 60 or more CAG repeats (SEQ ID NO: 229). In addition to an increase in CAG repeats, it has also been shown that HD can involve +1 and +2 frameshifts within the repeat sequences such that the region will encode a poly-serine polypeptide (encoded by AGC repeats in the case of a +1 frameshift) track rather than poly-glutamine (Davies and Rubinsztein (2006) *Journal of Medical Genetics* 43:893-896).

In HD, the mutant Htt allele is usually inherited from one parent as a dominant trait. Any child born of a HD patient has a 50% chance of developing the disease if the other parent was not afflicted with the disorder. In some cases, a parent may have an intermediate HD allele and be asymptomatic while, due to repeat expansion, the child manifests the disease. In addition, the HD allele can also display a phenomenon known as anticipation wherein increasing severity or decreasing age of onset is observed over several generations due to the unstable nature of the repeat region during spermatogenesis.

Furthermore, trinucleotide expansion in Htt leads to neuronal loss in the medium spiny gamma-aminobutyric acid (GABA) projection neurons in the striatum, with neuronal loss also occurring in the neocortex. Medium spiny neurons that contain enkephalin and that project to the external globus pallidum are more involved than neurons that contain substance P and project to the internal globus pallidum. Other brain areas greatly affected in people with Huntington's disease include the substantia nigra, cortical layers 3, 5, and 6, the CA1 region of the hippocampus, the angular gyms in the parietal lobe, Purkinje cells of the cerebellum, lateral tuberal nuclei of the hypothalamus, and the centromedialparafascicular complex of the thalamus (Walker (2007) *Lancet* 369:218-228).

The role of the normal Htt protein is poorly understood, but it may be involved in neurogenesis, apoptotic cell death, and vesicle trafficking. In addition, there is evidence that wild-type Htt stimulates the production of brain-derived neurotrophic factor (BDNF), a pro-survival factor for the striatal neurons. It has been shown that progression of HD correlates with a decrease in BDNF expression in mouse models of HD (Zuccato, et al. (2005) *Pharmacological Research* 52(2):133-139), and that delivery of either BDNF or glial cell line-derived neurotrophic factor (GDNF) via adeno-associated viral (AAV) vector-mediated gene delivery may protect straital neurons in mouse models of HD (Kells, et al. (2004) *Molecular Therapy* 9(5):682-688).

Treatment options for HD are currently very limited. Some potential methodologies designed to prevent the toxicities associated with protein aggregation that occurs through the extended poly-glutamine tract such as overexpression of chaperonins or induction of the heat shock response with the compound geldanamycin have shown a reduction in these toxicities in in vitro models. Other treatments target the role of apoptosis in the clinical manifestations of the disease. For example, slowing of disease symptoms has been shown via blockage of caspase activity in animal models in the offspring of a pairing of mice where one parent contained a HD allele and the other parent had a dominant negative allele for caspase 1. Additionally, cleavage of mutant HD Htt by caspase may play a role in the pathogenicity of the disease. Transgenic mice carrying caspase-6 resistant mutant Htt were found to maintain normal neuronal function and did not develop striatal neurodegeneration as compared to mice carrying a non-caspase resistant mutant Htt allele (see Graham, et al. (2006) *Cell* 125:1179-1191). Molecules which target members of the apoptotic pathway have also been shown to have a slowing affect on symptomology. For example, the compounds zVAD-fmk and minocycline, both of which inhibit caspase activity, have been shown to slow disease manifestation in mice. The drug remacemide has also been used in small HD human trials because the compound was thought to prevent the binding of the mutant Htt to the NDMA receptor to prevent the exertion of toxic effects on the nerve cell. However, no statistically significant improvements were observed in neuron function in these trials. In addition, the Huntington Study Group conducted a randomized, double-blind study using Co-enzyme Q. Although a trend towards slower disease progression among patients that were treated with coenzyme Q10 was observed, there was no significant change in the rate of decline of total functional capacity. (Di Prospero and Fischbeck, ibid). U.S. Patent Publication No. 2011/0082093 discloses specific zinc finger proteins targeted to Htt.

Thus, there remains a need for compositions and methods for the treatment and prevention of Huntington's Disease.

SUMMARY

Disclosed herein are methods and compositions for treating Huntington's Disease. In particular, provided herein are methods and compositions for modifying (e.g., modulating expression of) an HD Htt allele so as to treat Huntington Disease. Also provided are methods and compositions for generating animal models of Huntington's Disease.

Thus, in one aspect, engineered DNA binding domains (e.g., zinc finger proteins or TAL effector (TALE) proteins) that modulate expression of a HD allele (e.g., Htt) are provided. Engineered zinc finger proteins or TALEs are non-naturally occurring zinc finger or TALE proteins whose DNA binding domains (e.g., recognition helices or RVDs) have been altered (e.g., by selection and/or rational design) to bind to a pre-selected target site. Any of the zinc finger proteins described herein may include 1, 2, 3, 4, 5, 6 or more zinc fingers, each zinc finger having a recognition helix that binds to a target subsite in the selected sequence(s) (e.g., gene(s)). Similarly, any of the TALE proteins described herein may include any number of TALE RVDs. In some embodiments, at least one RVD has non-specific DNA binding. In some embodiments, at least one recognition helix (or RVD) is non-naturally occurring. In certain embodiments, the zinc finger proteins have the recognition helices shown in Tables 1A and 1B. In other embodiments, the zinc finger proteins bind to the target sequences shown in Tables 2A and 2B. In some embodiments, the zinc finger proteins comprise the recognition helices in Table 2C. In certain embodiments, the zinc finger proteins are formulated into a pharmaceutical composition, for example, for administration to a subject.

In one aspect, repressors (ZFP-TFs or TALE-TFs) are provided that bind to sequences entirely or partially outside the CAG repeat region of Htt. In another aspect, ZFP or TALE repressors (ZFP-TFs or TALE-TFs) are provided that bind to sequences within CAG repeat region of Htt. In some embodiments, these ZFP-TFs or TALE-TFs preferentially bind to expanded trinucleotide tracts relative to repeat tracts of a wild-type length, thereby achieving preferential repression of the expanded allele. In some embodiments these ZFP-TFs or TALE-TFs include protein interaction domains (or "dimerization domains") that allow multimerization when bound to DNA. In some embodiments, these ZFP-TFs or TALE TFs achieve cooperative DNA binding to the repeat sequence so that the expanded allele is bound more efficiently by a larger number of ZFPs or TALE proteins than the wild-type allele, allowing preferential repression of the mutant allele. These cooperative binding ZFP-TFs or TALE TFs may or may not further contain protein interaction domains that allow multimerization when bound to DNA. In some embodiments, ZFP TFs or TALE TFs form a stable complex of multimers of a given size, and thus are capable of preferentially interacting with a CAG tract above a certain minimum size, wherein that minimum size is greater than the length of a wild-type CAG tract.

In certain embodiments, the ZFPs or TALE proteins as described herein (e.g., two-handed, multimerizing, etc.) preferentially modify expression of a mutant Htt allele. In some embodiments, the ZFP or TALE binds specifically to mutant Htt alleles wherein the expanded tract encodes poly-glutamine, while in other embodiments, the ZFP or TALE binds specifically to a mutant Htt allele wherein the expansion tract encodes poly-serine. Thus, in some embodiments, the ZFP-TF or TALE-TF modulates both the wild type and mutant forms of the Htt allele. In certain embodiments, the ZFP or TALE modulates only the wild type Htt allele. In other embodiments, the ZFP or TALE modulates only the mutant form of Htt.

In other embodiments, repressing ZFP-TFs or TALE-TFs are provided which preferentially bind to known SNPs associated with the expanded HD Htt alleles. In this way, the ZFP-TFs or TALE-TFs are specific for mutant Htt alleles which contain the SNP, allowing for specific repression of the mutant Htt allele. In another aspect, ZFP-TFs or TALE-TFs that specifically activate the wild-type Htt allele by interacting with SNPs associated with wild-type alleles are provided. In this way, only the wild-type Htt allele is activated.

In certain embodiments, the zinc finger proteins (ZFPs) or TALE proteins as described herein can be placed in operative linkage with a regulatory domain (or functional domain) as part of a fusion protein. The functional domain can be, for example, a transcriptional activation domain, a transcriptional repression domain and/or a nuclease (cleavage) domain. By selecting either an activation domain or repression domain for fusion with the ZFP or TALE, such fusion proteins can be used either to activate or to repress gene expression. In some embodiments, a fusion protein comprising a ZFP or TALE targeted to a mutant Htt as described herein fused to a transcriptional repression domain that can be used to down-regulate mutant Htt expression is provided. In some embodiments, a fusion protein comprising a ZFP or TALE targeted to a wild-type Htt allele fused to a transcription activation domain that can up-regulate the wild type Htt allele is provided. In certain embodiments, the activity of the regulatory domain is regulated by an exogenous small molecule or ligand such that interaction with the cell's transcription machinery will not take place in the absence of the exogenous ligand. Such external ligands control the degree of interaction of the ZFP-TF or TALE-TF with the transcription machinery. The regulatory domain(s) may be operatively linked to any portion(s) of one or more of the ZFPs or TALEs, including between one or more ZFPs or TALEs, exterior to one or more ZFPs or TALEs and any combination thereof. Any of the fusion proteins described herein may be formulated into a pharmaceutical composition.

In some embodiments, the engineered DNA binding domains as described herein can be placed in operative linkage with nuclease (cleavage) domains as part of a fusion protein. In other embodiments, nuclease systems such as the CRISPR/Cas system may be utilized with a specific single guide RNA to target the nuclease to a target location in the DNA. In certain embodiments, such nucleases and nuclease fusions may be utilized for targeting mutant Htt alleles in stem cells such as induced pluripotent stem cells (iPSC), human embryonic stem cells (hESC), mesenchymal stem cells (MSC) or neuronal stem cells wherein the activity of the nuclease fusion will result in an Htt allele containing a wild type number of CAG repeats. In certain embodiments, pharmaceutical compositions comprising the modified stem cells are provided.

In yet another aspect, a polynucleotide encoding any of the DNA binding proteins described herein is provided. In another aspect, polynucleotides encoding a CRIPSR/Cas nuclease and a single guide RHA are provided. Such polynucleotides can be administered to a subject in which it is desirable to treat Huntington's Disease.

In still further aspects, the invention provides methods and compositions for the generation of specific model systems for the study of Huntington's Disease. In certain embodiments, provided herein are models in which mutant Htt alleles are generated using embryonic stem cells to generate cell and animal lines in which trinucleotide expansion tracts of specific lengths (50 (SEQ ID NO: 230), 80 (SEQ ID NO: 231), 109 (SEQ ID NO: 232) and 180 (SEQ ID NO: 233) CAG repeats, for example) are inserted into a wild-type Htt allele using zinc finger nuclease (ZFN), TALE-nuclease (TALEN), or CRISPR/Cas nuclease driven targeted integration. In certain embodiments, the model systems comprise in vitro cell lines, while in other embodiments, the model systems comprise transgenic animals. In any of the animal models described herein, the animal may be, for example, a rodent (e.g., rat, mouse), a primate (e.g., non-human primate) or a rabbit.

In yet another aspect, a gene delivery vector comprising any of the polynucleotides described herein is provided. In certain embodiments, the vector is an adenovirus vector (e.g., an Ad5/F35 vector), a lentiviral vector (LV) including integration competent or integration-defective lentiviral vectors, or an adenovirus associated viral vector (AAV). Thus, also provided herein are adenovirus (Ad) vectors, LV or adenovirus associate viral vectors (AAV) comprising a sequence encoding at least one nuclease (ZFN or TALEN) and/or a donor sequence for targeted integration into a target gene. In certain embodiments, the Ad vector is a chimeric Ad vector, for example an Ad5/F35 vector. In certain embodiments, the lentiviral vector is an integrase-defective lentiviral vector (IDLV) or an integration competent lentiviral vector. In certain embodiments the vector is pseudo-typed with a VSV-G envelope, or with other envelopes.

In some embodiments, model systems are provided for Huntington's disease wherein the target alleles (e.g., mutant Htt) are tagged with expression markers. In certain embodiments, the mutant alleles (e.g., mutant Htt) are tagged. In some embodiments, the wild type allele (e.g., wild-type Htt) is tagged, and in additional embodiments, both wild type and mutant alleles are tagged with separate expression markers. In certain embodiments, the model systems comprise in vitro cell lines, while in other embodiments, the model systems comprise transgenic animals.

Additionally, pharmaceutical compositions comprising the nucleic acids and/or proteins (e.g., ZFPs or TALEs or fusion proteins comprising the ZFPs or TALEs) are also provided. For example, certain compositions include a nucleic acid comprising a sequence that encodes one of the ZFPs or TALEs described herein operably linked to a regulatory sequence, combined with a pharmaceutically acceptable carrier or diluent, wherein the regulatory sequence allows for expression of the nucleic acid in a cell. In certain embodiments, the ZFPs or TALEs encoded are specific for a HD Htt allele. In some embodiments, pharmaceutical compositions comprise ZFPs or TALEs that modulate a HD Htt allele and ZFPs or TALEs that modulate a neurotrophic factor. Protein based compositions include one of more ZFPs or TALEs as disclosed herein and a pharmaceutically acceptable carrier or diluent.

In yet another aspect also provided is an isolated cell comprising any of the proteins, polynucleotides and/or compositions as described herein.

In another aspect, provided herein are methods for treating and/or preventing Huntington's Disease using the methods and compositions described herein. In some embodiments, the methods involve compositions where the polynucleotides and/or proteins may be delivered using a viral vector, a non-viral vector (e.g., plasmid) and/or combinations thereof. In some embodiments, the methods involve compositions comprising stem cell populations comprising a ZFP or TALE, or altered with the ZFNs, TALENs or the CRISPR/Cas nuclease system of the invention.

These and other aspects will be readily apparent to the skilled artisan in light of disclosure as a whole.

BRIEF DESCRIPTION OF THE DRAWINGS

FIGS. 1A through 1E are schematics depicting wild type and mutant (Huntington's Disease, HD) Huntingtin (Htt) allele and various ZFP-TFs binding to those alleles. FIG. 1A shows ZFP designs that bind outside of the CAG repeat, and therefore are predicted to bind equally to the wild type allele and the mutant (HD) allele. "KRAB" refers to the KRAB repression domain from the KOX1 gene and "ZFP" refers to the zinc finger DNA binding protein. "Standard ZFP TF" is a ZFP transcription factor fusion protein in which the zinc finger DNA binding domains are linked to the KRAB repression domain. FIG. 1B shows ZFP-TFs designed to bind within the CAG region. FIG. 1C depicts a "two-handed ZFP TF," which is a ZFP transcription factor in which two clusters of zinc finger domains are separated by a rigid protein sequences. The functional (repression) domain is depicted exterior to one ZFP in this Figure, but it will be apparent that the functional domain may be between the ZFPs or exterior to the ZFPs on either end of the protein. FIG. 1D depicts a "multimerizing ZFP TF," which is a ZFP TF that is capable of multimerizing through a multimerization domain (depicted as speckled boxes). FIG. 1E depicts a ZFP-ZFP-KRAB configuration where two zinc finger DNA binding domains are linked by a flexible linker and are also fused to a KRAB domain. It will be apparent to the skilled artisan that in all fusion proteins, the functional domain can be on either end of the DNA binding domain, and that the DNA binding domain may comprise a wide number range of zinc fingers. Also depicted in FIG. 1 as a box with black diamonds is a functional domain (e.g., activation, repression, cleavage domain). It will be apparent to the skilled artisan that the exemplary models presented in the Figures may apply to TALE TFs as well.

FIGS. 2A through 2E depict the repression of both alleles of Htt by ZFPs as described in FIG. 1A using ZFP TFs that do not bind to the CAG repeat sequences. The ZFP identification numbers as shown in Tables 1A and 1B are indicated below the bars. FIG. 2A depicts repression of the human Htt alleles in HEK293 cells using ZFPs targeted to five loci in the human gene. A diagram of the human Htt gene is shown and the locations of ZFP binding sites are shown. For each ZFP group, each bar represents an independent transfection. FIG. 2B depicts a Western blot showing Htt protein levels in HEK293 cells transfected with the GFP control or the 18856 ZFP TF repressor (comprising the KRAB repression domain of KOX1), where the NFκB p65 levels ("p65") were used to confirm equal protein loading. The Western blot confirms the repression of Htt expression by the ZFP-TF. FIG. 2C depicts a similar set of data as FIG. 2A for the mouse Htt specific ZFP in Neuro2A cells. As in FIG. 2A, a diagram of the mouse Htt gene is shown and the locations of ZFP binding sites are indicated. FIGS. 2D and 2E demonstrate the repression of mouse Htt gene expression (RNA) in immortalized striatal cells, where different doses of ZFP-TF mRNA were used for transfection. In all cases except FIG. 2B, Htt mRNA levels were measured by real-time RT-PCR and normalized to those of Actin mRNA.

FIGS. 3A through 3G depict selective repression of mutant Htt by using ZFPs binding within the CAG repeat region, as illustrated in FIG. 1B. This model illustrates that the longer CAG repeat region in the mutant allele allows for increased binding of CAG-targeted ZFP repressor molecules. FIG. 3A depicts different repressor activities on the endogenous Htt gene (with normal CAG repeat length) by CAG-targeted ZFPs in HEK293 cells. FIG. 3B shows repression of luciferase reporters controlled by Htt promoter/exon1 fragments containing CAG repeats of varying lengths, ranging from 10 (SEQ ID NO: 234) to 47 (SEQ ID NO: 235) CAG repeats. CAG10 (SEQ ID NO: 234) (leftmost bar for each of the two indicated conditions) shows results with 10 CAG repeats (SEQ ID NO: 234); CAG17 (SEQ ID NO: 236) (bar second from the left for each of the two indicated conditions) shows results with 17 CAG repeats (SEQ ID NO: 236); CAG23 (SEQ ID NO: 237) (bar second from the right for each of the two indicated conditions) shows results with 23 CAG repeats (SEQ ID NO: 237); and CAG47 (SEQ ID NO: 235) (right-most bar for each of the two indicated conditions) shows results with 47 CAG repeats (SEQ ID NO: 235). The schematic above the graph depicts the arrangement of the Htt promoter, exon 1, the CAG repeats and the reporter luciferase gene used in this system. The data demonstrate that increasing the number of CAGs leads to a decreased expression from the Htt promoter by a CAG-targeted ZFP. Furthermore, FIG. 3C demonstrates that, while a relatively weak CAG-targeted ZFP does not repress the luciferase reporter that contains a normal-length CAG repeat as well as a strong CAG repressor, it drives similar repression of a luciferase reporter that contains an expanded CAG repeat as the strong CAG-targeted ZFP. at all doses tested. "pRL-Htt-CAG23-intron 1" ("CAG23" disclosed as SEQ ID NO: 237) (left bar of each pair) corresponds to expression from the wild type allele while "pRL-HttCAG47-intron 1" ("CAG47" disclosed as SEQ ID NO: 235) (right bar of each pair) correlates with expression from the mutant expanded Htt allele (containing 47 CAG repeats (SEQ ID NO: 235)). FIG. 3D is a graph depicting repression of mutant Htt (111 CAG (SEQ ID NO: 238)) by CAG-targeted ZFPs in immortalized mouse striatal cells derived from HdH(Q111/Q7) knock-in mice. Wild-type expression is shown in the left bar of each pair and knock-in expression in the right bar of each pair. ZFP-TFs comprising the specified ZFP fused to the KRAB repression domain were tested using three different concentrations of ZFP mRNA in the transfections. FIG. 3E depicts mutant Htt repression by CAG-targeted ZFPs in a HD patient derived fibroblast line (CAG15/70) (SEQ ID NOS 239 and 240). In this fibroblast line, the wild type Htt allele comprises 15 CAG repeats ("099T(CAG15)" (SEQ ID NO: 239), middle bar of each indicated condition) and the mutant expanded Htt allele comprises 70 CAG repeats ("099C(CAG70)" (SEQ ID NO: 240), right bar of each indicated condition). FIG. 3F shows selective repression of mutant Htt expression in 4 different HD patient derived fibroblast cell lines. The numbers above each grouping indicate the number of CAG repeats on the wildtype Htt allele (e.g. 15 (SEQ ID NO: 239) or 18 (SEQ ID NO: 245)) and on the mutant allele (e.g. 70 (SEQ ID NO: 240), 67 (SEQ ID NO: 242), 45 (SEQ ID NO: 243) and 44 (SEQ ID NO: 244)); where two different doses of ZFP mRNA were tested. The left-bar of each pair shows wild-type Htt expression and the right bar of each shows expression of mutant Htt. FIG. 3G depicts Htt expression in HD derived patient fibroblasts as assayed by Western blot analysis in the presence of the ZFP-TFs 30640, 32528 and 30657. The slower migrating protein bands are those produced by the expanded mutant Htt alleles. 32528 binds to the transcription start site of Htt (TSS) and thus inhibits expression from both alleles, while 30640 and 30657 bind to the CAG repeats (CAG). FIG. 3G discloses "CAG 15/67" as SEQ ID NOS 239 and 242, and "CAG 15/70" as SEQ ID NOS 239 and 240.

FIGS. 4A and 4B depict repression of the mutant Htt in a HD patient derived fibroblast line by a panel of ZFPs targeted to the CAG repeat. A range of RNA concentrations were used from 0.1 ng to 3 μg. In FIGS. 4A and 4B, the left bar of each indicated conditions shows total Htt expression, the middle bar shows expression of Htt in fibroblasts in which the Htt allele comprises 18 CAG repeats ("099T (CAG18)" (SEQ ID NO: 245) and the mutant expanded Htt allele comprises 45 CAG repeats 099T (CAG45) (SEQ ID NO: 243). FIG. 4B discloses "CAG15" as SEQ ID NO: 239 and "CAG70" as SEQ ID NO: 240.

FIG. 5 discloses CAG repeats as SEQ ID NOS 240, 239, 253, 249, 254-258, 258-259, and 259, respectively, in order of appearance.

FIG. 6A depicts qPCR analysis of Htt repression performed on six biological replicates (six separate transfections) of HD fibroblasts (CAG18 (SEQ ID NO: 245) (middle bars)/CAG45 (SEQ ID NO: 243), right bars) using 30640, 30645, or 33074. The four most similar replicates by qPCR were then selected for microarray analysis, and the data is presented in FIG. 6B.

FIG. 7 depicts Htt repression in CAG17/69 (SEQ ID NOS 236 and 246) neuronal stem cells (NSC). The cells were transfected with ZFP mRNA at indicated doses. Left bars under each of the indicated doses show results in CAG17 (SEQ ID NO: 236) cells, middle bars show results in wild-type cells, right bars show results in CAG69 (SEQ ID NO: 246) cells.

FIG. 8 depicts Htt expression in neurons differentiated from HD embryonic stem cells (ESC) (CAG 17/48) (SEQ ID NOS 236 and 247) treated with ZFP TFs. The cells were transfected with ZFP mRNA at indicated doses.

FIGS. 10A through 10D depict ZFPs with multimerization domains that specifically targets expanded CAG repeats, as illustrated in FIG. 1D. FIG. 10A shows a single ZFP that have four components: (i) a KOX repressor domain (oval labeled "repressor"); (ii) an array of 2-6 fingers (two shown, small ovals marked "Z") that binds to $(CAG)_N$ or a permutation of this sequence; and (iii) two dimerization domains (rectangles labeled "d1" and "d2") that interact in an antiparallel configuration. These domains allow the ZFP to polymerize within the major groove of a CAG tract. FIG. 10B shows a sketch of the binding event with a multimer of 3 ZFPs. It will be apparent that any number of multimers can be used and that the functional domain may be positioned anywhere on one or more of the individual ZFPs and that these diagrams are applicable to TALE-TFs as well. FIG. 10B discloses the sequences as SEQ ID NO: 260. FIG. 10C shows protein sequences of the four ZFP monomer scaffolds that are designed to multimerize via interactions between dimerizing zinc fingers (DZ). Scaffolds are named DZ1 (SEQ ID NOS 180 & 213), DZ2 (SEQ ID NOS 181 & 214), DZ3 (SEQ ID NOS 182 & 215) and DZ4 (SEQ ID NOS 183 & 216). Dimerizing zinc finger domains are underlined, while the repression domain and nuclear localization sequence are indicated by bold underline and italic text (respectively). FIG. 10D shows protein sequences of the seven ZFP monomer scaffolds that are designed to multimerize via interactions between coiled-coils (CC). Scaffolds are named CC1 (SEQ ID NOS 184 & 217), CC2 (SEQ ID NOS 185 & 218), CC3 (SEQ ID NOS 186 & 219), CC4 (SEQ ID NO S 187 & 220), CC2 (SEQ ID NOS 221 & 222), CC5 (SEQ ID NOS 188 & 223), CC6 (SEQ ID NOS 189 & 224) and CC7 (SEQ ID NOS 190 & 225). Coiled-coil sequences are underlined, while the repression domain and nuclear localization sequence are indicated by bold underline and italic text (respectively). The location of the ZFP region of each scaffold, which will vary between designs, is indicated by "[ZFP]." The location of the (DNA-binding) ZFP region of each scaffold, which will vary between designs, is indicated by "[ZFP]."

FIGS. 11A and 11B depict activity of ZFP-TFs with dimerization domains. In FIG. 11A, ZFP-TFs with "coiled coil" (CC) domains were tested with luciferase reporters. pRL-Htt CAG17 ("CAG17" disclosed as SEQ ID NO: 236) (left bar of each pair) stands for renilla luciferase reporter controlled by human Htt promoter/exon1 fragment with 17 CAG (SEQ ID NO: 236); pGL3-Htt-CAG47 ("CAG47" disclosed as SEQ ID NO: 235) (right bar of each pair) stands for firefly luciferase reporter controlled by human Htt promoter/exon1 fragment with 47 CAG repeats (SEQ ID NO: 235). See text in Example 10 for description of the various dimerization domains. In FIG. 11B, ZFPs with the dimerizing zinc finger "DZ" domains were tested with the same luciferase reporters, and demonstrates increased repression with some ZFP-TF dimerization domains. The left bar in each doublet indicates the expression from the 17CAG repeat (SEQ ID NO: 236) Htt allele while the right bar indicates expression from 47 CAG repeat (SEQ ID NO: 235) Htt allele.

FIGS. 12A and 12B depict repression of Htt by ZFP-ZFP-KOX proteins. FIG. 12A depicts Htt repression by the single 33088 and 33084 ZFP-TFs, and repression by the 33088-33088 and 33088-33084 ZFP-ZFP-KOX proteins in wild-type (left bar), CAG18 (SEQ ID NO: 245) (middle bar) and CAG45 (SEQ ID NO: 243) (right bar) (FIG. 12A) HD fibroblasts; FIG. 12B depicts Htt repression by 33088-33088 and 33088-33084 ZFP-ZFP-KOX in wild type (left bar), CAG 20 (SEQ ID NO: 248) (middle bar) and CAG41 (SEQ ID NO: 249) (left bar) HD fibroblasts.

FIG. 13A demonstrates ZFP-TF-driven up-regulation of the mouse Htt genes at the RNA level in Neuro2A cells using a ZFP fused to the p65 activation domain. Double bars indicate duplicate transfections. FIG. 13B depicts a Western blot demonstrating increased Htt protein production driven by the ZFP. FIG. 13C depicts a wild type mouse Htt allele and a "knock in" Htt allele where mouse sequence (most of exon1 and part of intron 1, line above wild-type allele schematic) has been replaced with corresponding human sequence with CAG expansion (line over knock-in allele schematic). FIG. 13C discloses "CAG7" as SEQ ID NO: 261 and "CAG>100" as SEQ ID NO: 241. FIG. 13D depicts the alignment between mouse sequence (SEQ ID NO:191) that was replaced with the corresponding human sequence (SEQ ID NO:192) such that the knock-in allele has sufficient sequence divergence to allow ZFPs (shown in A and B) to be designed to bind specifically the mouse sequence. FIG. 13E depicts specific activation of the wild type mouse Htt allele in immortalized striatal cells derived from the HdhQ111/Q7 knock-in mice. The left-bar shows results in wild-type cells and right bar shows results in knock-in mutant allele cells.

FIG. 14A depicts results from ZFNs that cleave early Htt exons while FIG. 14B depicts results from ZFNs that cleave near the stop codon. Inactive ZFN pairs were also observed (lanes not annotated with in-del percentages).

DETAILED DESCRIPTION

Figure 1E:
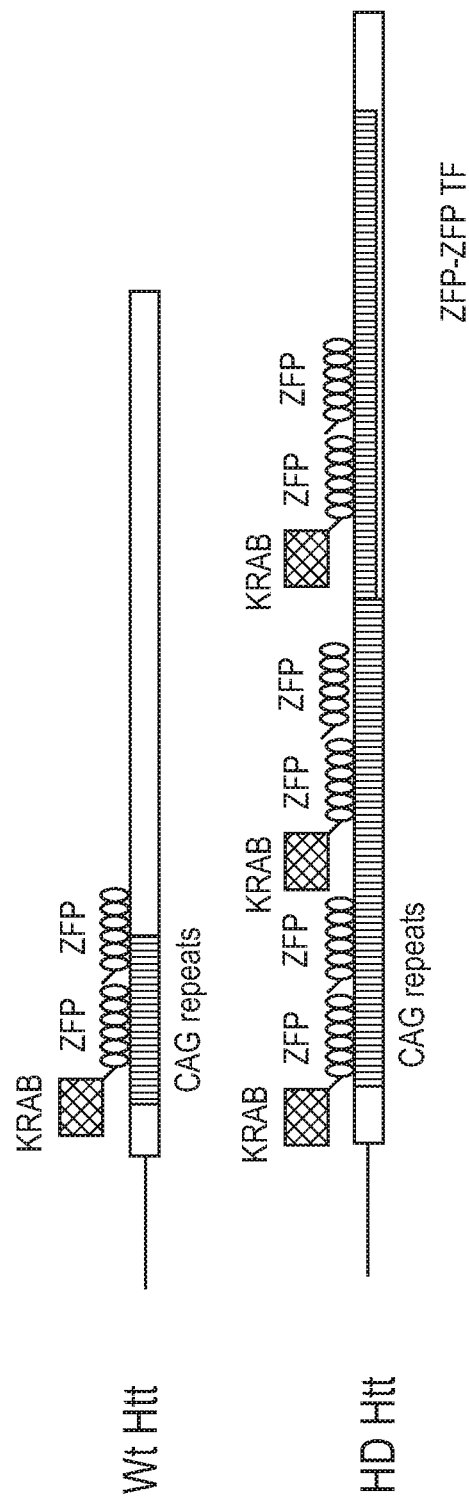

Disclosed herein are compositions and methods for treating Huntington's disease (HD). In particular, Htt-modulating transcription factors comprising zinc finger proteins (ZFP TFs) or TALEs (TALE-TF) and methods utilizing such proteins are provided for use in treating or preventing Huntington's disease. For example, ZFP-TFs or TALE-TFs which repress expression of a mutant Htt allele or activate expression of a wild-type Htt allele are provided. In addition, zinc finger nucleases (ZFNs), TALE nucleases (TALENs) or CRISPR/Cas nuclease systems that modify the genomic structure of the genes associated with HD are provided. For example, ZFNs, TALENs or CRISPR/Cas nuclease systems that are able to specifically alter portions of a mutant form of Htt are provided. These include compositions and methods using engineered zinc finger proteins or engineered TALE proteins, i.e., non-naturally occurring proteins which bind to a predetermined nucleic acid target sequence.

Thus, the methods and compositions described herein provide methods for treatment and prevention of Huntington's Disease, and these methods and compositions can comprise zinc finger transcription factors or TALE transcription factors that are capable of modulating target genes as well as engineered zinc finger and TALE nucleases and CRISPR/Cas nuclease systems capable of modifying or editing Htt.

GENERAL

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook, et al., MOLECULAR CLONING: A LABORATORY MANUAL, Second edition, Cold Spring Harbor Laboratory Press, 1989 and Third edition, 2001; Ausubel, et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolfe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein.

Zinc finger binding domains or TALE DNA binding domains can be "engineered" to bind to a predetermined nucleotide sequence, for example via engineering (altering one or more amino acids) of the recognition helix region of a naturally occurring zinc finger protein or by engineering the RVDs of a TALE protein. Therefore, engineered zinc finger proteins or TALEs are proteins that are non-naturally occurring. Non-limiting examples of methods for engineering zinc finger proteins or TALEs are design and selection. A designed zinc finger protein or TALE is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; and 6,534,261; see also International Patent Publication Nos. WO 98/53058; WO 98/53059; WO 98/53060; WO 02/016536 and WO 03/016496 and U.S. Patent Publication No. 2011/0301073.

A "selected" zinc finger protein or TALE is a protein not found in nature whose production results primarily from an empirical process such as phage display, interaction trap or hybrid selection. See e.g., U.S. Pat. Nos. 5,789,538; 5,925,523; 6,007,988; 6,013,453; 6,200,759; International Patent Publication Nos. WO 95/19431; WO 96/06166; WO 98/53057; WO 98/54311; WO 00/27878; WO 01/60970; WO 01/88197, WO 02/099084; and WO 2011/146121; and U.S. Patent Publication No. 2011/0301073.

"Recombination" refers to a process of exchange of genetic information between two polynucleotides. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break in the target sequence (e.g., cellular chromatin) at a predetermined site, and a "donor" polynucleotide, having homology to the nucleotide sequence in the region of the break, can be introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger or TALE proteins can be used for additional double-stranded cleavage of additional target sites within the cell.

In certain embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present.

In any of the methods described herein, the first nucleotide sequence (the "donor sequence") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

Any of the methods described herein can be used for partial or complete inactivation of one or more target sequences in a cell by targeted integration of donor sequence that disrupts expression of the gene(s) of interest. Cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or noncoding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miRNAs), etc.).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 2005/0064474; 2007/0218528; 2008/0131962; and 2011/0201055, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogeneous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "multimerization domain", (also referred to as a "dimerization domain" or "protein interaction domain") is a domain incorporated at the amino, carboxy or amino and carboxy terminal regions of a ZFP TF or TALE TF. These domains allow for multimerization of multiple ZFP TF or TALE TF units such that larger tracts of trinucleotide repeat domains become preferentially bound by multimerized ZFP TFs or TALE TFs relative to shorter tracts with wild-type numbers of lengths. Examples of multimerization domains include leucine zippers. Multimerization domains may also be regulated by small molecules wherein the multimerization domain assumes a proper conformation to allow for interaction with another multimerization domain only in the presence of a small molecule or external ligand. In this way, exogenous ligands can be used to regulate the activity of these domains.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP or TALE protein as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP or TALE DNA-binding domain is fused to an activation domain, the ZFP or TALE DNA-binding domain and the activation domain are in operative linkage if, in the fusion polypeptide, the ZFP or TALE DNA-binding domain portion is able to bind its target site and/or its binding site, while the activation domain is able to upregulate gene expression. ZFPs fused to domains capable of regulating gene expression are collectively referred to as "ZFP-TFs" or "zinc finger transcription factors", while TALEs fused to domains capable of regulating gene expression are collectively referred to as "TALE-TFs" or "TALE transcription factors." When a fusion polypeptide in which a ZFP DNA-binding domain is fused to a cleavage domain (a "ZFN" or "zinc finger nuclease"), the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site. When a fusion polypeptide in which a TALE DNA-binding domain is fused to a cleavage domain (a "TALEN" or "TALE nuclease"), the TALE DNA-binding domain and the cleavage domain are in operative linkage if, in the fusion polypeptide, the TALE DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one ore more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel, et al., supra. The ability of a protein to interact with another protein can be determined, for example, by co-immunoprecipitation, two-hybrid assays or complementation, both genetic and biochemical. See, for example, Fields, et al. (1989) Nature 340:245-246; U.S. Pat. No. 5,585,245 and International Patent Publication No. WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

DNA-Binding Domains

Described herein are compositions comprising a DNA-binding domain that specifically bind to a target sequence in any gene comprising a trinucleotide repeat, including, but not limited to, Htt. Any DNA-binding domain can be used in the compositions and methods disclosed herein.

In certain embodiments, the DNA binding domain comprises a zinc finger protein. Preferably, the zinc finger protein is non-naturally occurring in that it is engineered to bind to a target site of choice. See, for example, Beerli, et al. (2002) Nature Biotechnol. 20:135-141; Pabo, et al. (2001) Ann. Rev. Biochem. 70:313-340; Isalan, et al. (2001) Nature Biotechnol. 19:656-660; Segal, et al. (2001) Curr. Opin. Biotechnol. 12:632-637; Choo, et al. (2000) Curr. Opin. Struct. Biol. 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253, 273; and U.S. Patent Publication Nos. 2005/0064474; 2007/0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as International Patent Publication Nos. WO 98/37186; WO 98/53057; WO 00/27878; and WO 01/88197 and GB 2,338,237. In addition, enhancement of binding specificity for zinc finger binding domains has been described, for example, in co-owned International Patent Publication No. WO 02/077227.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. In addition, enhancement of binding specificity for zinc finger binding domains has been described, for example, in co-owned International Patent Publication No. WO 02/077227.

Selection of target sites; ZFPs and methods for design and construction of fusion proteins (and polynucleotides encoding same) are known to those of skill in the art and described in detail in U.S. Pat. Nos. 6,140,0815; 789,538; 6,453,242; 6,534,261; 5,925,523; 6,007,988; 6,013,453; and 6,200,759; International Patent Publication Nos. WO 95/19431; WO 96/06166; WO 98/53057; WO 98/54311; WO 00/27878; WO 01/60970; WO 01/88197; WO 02/099084; WO 98/53058; WO 98/53059; WO 98/53060; WO 02/016536; and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

In certain embodiments, the DNA binding domain is an engineered zinc finger protein that binds (in a sequence-specific manner) to a target site in a Htt gene and modulates expression of Htt. The ZFPs can bind selectively to either a mutant Htt allele or a wild-type Htt sequence. Htt target sites typically include at least one zinc finger but can include a plurality of zinc fingers (e.g., 2, 3, 4, 5, 6 or more fingers). Usually, the ZFPs include at least three fingers. Certain of the ZFPs include four, five or six fingers, while some ZFPs include 8, 9, 10, 11 or 12 fingers. The ZFPs that include three fingers typically recognize a target site that includes 9 or 10 nucleotides; ZFPs that include four fingers typically recognize a target site that includes 12 to 14 nucleotides; while ZFPs having six fingers can recognize target sites that include 18 to 21 nucleotides. The ZFPs can also be fusion proteins that include one or more regulatory domains, which domains can be transcriptional activation or repression domains. In some embodiments, the fusion protein comprises two ZFP DNA binding domains linked together. These zinc finger proteins can thus comprise 8, 9, 10, 11, 12 or more fingers. In some embodiments, the two DNA binding domains are linked via an extendable flexible linker such that one DNA binding domain comprises 4, 5, or 6 zinc fingers and the second DNA binding domain comprises an additional 4, 5, or 5 zinc fingers. In some embodiments, the linker is a standard inter-finger linker such that the finger array comprises one DNA binding domain comprising 8, 9, 10, 11 or 12 or more fingers. In other embodiments, the linker is an atypical linker such as a flexible linker. The DNA binding domains are fused to at least one regulatory domain and can be thought of as a 'ZFP-ZFP-TF'architecture. Specific examples of these embodiments can be referred to as "ZFP-ZFP-KOX" which comprises two DNA binding domains linked with a flexible linker and fused to a KOX repressor and "ZFP-KOX-ZFP-KOX" where two ZFP-KOX fusion proteins are fused together via a linker.

Alternatively, the DNA-binding domain may be derived from a nuclease. For example, the recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort, et al. (1997) *Nucleic Acids Res.* 25:3379-3388; Dujon, et al. (1989) *Gene* 82:115-118; Perler, et al. (1994) *Nucleic Acids Res.* 22:1125-1127; Jasin (1996) *Trends Genet.* 12:224-228; Gimble, et al. (1996) *J. Mol. Biol.* 263:163-180; Argast, et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier, et al. (2002) *Molec. Cell* 10:895-905; Epinat, et al. (2003) *Nucleic Acids Res.* 31:2952-2962; Ashworth, et al. (2006) *Nature* 441:656-659; Pâques, et al. (2007) *Current Gene Therapy* 7:49-66; U.S. Patent Publication No. 2007/0117128.

"Two handed" zinc finger proteins are those proteins in which two clusters of zinc finger DNA binding domains are separated by intervening amino acids so that the two zinc finger domains bind to two discontinuous target sites. An example of a two handed type of zinc finger binding protein is SIP1, where a cluster of four zinc fingers is located at the amino terminus of the protein and a cluster of three fingers is located at the carboxyl terminus (see Remade, et al. (1999) *EMBO Journal* 18(18):5073-5084). Each cluster of zinc fingers in these proteins is able to bind to a unique target sequence and the spacing between the two target sequences can comprise many nucleotides. Two-handed ZFPs may include a functional domain, for example fused to one or both of the ZFPs. Thus, it will be apparent that the functional domain may be attached to the exterior of one or both ZFPs (see, FIG. 1C) or may be positioned between the ZFPs (attached to both ZFPs) (see, FIG. 4).

Specific examples of Htt-targeted ZFPs are disclosed in Tables 1A and 1B. The first column in this table is an internal reference name (number) for a ZFP and corresponds to the same name in column 1 of Tables 2A and 2B. "F" refers to the finger and the number following "F" refers which zinc finger (e.g., "F1" refers to finger 1).

TABLE 1A

Htt-targeted zinc finger proteins

| SBS # | Design | | | | | |
|---|---|---|---|---|---|---|
| | F1 | F2 | F3 | F4 | F5 | F6 |
| 18856 | RSDDLSR (SEQ ID NO: 1) | RNDNRTK (SEQ ID NO: 2) | RSDDLTR (SEQ ID NO: 3) | RSDDRKT (SEQ ID NO: 4) | RSADLTR (SEQ ID NO: 5) | QSSDLRR (SEQ ID NO: 6) |
| 25920 | RSAALSR (SEQ ID NO: 58) | RSDALAR (SEQ ID NO: 59) | RSDNLSE (SEQ ID NO: 60) | KRCNLRC (SEQ ID NO: 61) | QSSDLRR (SEQ ID NO: 6) | NA |
| 25921 | WRSCRSA (SEQ ID NO: 62) | DRSNLSR (SEQ ID NO: 9) | QRTHLTQ (SEQ ID NO: 53) | RSAHLSR (SEQ ID NO: 46) | TSGHLSR (SEQ ID NO: 43) | NA |
| 25923 | RSDDLSR (SEQ ID NO: 1) | RNDNRTK (SEQ ID NO: 2) | WRSCRSA (SEQ ID NO: 62) | RSDNLAR (SEQ ID NO: 7) | QSGHLSR (SEQ ID NO: 41) | NA |
| 25922 | RSAALSR (SEQ ID NO: 58) | RSDALAR (SEQ ID NO: 59) | RSDNLSE (SEQ ID NO: 60) | KRCNLRC (SEQ ID NO: 61) | QSSDLSR (SEQ ID NO: 31) | DRSHLAR (SEQ ID NO: 13) |

TABLE 1B

Human and Mouse Htt-targeted zinc finger proteins

| SBS # | Design | | | | | |
|---|---|---|---|---|---|---|
| | F1 | F2 | F3 | F4 | F5 | F6 |
| 32468 | RSDNLAR (SEQ ID NO: 7) | WRGDRVK (SEQ ID NO: 8) | DRSNLSR (SEQ ID NO: 9) | TSGSLTR (SEQ ID NO: 10) | ERGTLAR (SEQ ID NO: 11) | RSDDRKT (SEQ ID NO: 4) |
| 32501 | RSDALSR (SEQ ID NO: 12) | DRSHLAR (SEQ ID NO: 13) | RSDHLSR (SEQ ID NO: 14) | QSSDLTR (SEQ ID NO: 15) | TSGNLTR (SEQ ID NO: 16) | DRSHLAR (SEQ ID NO: 13) |
| 31809 | RSDDLSR (SEQ ID NO: 1) | RNDNRTK (SEQ ID NO: 2) | RSDDLTR (SEQ ID NO: 3) | RSDDRKT (SEQ ID NO: 4) | RSDDLTR (SEQ ID NO: 3) | QSSDLRR (SEQ ID NO: 6) |
| 32528 | QSGHLQR (SEQ ID NO: 17) | TSGNLTR (SEQ ID NO: 16) | QSGDLTR (SEQ ID NO: 18) | DRSHLAR (SEQ ID NO: 13) | RSDVLST (SEQ ID NO: 19) | VRSRLRR (SEQ ID NO: 20) |
| 30580 | RSDNLAR (SEQ ID NO: 7) | WRGDRVK (SEQ ID NO: 8) | DRSDLSR (SEQ ID NO: 22) | RSDALAR (SEQ ID NO: 59) | ERGTLAR (SEQ ID NO: 11) | RSDDRKT (SEQ ID NO: 4) |
| 30929 | DRSTLRQ (SEQ ID NO: 21) | DRSDLSR (SEQ ID NO: 22) | QSSTRAR (SEQ ID NO: 23) | RSDTLSE (SEQ ID NO: 24) | HRRSRWG (SEQ ID NO: 25) | NA |
| 32538 | DRSDLSR (SEQ ID NO: 22) | RRDTLRS (SEQ ID NO: 26) | RSDHLST (SEQ ID NO: 27) | QSAHRIT (SEQ ID NO: 28) | QSGDLTR (SEQ ID NO: 18) | DRSHLAR (SEQ ID NO: 13) |
| 32567 | RSDHLSE (SEQ ID NO: 29) | QNAHRKT (SEQ ID NO: 30) | QSSDLSR (SEQ ID NO: 31) | HRSTRNR (SEQ ID NO: 32) | QSSDLSR (SEQ ID NO: 31) | HRSTRNR (SEQ ID NO: 32) |
| 29627 | DRSNLSR (SEQ ID NO: 9) | LRQDLKR (SEQ ID NO: 33) | DRSHLTR (SEQ ID NO: 34) | DRSNLTR (SEQ ID NO: 35) | RSDHLST (SEQ ID NO: 27) | QSAHRIT (SEQ ID NO: 28) |

TABLE 1B-continued

Human and Mouse Htt-targeted zinc finger proteins

| SBS # | Design | | | | | |
|---|---|---|---|---|---|---|
| | F1 | F2 | F3 | F4 | F5 | F6 |
| 29628 | TSGNLTR (SEQ ID NO: 16) | LKQMLAV (SEQ ID NO: 36) | RSDSLSA (SEQ ID NO: 37) | DRSDLSR (SEQ ID NO: 22) | RSDALST (SEQ ID NO: 38) | DRSTRTK (SEQ ID NO: 39) |
| 29631 | QSSDLSR (SEQ ID NO: 31) | DRSALAR (SEQ ID NO: 40) | QSSDLSR (SEQ ID NO: 31) | QSGHLSR (SEQ ID NO: 41) | RSDVLSE (SEQ ID NO: 42) | TSGHLSR (SEQ ID NO: 43) |
| 29632 | RSDTLSE (SEQ ID NO: 24) | KLCNRKC (SEQ ID NO: 44) | TSGNLTR (SEQ ID NO: 16) | HRTSLTD (SEQ ID NO: 45) | RSAHLSR (SEQ ID NO: 46) | QSGNLAR (SEQ ID NO: 47) |
| 29637 | DRSNLSR (SEQ ID NO: 9) | QSGNLAR (SEQ ID NO: 47) | DRSNLSR (SEQ ID NO: 9) | LKHHLTD (SEQ ID NO: 48) | QSGDLTR (SEQ ID NO: 18) | YRWLRNN (SEQ ID NO: 49) |
| 29638 | RSDHLSQ (SEQ ID NO: 50) | RSAVRKN (SEQ ID NO: 51) | QSSDLSR (SEQ ID NO: 31) | QSGDLTR (SEQ ID NO: 18) | WSTSLRA (SEQ ID NO: 52) | NA |
| 25917 | DRSNLSR (SEQ ID NO: 9) | QRTHLTQ (SEQ ID NO: 53) | RSSHLSR (SEQ ID NO: 54) | TSGSLSR (SEQ ID NO: 55) | TRQNRDT (SEQ ID NO: 56) | NA |
| 25916 | DQSTLRN (SEQ ID NO: 57) | RSAALSR (SEQ ID NO: 58) | RSDALAR (SEQ ID NO: 59) | RSDNLSE (SEQ ID NO: 60) | KRCNLRC (SEQ ID NO: 61) | NA |
| 33074 | RSDNLSE (SEQ ID NO: 60) | KRCNLRC (SEQ ID NO: 61) | QSGDLTR (SEQ ID NO: 18) | QSGDLTR (SEQ ID NO: 18) | RSDNLSE (SEQ ID NO: 60) | KRCNLRC (SEQ ID NO: 61) |
| 33080 | QSGDLTR (SEQ ID NO: 18) | QSGDLTR (SEQ ID NO: 18) | RSDNLSE (SEQ ID NO: 60) | KRCNLRC (SEQ ID NO: 61) | QSGDLTR (SEQ ID NO: 18) | QSGDLTR (SEQ ID NO: 18) |
| 33084 | QSSDLSR (SEQ ID NO: 31) | HRSTRNR (SEQ ID NO: 32) | RSDTLSE (SEQ ID NO: 24) | RRWTLVG (SEQ ID NO: 64) | NA | NA |
| 33088 | QSSDLSR (SEQ ID NO: 31) | HRSTRNR (SEQ ID NO: 32) | RSAVLSE (SEQ ID NO: 148) | QSSDLSR (SEQ ID NO: 31) | HRSTRNR (SEQ ID NO: 32) | NA |
| 30643 | RSDNLSE (SEQ ID NO: 60) | KRCNLRC (SEQ ID NO: 61) | QSSDLSR (SEQ ID NO: 31) | QWSTRKR (SEQ ID NO: 63) | QSSDLSR (SEQ ID NO: 31) | QWSTRKR (SEQ ID NO: 63) |
| 30648 | RSDNLSE (SEQ ID NO: 60) | KRCNLRC (SEQ ID NO: 61) | RSDNLSE (SEQ ID NO: 60) | KRCNLRC (SEQ ID NO: 61) | RSDNLSE (SEQ ID NO: 60) | KRCNLRC (SEQ ID NO: 61) |
| 30645 | RSDNLSE (SEQ ID NO: 60) | KRCNLRC (SEQ ID NO: 61) | QSSDLSR (SEQ ID NO: 31) | QWSTRKR (SEQ ID NO: 63) | QSGDLTR (SEQ ID NO: 18) | NA |
| 30640 | QSSDLSR (SEQ ID NO: 31) | QWSTRKR (SEQ ID NO: 63) | QSSDLSR (SEQ ID NO: 31) | QWSTRKR (SEQ ID NO: 63) | QSGDLTR (SEQ ID NO: 18) | NA |

TABLE 1B-continued

Human and Mouse Htt-targeted zinc finger proteins

| SBS # | Design | | | | | |
|---|---|---|---|---|---|---|
| | F1 | F2 | F3 | F4 | F5 | F6 |
| 30657 | RSDTLSE (SEQ ID NO: 24) | RRWTLVG (SEQ ID NO: 64) | QSSDLSR (SEQ ID NO: 31) | HRSTRNR (SEQ ID NO: 32) | QSSDLSR (SEQ ID NO: 31) | HRSTRNR (SEQ ID NO: 32) |
| 30642 | QSGDLTR (SEQ ID NO: 18) | QSSDLSR (SEQ ID NO: 31) | QWSTRKR (SEQ ID NO: 63) | QSSDLSR (SEQ ID NO: 31) | QWSTRKR (SEQ ID NO: 63) | NA |
| 30646 | RSDNLSE (SEQ ID NO: 60) | KRCNLRC (SEQ ID NO: 61) | QSGDLTR (SEQ ID NO: 18) | QSSDLSR (SEQ ID NO: 31) | QWSTRKR (SEQ ID NO: 63) | NA |
| 32220 | RSDVLSE (SEQ ID NO: 42) | QSSDLSR (SEQ ID NO: 31) | HRSTRNR (SEQ ID NO: 32) | NA | NA | NA |
| 32210 | QSGDLTR (SEQ ID NO: 18) | QSSDLSR (SEQ ID NO: 31) | QWSTRKR (SEQ ID NO: 63) | NA | NA | NA |
| 32215 | RSDNLRE (SEQ ID NO: 65) | RSDNLSE (SEQ ID NO: 60) | KRCNLRC (SEQ ID NO: 61) | NA | NA | NA |
| 30658 | QSSDLSR (SEQ ID NO: 31) | HRSTRNR (SEQ ID NO: 32) | QSSDLSR (SEQ ID NO: 31) | HRSTRNR (SEQ ID NO: 32) | QSSDLSR (SEQ ID NO: 31) | NA |
| 32218 | QSSDLSR (SEQ ID NO: 31) | QSSDLSR (SEQ ID NO: 31) | NA | NA | NA | NA |
| 32427 | ERGTLAR (SEQ ID NO: 11) | TSGSLTR (SEQ ID NO: 10) | RSDNLAR (SEQ ID NO: 7) | DPSNRVG (SEQ ID NO: 78) | RSDDLSK (SEQ ID NO: 149) | DNSNRIK (SEQ ID NO: 150) |
| 32653 | RSDHLSE (SEQ ID NO: 29) | QSGHLSR (SEQ ID NO: 41) | RSDDLTR (SEQ ID NO: 3) | YRWLLRS (SEQ ID NO: 66) | QSSDLSR (SEQ ID NO: 31) | RKDALVA (SEQ ID NO: 67) |
| 32677 | QSGDLTR (SEQ ID NO: 18) | RRADLSR (SEQ ID NO: 68) | DRSHLTR (SEQ ID NO: 34) | DRSHLAR (SEQ ID NO: 13) | DRSNLSR (SEQ ID NO: 9) | LAQPRNK (SEQ ID NO: 69) |
| 33560 | ERGTLAR (SEQ ID NO: 11) | QSGSLTR (SEQ ID NO: 84) | RSDNLAR (SEQ ID NO: 7) | DDSHRKD (SEQ ID NO: 151) | RSDDLSK (SEQ ID NO: 149) | DNSNRIK (SEQ ID NO: 150) |
| 33583 | DRSNLSR (SEQ ID NO: 9) | HKQHRDA (SEQ ID NO: 76) | DRSDLSR (SEQ ID NO: 22) | RRTDLRR (SEQ ID NO: 77) | RSANLAR (SEQ ID NO: 73) | DRSHLAR (SEQ ID NO: 13) |
| 32685 | RSDHLSA (SEQ ID NO: 70) | RSADRTR (SEQ ID NO: 71) | RSDVLSE (SEQ ID NO: 42) | TSGHLSR (SEQ ID NO: 43) | RSDDLTR (SEQ ID NO: 3) | TSSDRKK (SEQ ID NO: 72) |
| 32422 | RSANLAR (SEQ ID NO: 73) | RSDDLTR (SEQ ID NO: 3) | RSDTLSE (SEQ ID NO: 24) | HHSARRC (SEQ ID NO: 74) | ERGTLAR (SEQ ID NO: 11) | DRSNLTR (SEQ ID NO: 35) |
| 32428 | RSDVLST (SEQ ID | DNSSRTR (SEQ ID | DRSNLSR (SEQ ID | HKQHRDA (SEQ ID | DRSDLSR (SEQ ID | RRTDLRR (SEQ ID |

TABLE 1B-continued

Human and Mouse Htt-targeted zinc finger proteins

| SBS # | Design | | | | | |
|---|---|---|---|---|---|---|
| | F1 | F2 | F3 | F4 | F5 | F6 |
| | NO: 19) | NO: 75) | NO: 9) | NO: 76) | NO: 22) | NO: 77) |
| 32430 | RSDVLST (SEQ ID NO: 19) | VRSRLRR (SEQ ID NO: 20) | ERGTLAR (SEQ ID NO: 11) | TSGSLTR (SEQ ID NO: 10) | RSDNLAR (SEQ ID NO: 7) | DPSNRVG (SEQ ID NO: 78) |
| 32432 | RSDVLST (SEQ ID NO: 19) | VRSRLRR (SEQ ID NO: 20) | ERGTLAR (SEQ ID NO: 11) | TSGSLTR (SEQ ID NO: 10) | RSDHLSA (SEQ ID NO: 70) | RSADLSR (SEQ ID NO: 79) |
| 32714 | RSDVLST (SEQ ID NO: 19) | DNSSRTR (SEQ ID NO: 75) | ERGTLAR (SEQ ID NO: 11) | QSGNLAR (SEQ ID NO: 47) | DRSHLTR (SEQ ID NO: 34) | RNDDRKK (SEQ ID NO: 80) |
| 32733 | DRSNLSR (SEQ ID NO: 9) | QKVTLAA (SEQ ID NO: 81) | RSAHLSR (SEQ ID NO: 46) | TSGNLTR (SEQ ID NO: 16) | DRSDLSR (SEQ ID NO: 22) | RRSTLRS (SEQ ID NO: 82) |
| 30901 | DRSALSR (SEQ ID NO: 83) | QSGSLTR (SEQ ID NO: 84) | QSSDLSR (SEQ ID NO: 31) | LKWNLRT (SEQ ID NO: 85) | RSDNLAR (SEQ ID NO: 7) | LKWDRQT (SEQ ID NO: 86) |
| 31952 | QSGALAR (SEQ ID NO: 147) | RSDDLTR (SEQ ID NO: 3) | DRSALSR (SEQ ID NO: 83) | RSDHLTQ (SEQ ID NO: 152) | QSGDLTR (SEQ ID NO: 18) | WSTSLRA (SEQ ID NO: 52) |
| 31921 | RSDSLLR (SEQ ID NO: 153) | RSDDLTR (SEQ ID NO: 3) | QSGDLTR (SEQ ID NO: 18) | RRDWLPQ (SEQ ID NO: 154) | DRSNLSR (SEQ ID NO: 9) | RSDDRKT (SEQ ID NO: 4) |
| 30906 | DRSHLSR (SEQ ID NO: 87) | TSGNLTR (SEQ ID NO: 16) | QSGDLTR (SEQ ID NO: 18) | DRSHLAR (SEQ ID NO: 13) | RSDVLST (SEQ ID NO: 19) | VRSRLRR (SEQ ID NO: 20) |

The sequence and location for the target sites of these proteins are disclosed in Tables 2A and 2B. Tables 2A and 2B show the target sequences for the indicated zinc finger proteins. Nucleotides in the target site that are contacted by the ZFP recognition helices are indicated in uppercase letters; non-contacted nucleotides indicated in lowercase.

TABLE 2A

Target sites on human and mouse Htt

| SBS # | Target Site |
|---|---|
| 18856 | AcGCTGCGCCGGCGGAGGCGgggccgcg (SEQ ID NO: 88) |
| 25920 | gcGCTCAGCAGGTGGTGaccttgtggac_ (SEQ ID NO: 103) |

TABLE 2A-continued

Target sites on human and mouse Htt

| SBS # | Target Site |
|---|---|
| 25921 | atGGTGGGAGAGACTGTgaggcggcagc_ (SEQ ID NO: 104) |
| 25923 | tgGGAGAGAcTGTGAGGCGgcagctggg (SEQ ID NO: 105) |
| 25922 | atGGCGCTCAGCAGGTGGTGaccttgtg_ (SEQ ID NO: 106) |

TABLE 2B

Target sites on human and mouse Htt

| SBS # | Target Site |
|---|---|
| 32468 | agCCGGCCGTGGACTCTGAGccgaggtg_ (SEQ ID NO: 89) |
| 32427 | cgCACTCGcCGCGAGgGTTGCCgggacg_ (SEQ ID NO: 155) |
| 32501 | gtGGCGATGCGGGGGGCGTGgtgaggta_ (SEQ ID NO: 90) |
| 31809 | acGCTGCGCCGGCGGAGGCGgggccgcg_ (SEQ ID NO: 88) |

TABLE 2B-continued

Target sites on human and mouse Htt

| SBS # | Target Site |
|---|---|
| 32528 | ccGGGACGGGTCCAaGATGGAcggccgc_ (SEQ ID NO: 91) |
| 30580 | agCCGGCCGTGGACTCTGAGccgaggtg_ (SEQ ID NO: 89) |
| 30929 | ccGTCCCGGCAGCCCCCacggcgccttg_ (SEQ ID NO: 92) |
| 30658 | ctGCTGCTGCTGCTGCTgctggaaggac_ (SE ID NO: 108) |
| 32538 | cgGGTCCAAGATGGACGGCCgctcaggt_ (SEQ ID NO: 93) |
| 32567 | ctGCTGCTGCTGGAAGGacttgagg_ (SEQ ID NO: 94) |
| 29627 | tcAGATGGGACGGCGCTGACctggctgg_ (SEQ ID NO: 95) |
| 29628 | ctGCCATGGACCTGAATGATgggaccca_ (SEQ ID NO: 96) |
| 29631 | gtGGTCTGGGAGCTGTCGCTgatgggcg_ (SEQ ID NO: 97) |
| 29632 | ccGAAGGGCCTGATtCAGCTGttacccc_ (SEQ ID NO: 98) |
| 29637 | aaCTTGCAAGTAACaGAAGACtcatcct_ (SEQ ID NO: 99) |
| 29638 | ctTGTACAGCTGTGAGGgtgagcataat_ (SEQ ID NO: 100) |
| 25917 | gcCATGGTGGGAGAGACtgtgaggcggc_ (SEQ ID NO: 101) |
| 25916 | ctCAGCAGGTGGTGACCttgtggacatt_ (SEQ ID NO: 102) |
| 33074 | agCAGCAGcaGCAGCAgCAGCAgcagca_ (SEQ ID NO: 157) |
| 33080 | caGCAGCAgCAGCAGcaGCAGCAgcagc_ (SEQ ID NO: 107) |
| 33084 | tgCTGCTGctGCTGCTgctgctggaagg_ (SEQ ID NO: 109) |
| 33088 | ctGCTGCTgCTGctGCTGCTgctggaag_ (SEQ ID NO: 158) |
| 30643 | caGCAGCAGCAGCAgCAGCAGcagcagc_ (SEQ ID NO: 107) |
| 30648 | agCAGCAGCAGCAGCAGCAGcagcagca_ (SEQ ID NO: 157) |
| 30645 | caGCAGCAGCAgCAGCAGcagcagcagc_ (SEQ ID NO: 107) |
| 30640 | caGCAGCAGCAGCAGCAgcagcagcagc_ (SEQ ID NO: 107) |
| 30657 | ctGCTGCTGCTGCTgCTGCTGgaaggac_ (SEQ ID NO: 108) |
| 30642 | caGCAGCAGCAGCAGCAgcagcagcagc_ (SEQ ID NO: 107) |
| 30646 | caGCAGCAGCAgCAGCAGcagcagcagc_ (SEQ ID NO: 107) |
| 32220 | ctGCTGCTgCTGctgctgctgctggaagg_ (SEQ ID NO: 208) |
| 32210 | caGCAGCAGCAgcagcagcagcagcagc_ (SEQ ID NO: 107) |
| 32215 | agCAGCAGCAGcagcagcagcagcagca (SEQ ID NO: 110) |
| 32218 | tGCTGCTgctgctgctgctgctggaagg (SEQ ID NO: 111) |
| 32653 | ggCTGGCTTTTGCGGGAAGGggcggggc_ (SEQ ID NO: 112) |
| 32677 | gaATTGACaGGCGGAtGCGTCGtcctct_ (SEQ ID NO: 113) |
| 33560 | cgCACTCGcCGCGAGgGTTGCCgggacg_ (SEQ ID NO: 155) |
| 33583 | gcGGCGAGtGCGTCCCGTGACgtcatgc_ (SEQ ID NO: 209) |
| 32685 | atTCTGCGGGTCTGGCGTGGcctcgtct_ (SEQ ID NO: 114) |
| 32422 | gtGACGTCATGCCGGCGGAGAcgaggcc_ (SEQ ID NO: 115) |
| 32428 | gtGCGTCCCGTGACGTCATGccggcgga_ (SEQ ID NO: 116) |
| 32430 | gcCGCGAGgGTTGCCGGGACGggcccaa_ (SEQ ID NO: 117) |
| 32432 | ccGCGAGGGTTGCCGGGACGggcccaag_ (SEQ ID NO: 118) |

TABLE 2B-continued

Target sites on human and mouse Htt

| SBS # | Target Site |
|---|---|
| 32714 | caTCGGGCagGAAGCCGTCATGgcaacc_ (SEQ ID NO: 119) |
| 32733 | tcCTGCCCGATGGGACAGACcctgaaga_ (SEQ ID NO: 120) |
| 30901 | gtACTGAGcAATGCTGTAGTCagcaatc_ (SEQ ID NO: 121) |
| 31952 | ccTGTCCAgAGGGTCGCGGTAcctccct_ (SEQ ID NO: 159) |
| 31921 | tgCCGGACCTGGCAGCGGCGgtggtggc_ (SEQ ID NO: 160) |
| 30906 | ccGGGACGGGTCCAaGATGGAcggccgc_ (SEQ ID NO: 91) |

In certain embodiments, the DNA-binding domain comprises a naturally occurring or engineered (non-naturally occurring) TAL effector (TALE) DNA binding domain. See, e.g., U.S. Patent Publication No. 2011/0301073, incorporated by reference in its entirety herein. The plant pathogenic bacteria of the genus *Xanthomonas* are known to cause many diseases in important crop plants. Pathogenicity of *Xanthomonas* depends on a conserved type III secretion (T3S) system which injects more than 25 different effector proteins into the plant cell. Among these injected proteins are transcription activator-like effectors (TALE) which mimic plant transcriptional activators and manipulate the plant transcriptome (see Kay, et al. (2007) *Science* 318:648-651). These proteins contain a DNA binding domain and a transcriptional activation domain. One of the most well characterized TALEs is AvrBs3 from *Xanthomonas campestgris* pv. *Vesicatoria* (see Bonas, et al. (1989) *Mol Gen Genet* 218:127-136 and International Patent Publication No. WO 2010/079430). TALEs contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack, et al. (2006) *J Plant Physiol* 163(3):256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer, et al. (2007) *Appl and Envir Micro* 73(13):4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*.

Specificity of these TALEs depends on the sequences found in the tandem repeats. The repeated sequence comprises approximately 102 bp and the repeats are typically 91-100% homologous with each other (Bonas, et al., ibid). Polymorphism of the repeats is usually located at positions 12 and 13 and there appears to be a one-to-one correspondence between the identity of the hypervariable diresidues at positions 12 and 13 with the identity of the contiguous nucleotides in the TALE's target sequence (see Moscou and Bogdanove (2009) *Science* 326:1501 and Boch, et al. (2009) *Science* 326:1509-1512). Experimentally, the code for DNA recognition of these TALEs has been determined such that an HD sequence at positions 12 and 13 leads to a binding to cytosine (C), NG binds to T, NI to A, C, G or T, NN binds to A or G, and IG binds to T. These DNA binding repeats have been assembled into proteins with new combinations and numbers of repeats, to make artificial transcription factors that are able to interact with new sequences and activate the expression of a non-endogenous reporter gene in plant cells (Boch, et al., ibid). Engineered TAL proteins have been linked to a Fok I cleavage half domain to yield a TAL effector domain nuclease fusion (TALEN) exhibiting activity in a yeast reporter assay (plasmid based target). See Christian, et al. (2010) *Genetics* epub 10.1534/genetics.110.120717. See, also, U.S. Patent Publication No. 2011/0301073, incorporated by reference in its entirety.

Specific examples of designed dimerization domains to be used with ZFPs or TALE proteins are listed in Table 3. The amino acid sequences of two types of domain, coiled-coil (CC) and dimerizing zinc finger (DZ) are listed.

TABLE 3

Designed dimerization domains

| Design name | Amino acid sequence |
|---|---|
| DZ1 | TKCVHCGIVFLDEVMYALHMSCHGFRDPFECNICGYHSQDRYEFSSHIVRG EH (SEQ ID NO: 122) <br> TKCVHCGIVFLDEVMYALHMSCHGFRDPFECNICGYHSQDRYEFSSHIVRG EH (SEQ ID NO: 122) |
| DZ2 | FKCEHCRILFLDHVMFTIHMGCHGFRDPFKCNMCGEKCDGPVGLFVHMARN AH (SEQ ID NO: 123) <br> TKCVHCGIVFLDEVMYALHMSCHGFRDPFECNICGYHSQDRYEFSSHIVRG EH (SEQ ID NO: 122) |
| DZ3 | FKCEHCRILFLDHVMFTIHMGCHGFRDPFKCNMCGEKCDGPVGLFVHMARN AH (SEQ ID NO: 123) |

TABLE 3-continued

Designed dimerization domains

| Design name | Amino acid sequence |
|---|---|
| | HHCQHCDMYFADNILYTIHMGCHGYENPFECNICGYHSQDRYEFSSHIVRG<br>EH (SEQ ID NO: 124) |
| DZ4 | HHCQHCDMYFADNILYTIHMGCHSCDDVFKCNMCGEKCDGPVGLFVHMARN<br>AHGEKPTKCVHCGIVFLDEVMYALHMSCHGFRDPFECNICGYHSQDRYEFS<br>SHIVRGEH (SEQ ID NO: 125)<br>FKCEHCRILFLDHVMFTIHMGCHGFRDPFKCNMCGEKCDGPVGLFVHMARN<br>AHGEKPFYCEHCEITFRDVVMYSLHKGYHGFRDPFECNICGYHSQDRYEFS<br>SHIVRGEH (SEQ ID NO: 126) |
| CC1 | AQLEKELQALEKKLAQLEWENQALEKELAQ (SEQ ID NO: 127)<br>AQLKKKLQANKKELAQLKWKLQALKKKLAQ (SEQ ID NO: 128) |
| CC2 | EQLEKKLQALEKKLAQLEWKNQALEKKLAQ (SEQ ID NO: 129)<br>ALKKELQANKKELAQLKWELQALKKELAQ (SEQ ID NO: 130) |
| CC3 | EQLEKKLQALEKKLAQLEWKNQALEK (SEQ ID NO: 131)<br>ELQANKKELAQLKWELQALKKELAQ (SEQ ID NO: 132) |
| CC4 | EQLEKKLQALEKKLAQLEWKNQA (SEQ ID NO: 133)<br>QANKKELAQLKWELQALKKELAQ (SEQ ID NO: 134) |
| CC5 | EQLEKKLQALEKKLAQLEWKNQALEKKLAQ (SEQ ID NO: 129)<br>ALKKELQANKKELAQLKWELQALKKELAQ (SEQ ID NO: 130) |
| CC6 | EQLEKKLQALEKKLAQLEWKNQALEKKLAQ (SEQ ID NO: 129)<br>ALKKELQANKKELAQLKWELQALKKELAQ (SEQ ID NO: 130) |
| CC7 | EQLEKKLQALEKKLAQLEWKNQALEKKLAQ (SEQ ID NO: 129)<br>ALKKELQANKKELAQLKWELQALKKELAQ (SEQ ID NO: 130) |

Fusion Proteins

Fusion proteins comprising DNA-binding proteins (e.g., ZFPs or TALEs) as described herein and a heterologous regulatory (functional) domain (or functional fragment thereof) are also provided. Common domains include, e.g., transcription factor domains (activators, repressors, co-activators, co-repressors), silencers, oncogenes (e.g., myc, jun, fos, myb, max, mad, rel, ets, bcl, myb, mos family members etc.); DNA repair enzymes and their associated factors and modifiers; DNA rearrangement enzymes and their associated factors and modifiers; chromatin associated proteins and their modifiers (e.g. kinases, acetylases and deacetylases); and DNA modifying enzymes (e.g., methyltransferases, topoisomerases, helicases, ligases, kinases, phosphatases, polymerases, endonucleases) and their associated factors and modifiers. U.S. Patent Publication Nos. 2005/0064474; 2006/0188987 and 2007/0218528 for details regarding fusions of DNA-binding domains and nuclease cleavage domains, incorporated by reference in their entireties herein.

Suitable domains for achieving activation include the HSV VP16 activation domain (see, e.g., Hagmann, et al. (1997) J. Virol. 71:5952-5962) nuclear hormone receptors (see, e.g., Torchia, et al. (1998) Curr. Opin. Cell. Biol. 10:373-383); the p65 subunit of nuclear factor kappa B (Bitko and Barik (1998) J. Virol. 72:5610-5618 and Doyle and Hunt (1997) Neuroreport 8:2937-2942; Liu, et al. (1998) Cancer Gene Ther. 5:3-28), or artificial chimeric functional domains such as VP64 (Beerli, et al. (1998) Proc. Natl. Acad. Sci. USA 95:14623-33), and degron (Molinari, et al. (1999) EMBO J. 18:6439-6447). Additional exemplary activation domains include, Oct 1, Oct-2A, Sp 1, AP-2, and CTF1 (Seipel, et al. (1992) EMBO J. 11:4961-4968 as well as p300, CBP, PCAF, SRC1 PvALF, AtHD2A and ERF-2. See, for example, Robyr, et al. (2000) Mol. Endocrinol. 14:329-347; Collingwood, et al. (1999) J. Mol. Endocrinol. 23:255-275; Leo, et al. (2000) Gene 245:1-11; Manteuffel-Cymborowska (1999) Acta Biochim. Pol. 46:77-89; McKenna, et al. (1999) J. Steroid Biochem. Mol. Biol. 69:3-12; Malik, et al. (2000) Trends Biochem. Sci. 25:277-283; and Lemon, et al. (1999) Curr. Opin. Genet. Dev. 9:499-504. Additional exemplary activation domains include, but are not limited to, OsGAI, HALF-1, C1, AP1, ARF-5, -6, -7, and -8, CPRF1, CPRF4, MYC-RP/GP, and TRAB1. See, for example, Ogawa, et al. (2000) Gene 245:21-29; Okanami, et al. (1996) Genes Cells 1:87-99; Goff, et al. (1991) Genes Dev. 5:298-309; Cho, et al. (1999) Plant Mol. Biol. 40:419-429; Ulmason, et al. (1999) Proc. Natl. Acad. Sci. USA 96:5844-5849; Sprenger-Haussels, et al. (2000) Plant J. 22:1-8; Gong, et al. (1999) Plant Mol. Biol. 41:33-44; and Hobo, et al. (1999) Proc. Natl. Acad. Sci. USA 96:15,348-15,353.

It will be clear to those of skill in the art that, in the formation of a fusion protein (or a nucleic acid encoding same) between a DNA-binding domain and a functional domain, either an activation domain or a molecule that interacts with an activation domain is suitable as a functional domain. Essentially any molecule capable of recruiting an activating complex and/or activating activity (such as, for example, histone acetylation) to the target gene is useful as an activating domain of a fusion protein. Insulator domains, localization domains, and chromatin remodeling proteins such as ISWI-containing domains and/or methyl binding domain proteins suitable for use as functional domains in fusion molecules are described, for example, in co-owned U.S. Patent Publication Nos. 2002/0115215 and 2003/0082552 and in co-owned International Patent Publication No. WO 02/44376.

Exemplary repression domains include, but are not limited to, KRAB A/B, KOX, TGF-beta-inducible early gene (TIEG), v-erbA, SID, MBD2, MBD3, members of the DNMT family (e.g., DNMT1, DNMT3A, DNMT3B), Rb, and MeCP2. See, for example, Bird, et al. (1999) *Cell* 99:451-454; Tyler, et al. (1999) *Cell* 99:443-446; Knoepfler, et al. (1999) *Cell* 99:447-450; and Robertson, et al. (2000) *Nature Genet.* 25:338-342. Additional exemplary repression domains include, but are not limited to, ROM2 and AtHD2A. See, for example, Chem, et al. (1996) *Plant Cell* 8:305-321; and Wu, et al. (2000) *Plant J.* 22:19-27.

Fusion molecules are constructed by methods of cloning and biochemical conjugation that are well known to those of skill in the art. Fusion molecules comprise a DNA-binding domain and a functional domain (e.g., a transcriptional activation or repression domain). Fusion molecules also optionally comprise nuclear localization signals (such as, for example, that from the SV40 medium T-antigen) and epitope tags (such as, for example, FLAG and hemagglutinin). Fusion proteins (and nucleic acids encoding them) are designed such that the translational reading frame is preserved among the components of the fusion.

Fusions between a polypeptide component of a functional domain (or a functional fragment thereof) on the one hand, and a non-protein DNA-binding domain (e.g., antibiotic, intercalator, minor groove binder, nucleic acid) on the other, are constructed by methods of biochemical conjugation known to those of skill in the art. See, for example, the Pierce Chemical Company (Rockford, Ill.) Catalogue. Methods and compositions for making fusions between a minor groove binder and a polypeptide have been described. Mapp, et al. (2000) *Proc. Natl. Acad. Sci. USA* 97:3930-3935.

In certain embodiments, the target site bound by the DNA binding domain is present in an accessible region of cellular chromatin. Accessible regions can be determined as described, for example, in co-owned International Patent Publication No. WO 01/83732. If the target site is not present in an accessible region of cellular chromatin, one or more accessible regions can be generated as described in co-owned International Patent Publication No. WO 01/83793. In additional embodiments, the DNA-binding domain of a fusion molecule is capable of binding to cellular chromatin regardless of whether its target site is in an accessible region or not. For example, such DNA-binding domains are capable of binding to linker DNA and/or nucleosomal DNA. Examples of this type of "pioneer" DNA binding domain are found in certain steroid receptor and in hepatocyte nuclear factor 3 (HNF3). Cordingley, et al. (1987) *Cell* 48:261-270; Pina, et al. (1990) *Cell* 60:719-731; and Cirillo, et al. (1998) *EMBO J.* 17:244-254.

The fusion molecule may be formulated with a pharmaceutically acceptable carrier, as is known to those of skill in the art. See, for example, Remington's Pharmaceutical Sciences, 17th ed., 1985; and co-owned International Patent Publication No. WO 00/42219.

The functional component/domain of a fusion molecule can be selected from any of a variety of different components capable of influencing transcription of a gene once the fusion molecule binds to a target sequence via its DNA binding domain. Hence, the functional component can include, but is not limited to, various transcription factor domains, such as activators, repressors, co-activators, co-repressors, and silencers.

Additional exemplary functional domains are disclosed, for example, in co-owned U.S. Pat. No. 6,534,261 and U.S. Patent Publication No. 2002/0160940.

Functional domains that are regulated by exogenous small molecules or ligands may also be selected. For example, RheoSwitch® technology may be employed wherein a functional domain only assumes its active conformation in the presence of the external RheoChem™ ligand (see for example U.S. Patent Publication No. 2009/0136465). Thus, the ZFP or TALE may be operably linked to the regulatable functional domain wherein the resultant activity of the ZFP-TF or TALE-TF is controlled by the external ligand.

Nucleases

In certain embodiments, the fusion protein comprises a DNA-binding binding domain and cleavage (nuclease) domain. As such, gene modification can be achieved using a nuclease, for example an engineered nuclease. Engineered nuclease technology is based on the engineering of naturally occurring DNA-binding proteins. For example, engineering of homing endonucleases with tailored DNA-binding specificities has been described. (see, Chames, et al. (2005) *Nucleic Acids Res* 33(20):e178; Arnould, et al. (2006) *J. Mol. Biol.* 355:443-458). In addition, engineering of ZFPs has also been described. See, e.g., U.S. Pat. Nos. 6,534,261; 6,607,882; 6,824,978; 6,979,539; 6,933,113; 7,163,824; and 7,013,219.

In addition, ZFPs and TALEs have been fused to nuclease domains to create ZFNs and TALENs—functional entities that are able to recognize their intended nucleic acid target through their engineered (ZFP or TALE) DNA binding domains and cause the DNA to be cut near the ZFP or TALE DNA binding site via the nuclease activity. See, e.g., Kim, et al. (1996) *Proc Natl Acad Sci USA* 93(3):1156-1160. More recently, ZFNs have been used for genome modification in a variety of organisms. See, for example, U.S. Patent Publication Nos. 2003/0232410; 2005/0208489; 2005/0026157; 2005/0064474; 2006/0188987; and 2006/0063231; and International Patent Publication No. WO 07/014275.

Thus, the methods and compositions described herein are broadly applicable and may involve any nuclease of interest. Non-limiting examples of nucleases include meganucleases, TALENs and zinc finger nucleases. The nuclease may comprise heterologous DNA-binding and cleavage domains (e.g., zinc finger nucleases; TALENs; meganuclease DNA-binding domains with heterologous cleavage domains) or, alternatively, the DNA-binding domain of a naturally-occurring nuclease may be altered to bind to a selected target site (e.g., a meganuclease that has been engineered to bind to site different than the cognate binding site).

In certain embodiments, the nuclease is a meganuclease (homing endonuclease). Naturally-occurring meganucleases recognize 15-40 base-pair cleavage sites and are commonly grouped into four families: the LAGLIDADG (SEQ ID NO: 250) family, the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. Nos. 5,420,032; 6,833,252; Belfort, et al. (1997) *Nucleic Acids Res.* 25:3379-3388; Dujon, et al. (1989) *Gene* 82:115-118; Perler, et al. (1994) *Nucleic Acids Res.* 22:1125-1127; Jasin (1996) *Trends Genet.* 12:224-228; Gimble, et al. (1996) *J. Mol. Biol.* 263:163-180; Argast, et al. (1998) *J. Mol. Biol.* 280:345-353 and the New England Biolabs catalogue.

DNA-binding domains from naturally-occurring meganucleases, primarily from the LAGLIDADG (SEQ ID NO: 250) family, have been used to promote site-specific genome modification in plants, yeast, Drosophila, mammalian cells and mice, but this approach has been limited to the modification of either homologous genes that conserve the meganuclease recognition sequence (Monet, et al. (1999) *Biochem. Biophysics. Res. Common.* 255:88-93) or to pre-engineered genomes into which a recognition sequence has been introduced (Route, et al. (1994) *Mol. Cell. Biol.* 14:8096-106; Chilton, et al. (2003) *Plant Physiology* 133:956-65; Puchta, et al. (1996) *Proc. Natl. Acad. Sci. USA* 93:5055-60; Rong, et al. (2002) *Genes Dev.* 16:1568-81; Gouble, et al. (2006) *J. Gene Med.* 8(5):616-622). Accordingly, attempts have been made to engineer meganucleases to exhibit novel binding specificity at medically or biotechnologically relevant sites (Porteus, et al. (2005) *Nat. Biotechnol.* 23:967-73; Sussman, et al. (2004) *J. Mol. Biol.* 342:31-41; Epinat, et al. (2003) *Nucleic Acids Res.* 31:2952-62; Chevalier, et al. (2002) *Molec. Cell* 10:895-905; Epinat, et al. (2003) *Nucleic Acids Res.* 31:2952-2962; Ashworth, et al. (2006) *Nature* 441:656-659; Nques, et al. (2007) *Current Gene Therapy* 7:49-66; U.S. Patent Publication Nos. 2007/0117128; 2006/0206949; 2006/0153826; 2006/0078552; and 2004/0002092). In addition, naturally-occurring or engineered DNA-binding domains from meganucleases have also been operably linked with a cleavage domain from a heterologous nuclease (e.g., Fok I).

In other embodiments, the nuclease is a zinc finger nuclease (ZFN). ZFNs comprise a zinc finger protein that has been engineered to bind to a target site in a gene of choice and cleavage domain or a cleavage half-domain.

As described in detail above, zinc finger binding domains can be engineered to bind to a sequence of choice. See, for example, Beerli, et al. (2002) *Nature Biotechnol.* 20:135-141; Pabo, et al. (2001) *Ann. Rev. Biochem.* 70:313-340; Isalan, et al. (2001) *Nature Biotechnol.* 19:656-660; Segal, et al. (2001) *Curr. Opin. Biotechnol.* 12:632-637; Choo, et al. (2000) *Curr. Opin. Struct. Biol.* 10:411-416. An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as International Patent Publication Nos. WO 98/37186; WO 98/53057; WO 00/27878; and WO 01/88197 and GB 2,338,237. In addition, enhancement of binding specificity for zinc finger binding domains has been described, for example, in co-owned International Patent Publication No. WO 02/077227.

In addition, as disclosed in these and other references, zinc finger domains and/or multi-fingered zinc finger proteins may be linked together using any suitable linker sequences, including for example, linkers of 5 or more amino acids in length (e.g., TGEKP (SEQ ID NO:135), TGGQRP (SEQ ID NO:136), TGQKP (SEQ ID NO:137), and/or TGSQKP (SEQ ID NO:138)). See, e.g., U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. See, also, U.S. Patent Publication No. 2011/0287512.

The CRISPR (Clustered Regularly Interspaced Short Palindromic Repeats)/Cas (CRISPR Associated) nuclease system is a recently engineered nuclease system based on a bacterial system that can be used for genome engineering. It is based on part of the adaptive immune response of many bacteria and archea. When a virus or plasmid invades a bacterium, segments of the invader's DNA are converted into CRISPR RNAs (crRNA) by the 'immune' response. This crRNA then associates, through a region of partial complementarity, with another type of RNA called tracrRNA to guide the Cas9 nuclease to a region homologous to the crRNA in the target DNA called a "protospacer." Cas9 cleaves the DNA to generate blunt ends at the DSB at sites specified by a 20-nucleotide guide sequence contained within the crRNA transcript. Cas9 requires both the crRNA and the tracrRNA for site specific DNA recognition and cleavage. This system has now been engineered such that the crRNA and tracrRNA can be combined into one molecule (the "single guide RNA"), and the crRNA equivalent portion of the single guide RNA can be engineered to guide the Cas9 nuclease to target any desired sequence (see Jinek, et al. (2012) *Science* 337:816-821; Jinek, et al. (2013) *eLife* 2:e00471, and Segal (2013) *eLife* 2:e00563). Thus, the CRISPR/Cas system can be engineered to create a DSB at a desired target in a genome, and repair of the DSB can be influenced by the use of repair inhibitors to cause an increase in error prone repair.

Nucleases such as ZFNs, TALENs and/or meganucleases also comprise a nuclease (cleavage domain, cleavage half-domain). As noted above, the cleavage domain may be heterologous to the DNA-binding domain, for example a zinc finger DNA-binding domain and a cleavage domain from a nuclease or a meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort, et al. (1997) *Nucleic Acids Res.* 25:3379-3388. Additional enzymes which cleave DNA are known (e.g., 51 Nuclease; mung bean nuclease; pancreatic DNase I; micrococcal nuclease; yeast HO endonuclease; see also Linn, et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150; and 5,487,994; as well as Li, et al. (1992) *Proc. Natl. Acad. Sci. USA* 89:4275-4279; Li, et al. (1993) *Proc. Natl. Acad. Sci. USA* 90:2764-2768; Kim, et al. (1994a) *Proc. Natl. Acad. Sci. USA* 91:883-887; Kim, et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite, et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger- or TALE-Fok I fusions, two fusion proteins, each comprising a Fok I cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger- or TALE-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Patent Publication No. WO 07/014275, incorporated herein in its entirety. Additional restriction enzymes also contain separable binding and cleavage domains, and these are contemplated by the present disclosure. See, for example, Roberts, et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 2005/0064474; 2006/0188987; and 2008/0131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains. Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. See, e.g., U.S. Patent Publication Nos. 2008/0131962 and 2011/0201055, the disclosure of which is incorporated by reference in its entirety for all purposes. In certain embodiments, the engineered cleavage half-domain comprises mutations at positions 486, 499 and 496 (numbered relative to wild-type Fok I), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type Fok I), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KIK" and "KIR" domains, respectively). In other embodiments, the engineered cleavage half-domain comprises mutations at positions 490 and 537 (numbered relative to wild-type Fok I), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See U.S. Patent Publication No. 2011/0201055).

Engineered cleavage half-domains described herein can be prepared using any suitable method, for example, by site-directed mutagenesis of wild-type cleavage half-domains (Fok I) as described in U.S. Patent Publication Nos. 2005/0064474 and 2008/0131962.

Alternatively, nucleases may be assembled in vivo at the nucleic acid target site using so-called "split-enzyme" technology (see e.g. U.S. Patent Publication No. 2009/0068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

In some embodiments, the DNA binding domain is an engineered domain from a TAL effector similar to those derived from the plant pathogens *Xanthomonas* (see Boch, et al. (2009) *Science* 326:1509-1512 and Moscou and Bogdanove (2009) *Science* 326:1501) and *Ralstonia* (see Heuer, et al. (2007) *Applied and Environmental Microbiology* 73(13):4379-4384). Also, see International Patent Publication No. WO2010/079430.

Nucleases (e.g., ZFNs or TALENs) can be screened for activity prior to use, for example in a yeast-based chromosomal system as described in International Patent Publication No. WO 2009/042163 and U.S. Patent Publication No. 2009/0068164. Nuclease expression constructs can be readily designed using methods known in the art. See, e.g., U.S. Patent Publication Nos. 2003/0232410; 2005/0208489; 2005/0026157; 2005/0064474; 2006/0188987; 2006/0063231; and International Patent Publication No. WO 07/014275. Expression of the nuclease may be under the control of a constitutive promoter or an inducible promoter, for example the galactokinase promoter which is activated (de-repressed) in the presence of raffinose and/or galactose and repressed in presence of glucose.

Delivery

The proteins (e.g., ZFPs, TALEs, CRISPR/Cas), polynucleotides encoding same and compositions comprising the proteins and/or polynucleotides described herein may be delivered to a target cell by any suitable means including, for example, by injection of ZFP-TF, TALE-TF proteins or by use of ZFN or TALEN encoding mRNA. Suitable cells include but not limited to eukaryotic and prokaryotic cells and/or cell lines. Non-limiting examples of such cells or cell lines generated from such cells include COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), and perC6 cells as well as insect cells such as *Spodoptera fugiperda* (Sf), or fungal cells such as *Saccharomyces, Pichia* and *Schizosaccharomyces*. In certain embodiments, the cell line is a CHO-K1, MDCK or HEK293 cell line. Suitable cells also include stem cells such as, by way of example, embryonic stem cells, induced pluripotent stem cells, hematopoietic stem cells, neuronal stem cells and mesenchymal stem cells.

Methods of delivering proteins comprising zinc finger proteins as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Zinc finger, TALE or CRISPR/Cas proteins as described herein may also be delivered using vectors containing sequences encoding one or more of the zinc finger, TALE or CRISPR/Cas protein(s). Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more zinc finger or TALE protein-encoding sequences. Thus, when one or more ZFPs, TALEs or CRISPR/Cas proteins are introduced into the cell, the sequences encoding the ZFPs, TALEs or CRISPR/Cas proteins may be carried on the same vector or on different vectors. When multiple vectors are used, each vector may comprise a sequence encoding one or multiple ZFPs, TALEs or CRISPR/Cas systems.

Conventional viral and non-viral based gene transfer methods can be used to introduce nucleic acids encoding engineered ZFPs, TALEs or CRISPR/Cas systems in cells (e.g., mammalian cells) and target tissues. Such methods can also be used to administer nucleic acids encoding ZFPs, TALEs or a CRISPR/Cas system to cells in vitro. In certain embodiments, nucleic acids encoding the ZFPs, TALEs or CRISPR/Cas system are administered for in vivo or ex vivo gene therapy uses. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson (1992) *Science* 256:808-813; Nabel and Felgner (1993) *TIBTECH* 11:211-217; Mitani and Caskey (1993) *TIBTECH* 11:162-166; Dillon (1993) *TIBTECH* 11:167-175; Miller (1992) *Nature* 357:455-460; Van Brunt (1988) *Biotechnology* 6(10):1149-1154; Vigne (1995) *Restorative Neurology and Neuroscience* 8:35-36; Kremer and Perricaudet (1995) *British Medical Bulletin* 51(1):31-44; Haddada, et al., in *Current Topics in Microbiology and Immunology* Doerfler and Bohm (eds.) (1995); and Yu, et al. (1994) *Gene Therapy* 1:13-26.

Methods of non-viral delivery of nucleic acids include electroporation, lipofection, microinjection, biolistics, virosomes, liposomes, immunoliposomes, polycation or lipid:nucleic acid conjugates, naked DNA, naked RNA, artificial virions, and agent-enhanced uptake of DNA. Sonoporation using, e.g., the Sonitron 2000 system (Rich-Mar) can also be used for delivery of nucleic acids. In a preferred embodiment, one or more nucleic acids are delivered as mRNA. Also preferred is the use of capped mRNAs to increase translational efficiency and/or mRNA stability. Especially preferred are ARCA (anti-reverse cap analog) caps or variants thereof. See U.S. Pat. Nos. 7,074,596 and 8,153,773, incorporated by reference herein.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™ and Lipofectamine™ RNAiMAX). Cationic and neutral lipids that are suitable for efficient receptor-recognition lipofection of polynucleotides include those of Felgner, International Patent Publication Nos. WO 91/17424 and WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal (1995) *Science* 270:404-410 (1995); Blaese, et al. (1995) *Cancer Gene Ther.* 2:291-297; Behr, et al. (1994) *Bioconjugate Chem.* 5:382-389; Remy, et al. (1994) *Bioconjugate Chem.* 5:647-654; Gao, et al. (1995) *Gene Therapy* 2:710-722; Ahmad, et al. (1992) *Cancer Res.* 52:4817-4820; U.S. Pat. Nos. 4,186,183; 4,217,344; 4,235,871; 4,261,975; 4,485,054; 4,501,728; 4,774,085; 4,837,028; and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid, et al. (2009) *Nature Biotechnology* 27(7):643).

The use of RNA or DNA viral based systems for the delivery of nucleic acids encoding engineered ZFPs, TALEs or CRISPR/Cas systems take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs, TALEs or CRISPR/Cas systems include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon mouse leukemia virus (MuLV), gibbon ape leukemia virus (GaLV), Simian Immunodeficiency virus (SIV), human immunodeficiency virus (HIV), and combinations thereof (see, e.g., Buchscher, et al. (1992) *J. Virol.* 66:2731-2739; Johann, et al. (1992) *J. Virol.* 66:1635-1640; Sommerfelt, et al. (1990) *Virol.* 176: 58-59; Wilson, et al. (1989) *J. Virol.* 63:2374-2378; Miller, et al. (1991) *J. Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West, et al. (1987) *Virology* 160:38-47; U.S. Pat. No. 4,797,368; International Patent Publication No. WO 93/24641; Kotin (1994) *Human Gene Therapy* 5:793-801; Muzyczka (1994) *J. Clin. Invest.* 94:1351. Construction of recombinant AAV vectors are described in a number of publications, including U.S. Pat. No. 5,173,414; Tratschin, et al. (1985) *Mol. Cell. Biol.* 5:3251-3260; Tratschin, et al. (1984) *Mol. Cell. Biol.* 4:2072-2081; Hermonat and Muzyczka (1984) *PNAS* 81:6466-6470; and Samulski, et al. (1989) *J. Virol.* 63:3822-3828.

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar, et al. (1995) *Blood* 85:3048-305; Kohn, et al. (1995) *Nat. Med.* 1:1017-102; Malech, et al. (1997) *PNAS* 94(22):12133-12138). PA317/pLASN was the first therapeutic vector used in a gene therapy trial. (Blaese, et al. (1995) *Science* 270:475-480). Transduction efficiencies of 50% or greater have been observed for MFG-S packaged vectors. (Ellem, et al. (1997) *Immunol Immunother* 44(1):10-20; Dranoff, et al. (1997) *Hum. Gene Ther.* 1:111-112.

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner, et al. (1998) *Lancet* 351(9117): 1702-1703; Kearns, et al. (1996) *Gene Ther.* 9:748-55). Other AAV serotypes, including AAV1, AAV3, AAV4, AAV5, AAV6, AAV8AAV 8.2, AAV9, and AAV rh10 and pseudotyped AAV such as AAV2/8, AAV2/5 and AAV2/6 can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman, et al. (1998) *Hum. Gene Ther.* 7:1083-1089). Additional examples of the use of adenovirus vectors for gene transfer in clinical trials include Rosenecker, et al. (1996) *Infection* 24(1):5-10; Sterman, et al. (1998) *Hum. Gene Ther.* 9(7):1083-1089; Welsh, et al. (1995) *Hum. Gene Ther.* 2:205-218; Alvarez, et al. (1997) *Hum. Gene Ther.* 5:597-613; Topf, et al. (1998) *Gene Ther.* 5:507-513; Sterman, et al. (1998) *Hum. Gene Ther.* 7:1083-1089.

Packaging cells are used to form virus particles that are capable of infecting a host cell. Such cells include 293 cells, which package adenovirus, and $\psi$2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han, et al. (1995) *Proc. Natl. Acad. Sci. USA* 92:9747-9751, reported that Moloney mouse leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a ZFP, TALE or CRISPR/Cas system nucleic acid (gene. cDNA or mRNA), and re-infused back into the subject organism (e.g., patient). In a preferred embodiment, one or more nucleic acids are delivered as mRNA. Also preferred is the use of capped mRNAs to increase translational efficiency and/or mRNA stability. Especially preferred are ARCA (anti-reverse cap analog) caps or variants thereof. See U.S. Pat. Nos. 7,074,596 and 8,153,773, incorporated by reference herein in their entireties. Various cell types suitable for ex vivo transfection are well known to those of skill in the art (see, e.g., Freshney, et al., *Culture of Animal Cells, A Manual of Basic Technique* (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see Inaba, et al. (1992) *J. Exp. Med.* 176:1693-1702).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panB cells), GR-1 (granulocytes), and Tad (differentiated antigen presenting cells) (see Inaba, et al. (1992) *J. Exp. Med.* 176:1693-1702).

Stem cells that have been modified may also be used in some embodiments. For example, neuronal stem cells that have been made resistant to apoptosis may be used as therapeutic compositions where the stem cells also contain the ZFP TFs of the invention. Resistance to apoptosis may come about, for example, by knocking out BAX and/or BAK using BAX- or BAK-specific TALENs or ZFNs (see, U.S. Patent Publication No. 2010/0003756) in the stem cells, or those that are disrupted in a caspase, again using caspase-6 specific ZFNs for example. These cells can be transfected with the ZFP TFs or TALE TFs that are known to regulate mutant or wild-type Htt.

Vectors (e.g., retroviruses, adenoviruses, liposomes, etc.) containing therapeutic ZFP nucleic acids can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Methods for introduction of DNA into hematopoietic stem cells are disclosed, for example, in U.S. Pat. No. 5,928,638. Vectors useful for introduction of transgenes into hematopoietic stem cells, e.g., CD34+ cells, include adenovirus Type 35.

Vectors suitable for introduction of transgenes into immune cells (e.g., T-cells) include non-integrating lentivirus vectors. See, for example, Ory, et al. (1996) *Proc. Natl. Acad. Sci. USA* 93:11382-11388; Dull, et al. (1998) *J. Virol.* 72:8463-8471; Zuffery, et al. (1998) *J. Virol.* 72:9873-9880; Follenzi, et al. (2000) *Nature Genetics* 25:217-222.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences,* 17th ed., 1989).

As noted above, the disclosed methods and compositions can be used in any type of cell including, but not limited to, prokaryotic cells, fungal cells, Archaeal cells, plant cells, insect cells, animal cells, vertebrate cells, mammalian cells and human cells. Suitable cell lines for protein expression are known to those of skill in the art and include, but are not limited to COS, CHO (e.g., CHO-S, CHO-K1, CHO-DG44, CHO-DUXB11), VERO, MDCK, W138, V79, B14AF28-G3, BHK, HaK, NS0, SP2/0-Ag14, HeLa, HEK293 (e.g., HEK293-F, HEK293-H, HEK293-T), perC6, insect cells such as *Spodoptera fugiperda* (Sf), and fungal cells such as *Saccharomyces, Pischia* and *Schizosaccharomyces.* Progeny, variants and derivatives of these cell lines can also be used.

Applications

The disclosed compositions and methods can be used for any application in which it is desired to modulate the Htt allele, including but not limited to, therapeutic and research applications.

Diseases and conditions which Htt repressing ZFP TFs or TALE TFs can be used as therapeutic agents include, but are not limited to, Huntington's disease. Additionally, methods and compositions comprising ZFNs or TALENs specific for mutant alleles of Htt can be used as a therapeutic for the treatment of Huntington's disease.

ZFP-TFs or TALE TFs that repress a HD Htt allele may also be used in conjunction with ZFP-TFs or TALE-TFs that activate neutrotrophic factors including, but not limited to, GDNF and BDNF. These ZFPs or TALEs (or polynucleotides encoding these ZFPs or TALEs) may be administered concurrently (e.g., in the same pharmaceutical compositions) or may be administered sequentially in any order.

Methods and compositions for the treatment of Huntington's disease also include stem cell compositions wherein a mutant copy of the Htt allele within the stem cells has been modified to a wild-type Htt allele using a Htt-specific ZFN or TALEN.

The methods and compositions of the invention are also useful for the design and implementation of in vitro and in vivo models, for example, animal models of trinucleotide repeate disorders, which allows for the study of these disorders. Non-limiting examples of suitable in vitro models include cells or cell lines from any organism, including fibroblasts. Non-limiting examples of suitable animals for use as animal models include, invertebrates (*C. elegans, drosophila*), rodents (e.g., rat or mouse), primates (e.g., non-human primates).

EXAMPLES

Example 1: Design and Construction of Htt-Targeted Zinc Finger Protein Transcription Factors (ZFP-TFs) and ZFNs Zinc finger proteins targeted to Htt were engineered essentially as described in U.S. Pat. No. 6,534,261. Tables 1A and 1B show the recognition helices of the DNA binding domain of exemplary Htt-targeted ZFPs, while Tables 2A and 2B show the target sequences of these ZFPs.

ZFPs with one contiguous array of zinc fingers were designed to target sites completely within the CAG repeat region (FIG. 1B). Such ZFPs may bind longer, mutant tracts with higher affinity and/or a higher net occupancy, achieving selective repression of the mutant allele. ZFNs were also designed that targeted sites which lay partially or wholly outside of the CAG region (FIG. 1A), and which will therefore bind to the wild type and mutant allele equally, and regulate expression from both alleles with similar efficiency. When designing zinc finger proteins to recognize the CAG region, a set of one- and two-finger modules can be employed in a 'mix and match' combination. Those modules are shown below in Table 2C.

TABLE 2C

Zinc finger recognition helices used in ZFP-TFs targeting CAG repeats

| Target site | F2 | F3 | SEQ ID NO: (F2 + F3) |
|---|---|---|---|
| CAGCAG | RSDNLSE | KRCNLRC | 161 |
| CAGCAG | RSDNLSE | KPYNLRT | 162 |
| CAGCAG | RSDNLSE | RLWNRKQ | 163 |
| CAGCAG | RSDNLSV | RRWNLRA | 164 |
| CAGCAG | RSDNLSV | RKWNRDS | 165 |
| CAGCAG | RSDNLSE | NTSPLML | 166 |
| CAGCAG | RSDNLSE | RRYNLVK | 167 |

TABLE 2C-continued

Zinc finger recognition helices used in ZFP-TFs targeting CAG repeats

| Target site | F2 | F3 | SEQ ID NO: (F2 + F3) |
|---|---|---|---|
| CTGCTG | RSDTLSE | RRWTLVG | 168 |
| GCAGCA | QSSDLSR | QWSTRKR | 169 |
| GCAGCA | RSAHLSR | QSGDLTR | 170 |
| GCAGCA | QSGDLTR | QSGDLTR | 171 |
| GCAGCA | QSGDLTR | QSSDLRR | 172 |
| GCTGCT | QSSDLSR | QSSDLRR | 173 |
| GCTGCT | QSSDLSR | HRSTRNR | 174 |
| AGC | MACCRYA | none | 175 |
| CAG | RSANLRE | none | 176 |
| CAG | RNADRKK | none | 177 |
| CTG | RSDVLSE | none | 42 |
| CTG | RSAVLSE | none | 148 |
| GCA | QSGDLTR | none | 18 |
| GCA | QSSDLRR | none | 6 |
| GCA | QNATRIK | none | 178 |
| GCT | QSSDLSR | none | 31 |
| AG | RSDNLRE | none | 65 |

Multimerizing ZFP TFs are also constructed as described above except that the vector also contains sequences encoding 1 or more protein interaction domains (also called dimerization or protein interaction domains) that enable multimerization of the expressed protein along a tract of trinucleotide repeats that is operably linked to the sequences encoding the ZFP TF. See, FIG. 1D and FIG. 10. Table 3 shows dimerization domain designs that are used with ZFPs targeted to the CAG repeat region. FIG. 10C shows protein sequences of the four ZFP monomer scaffolds that are designed to multimerize via interactions between dimerizing zinc fingers (DZ), DZ1-DZ4. Designs are based on work described in Gisecke, et al. (2006) *Mol. Syst. Biol.* 2:2006-2011. FIG. 10D shows protein sequences of the seven ZFP monomer scaffolds that are designed to multimerize via interactions between coiled-coils (CC), CC1-CC7. The design of CC #1 is based on the work described in (McClain, et al. (2001) *J. Am. Chem. Soc.* 123:3151-3152), while CC #2, CC #3 and CC #4 are based on (Ghosh, et al. (2000) *J. Am. Chem. Soc.* 122:5658-5659). CC and DZ domains allow the ZFP to polymerize within the major groove of a CAG tract (depicted in FIG. 10B). By choosing a finger array and dimerization domains with appropriate binding properties, efficient binding will occur only to the expanded CAG tract of a disease allele.

ZFP-TFs were constructed as fusion proteins comprising a nuclear localization sequence, the engineered zinc finger DNA-binding domain (Tables 1A and 1B), targeted to the Htt allele, and a KRAB repression domain from the human KOX1 protein. See, FIGS. 1A, 1B and 1D. The designed DNA-binding domains contain 3-6 finger modules, recognizing 9-18 bp sequences (Tables 2A and 2B). Nucleotides in the target site that are contacted by the ZFP recognition helices are indicated in uppercase letters; non-contacted nucleotides indicated in lowercase. ZFP-ZFP-TF molecules were also constructed where two ZFP DNA binding domains were fused with a flexible linker and fused to a KRAB repression domain (FIG. 1E). DNA binding domains were chosen from Tables 2A and 2B.

Example 2: Repression of Both Alleles of Htt in Human and Mouse Cells

To repress both alleles of the Htt (non-allele-specific), ZFPs were designed to bind to the Htt promoter and exon 1 region, wherein the target site was not entirely within the CAG repeat. See, FIG. 1A. To test the activity of the Htt repressing ZFP TFs, the ZFP TFs were transfected into human cells and expression of Htt was monitored using real-time RT-PCR.

Human HEK293 cells (Graham, et al. (1977) *J Gen Virol* 36:59-74) were cultured in DMEM supplemented with 10% FBS and $1e^5$ cells were transfected with 1 μg of plasmid DNA encoding indicated ZFP-KOX fusions by Amaxa Nucleofector® following the manufacturer's instructions.

Transfected cells were incubated for 2 days, and the levels of endogenous human Huntingtin (Htt) and normalization control beta-actin (ACTB) were analyzed by real-time PCR using Hs00918176_m1 and 4352935E primers and probes (Applied Biosystems), respectively, according to standard protocols. Htt levels were expressed as Htt/ACTB ratios normalized to that of the mock-transfected samples (set as 1).

As shown in FIG. 2A, Htt-targeted ZFPs repressed Htt expression. Western blot analyses were done using standard protocols to confirm the reduction in Htt protein level (FIG. 2B); p65 protein was used as loading control.

Mouse Htt-specific ZFP TFs repressors were transiently transfected into Neuro2A cells (Klebe and Ruddle (1969) *J. Cell Biol.* 43:69A) using the Lipofectamine® 2000 kit (Invitrogen) according to manufacturer's protocols. mHtt and ACTB mRNA levels were measured at 48 hours after transfection using ABI Taqman® primer/probe set Mm01213820 m1 and 4352933E, respectively. mHtt/ACTB ratios for ZFP transfected samples were normalized to that of the GFP control (set as 1).

Figure 2C:
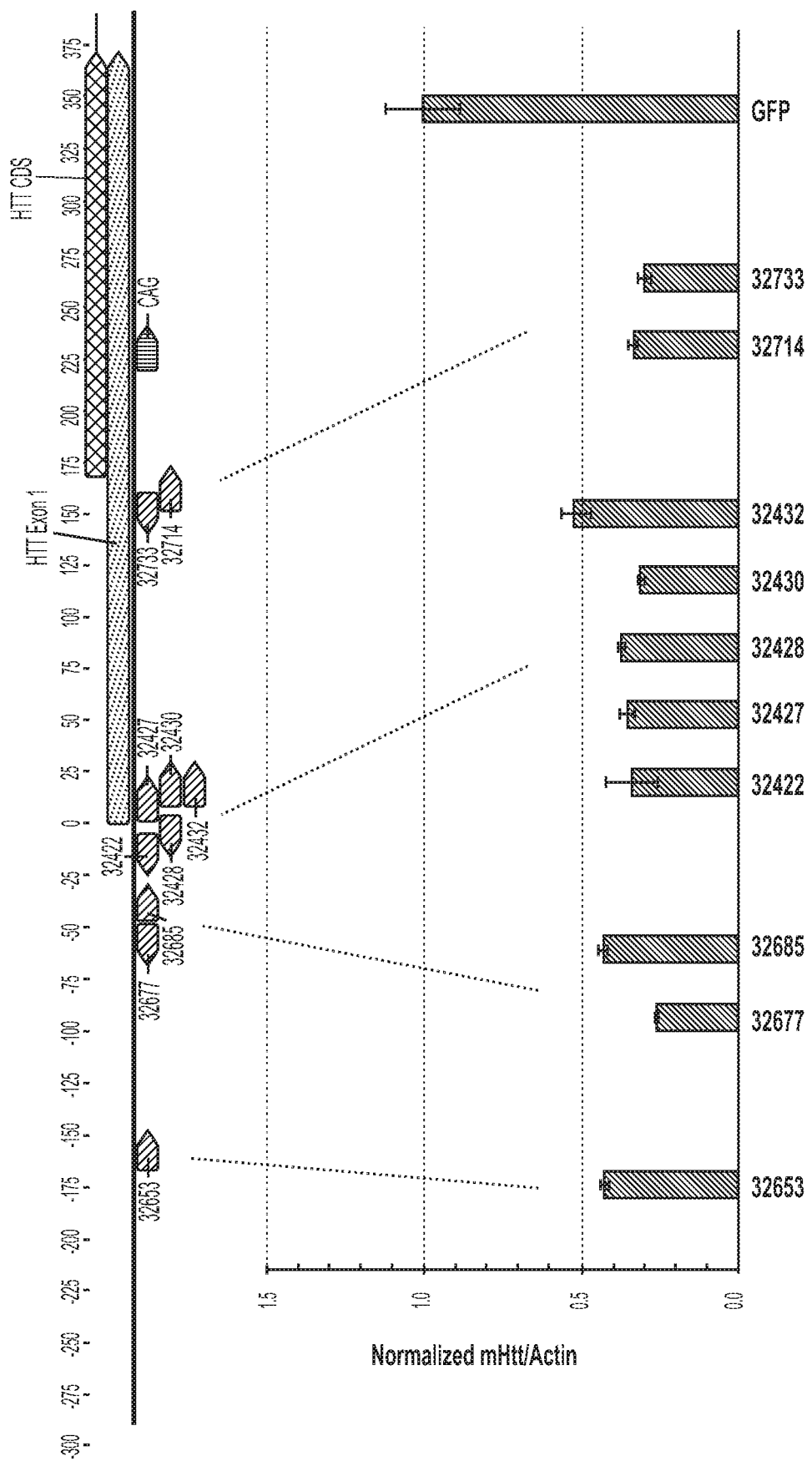
Figure 2D:
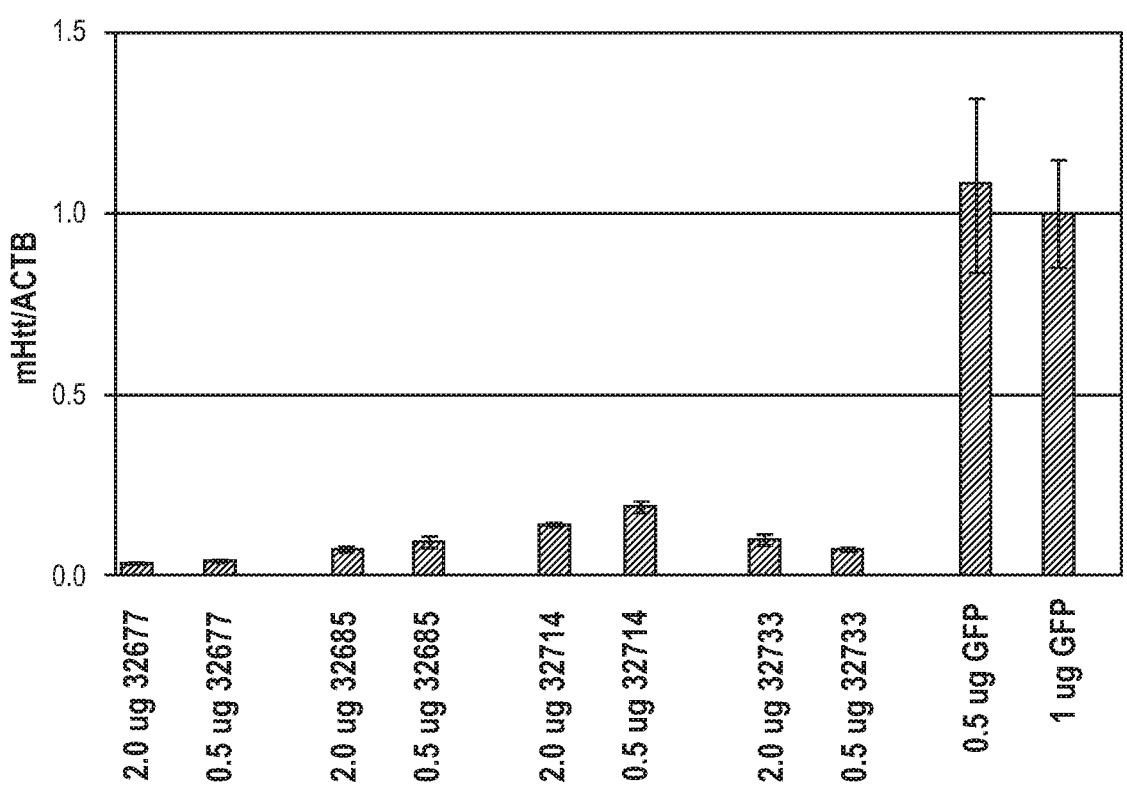
Figure 2E:
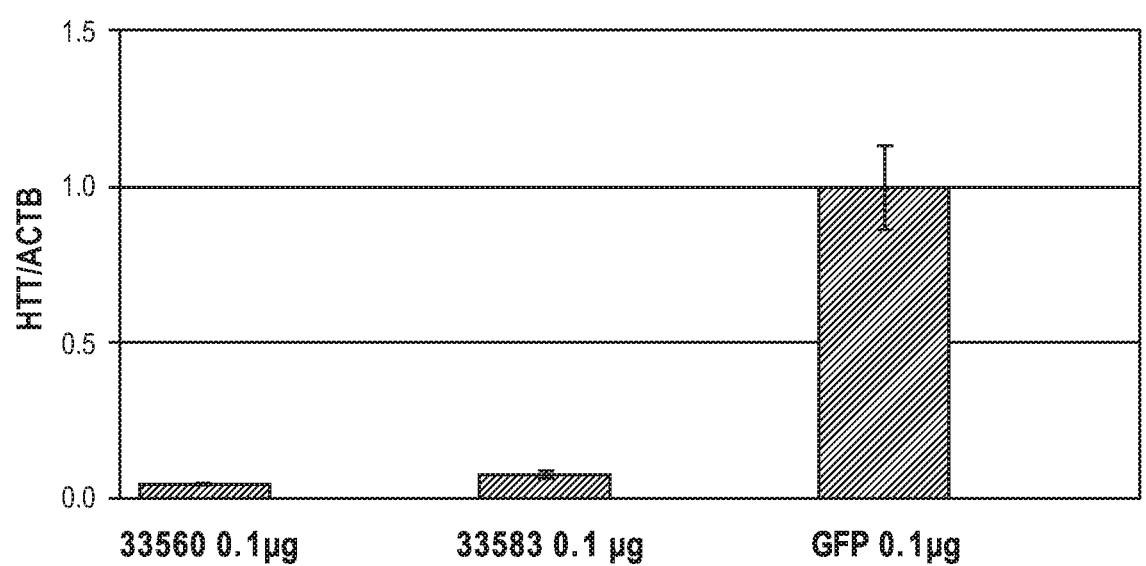

As shown in FIG. 2C, the ZFPs repressed mouse Htt expression. In addition, mouse Htt-specific ZFP-TF repressors can repress mouse Htt in immortalized striatal cells, STHdh(Q111/Q7), derived from Htt knock-in mice (Trettel, et al. (2000) *Hum. Mol. Genet* 9:2799-2809). See, FIGS. 2D and 2E. mRNA for indicated ZFPs were generated using the mMessage mMachine kit (Ambion), and 0.1, 0.5 or 2 ug of these mRNAs were transfected using Amaxa nucleofector as described above. Cells were harvested 48 hours after transfection for mHtt and ACTB expression analysis as described above. More significant repression in the striatal cells compared to that in Neuro2A cells was observed and may be a result of enhanced transfection efficiency achieved via mRNA transfection in straital cells.

Example 3: Selective Repression of Mutant Htt in Human and Mouse Cells

To achieve selective repression of the mutant Htt allele, ZFPs were designed to bind within the CAG repeat. FIG. 1B shows one type of such ZFPs, with a contiguous array of zinc fingers linked to a repression domain (e.g. the KRAB domain from KOX1); these ZFPs can be designed with appropriate affinity such that threshold occupancy required from transcriptional repression can only be established on expanded CAG repeats. FIGS. 1C, 1D and 1E show three other examples of ZFP design that can allow specific binding to the expanded CAG repeats.

ZFPs designed as illustrated in FIG. 1B were introduced into HEK293 cells and Htt expression evaluated. ZFP-encoding constructs were transfected into HEK293 cells using FugeneHD using standard protocols. Seventy-two hours after transfection total RNA was isolated and the levels of endogenous human Huntingtin (Htt) relative to internal control beta-actin (ACTB) were analyzed by real-time PCR using Hs00918176_m1 and 4352935E primers and probes (Applied Biosystems), respectively. Htt/ACTB ratios for ZFP transfected samples were normalized to that of the GFP control (set as 1).

Figure 3A:
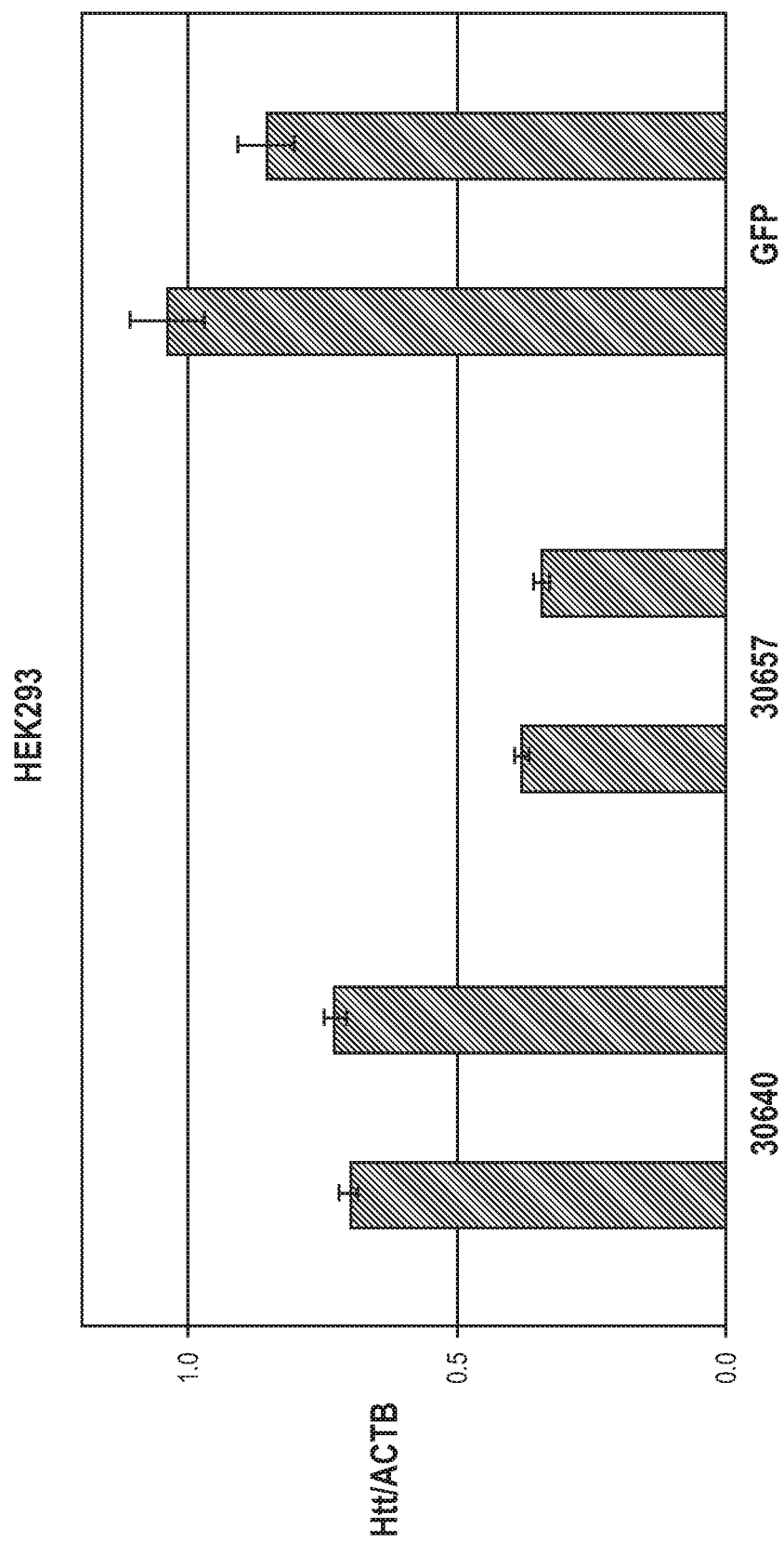

As shown in FIG. 3A, ZFP repressors (fused with KRAB repression domain) designed to bind to CAG repeats (FIG. 1B), either to top or bottom strand, in HEK293 cells, effectively repressed Htt expression. FIG. 3A depicts repressors of transcription where expression was measure in duplicate transfections (separate bars in the Figure) and multiple real-time PCR assays completed (error bars). Different levels of repression by individual ZFPs suggest that they have different affinity to the CAG repeat region. Because Htt alleles in HEK293 cells have 16 (SEQ ID NO: 251) and 17 CAG (SEQ ID NO: 236), this result also suggests that "weaker" ZFPs, such as 30640, do not repress Htt alleles with wild-type (unexpanded) CAG repeat length effectively.

To test whether ZFPs such as 30640 can repress transcription of Htt alleles with expanded CAG repeats, luciferase reporters controlled by Htt promoter/exon 1 fragment that contains different CAG repeat lengths were constructed. First, the human Htt promoter/exon1 fragment was amplified from HEK293 genomic DNA using forward primer:

(SEQ ID NO: 139)
5' GAAGATCTCACTTGGGGTCCTCAGGTCGTGCCGAC and reverse primer:

(SEQ ID NO: 140)
5' GTATCCAAGCTTCAGCTTTTCCAGGGTCGCCTAGGCGGTCT..

The forward primer introduces a BglII site, the reverse primer changes the first ATG of Htt into TAG and creates an AvrII site, and also includes a HindIII site. The PCR product was digested with BglII and HindIII and ligated to pRL-TK vector (Promega) that was digested with the same enzymes to generate the construct pRL-Htt. Then the human Htt exon1 fragment (coding sequence minus first ATG) was amplified from HEK293 genomic DNA or genomic DNA from HD patients with expanded CAG repeats using forward primer:

(SEQ ID NO: 141)
5' GCCTAGGCGACCCTGGAAAAGCTGATGAAGGCC and reverse primer:

(SEQ ID NO: 142)
5'
5' GTATCCAAGCTTGAGCTGCAGCGGGCCCAAACTCACG.

The forward primer introduces an AvrII site, the reverse primer introduces a HindIII site. The PCR product was digested with AvrII and HindIII and ligated to pRL-Htt vector that was digested with the same enzymes. Clones with 10 (SEQ ID NO: 234), 17 (SEQ ID NO: 236), 23 (SEQ ID NO: 237) or 47 (SEQ ID NO: 235) CAG repeats (pRL-Htt-CAG(x)) were identified by sequencing.

pRL-Htt-CAG(x) reporters (300 ng) and pGL3-promoter reporter (100 ng, used as normalization control, Progema) were transfected into HEK293 cells with or without 100 ng of ZFP 30640 expression vector. Firefly (pGL reporter) and renilla (pRL reporter) luciferase activities were measured 24 hours after transfection. Renilla luciferase levels were normalized to those of firefly luciferase from the same transfected sample, and further normalized to the renilla/firefly ratio of the "reporter only" sample.

As shown in FIG. 3B, repression of the luciferase reporters by ZFP-TF 30640 increases with the length of the CAG repeat, suggesting that ZFPs with DNA binding affinities similar to that of 30640 can repress Htt promoter activity via an expanded CAG repeat, and the level of repression is dependent on the CAG repeat lengths.

FIG. 3C shows a similar experiment as in FIG. 3B, except the "strong" ZFP-TF 30657 was also tested, and both 30640 and 30657 were tested at multiple doses as indicated. At every dose level, 30640 gave more repression of the pRL-Htt-CAG47 ("CAG47" disclosed as SEQ ID NO: 235) reporter than the pRL-Htt-CAG23 reporter ("CAG23" disclosed as SEQ ID NO: 237) (CAG repeat length-dependent repression), while 30657 repressed both reporters to similar levels. On the pRL-Htt-CAG23 ("CAG23" disclosed as SEQ ID NO: 237) reporter, 30640 gave less repression than 30657 at every dose level, recapitulating the difference in their activities on the endogenous Htt allele with normal CAG repeat length (HEK293 cells, FIG. 3A); but on the pRL-Htt-CAG47 ("CAG47" disclosed as SEQ ID NO: 235) reporter, 30640 and 30657 gave similar repression at every dose level, suggesting that "weaker" ZFPs such as 30640 can efficiently repress Htt promoter through an expanded CAG repeat, most likely because only an expanded CAG target can allow threshold occupancy required for repression to be established by such ZFPs.

Figure 3D:
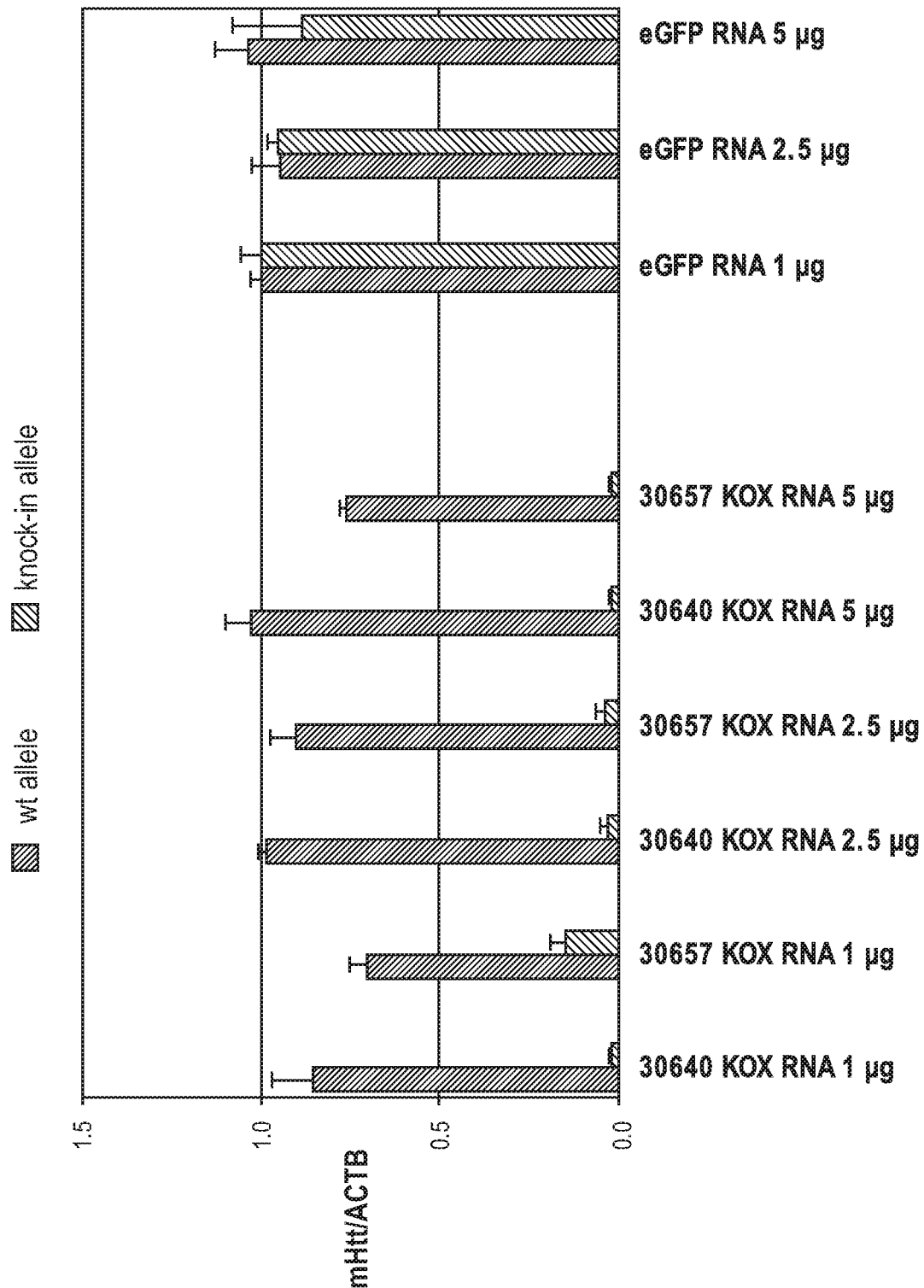

FIG. 3D shows ZFP-TFs 30640 and 30657 (fused to the KRAB repression domain of KOX1) can repress the knock-in Htt allele (CAG111) in immortalized striatal cells derived from the Hdh(Q111/Q7) knock-in mice, demonstrating the ZFPs such as 30640, which drives CAG repeat length-dependent repression of luciferase reporters, can also repress expression from an endogenous Htt allele that has expanded CAG repeat. mRNA for indicated ZFPs were generated using the mMessage mMachine kit (Ambion), and transfected into Hdh(Q111/Q7) cells at indicated doses using Amaxa nucleofector. To detect expression from the wt mouse Htt allele, forward primer CAGGTCCGGCAGAG-GAACC (SEQ ID NO:193) and reverse primer TTCACACGGTCTTTCTTGGTGG (SEQ ID NO:194) were used in the real-time RT-PCR; to detect expression from the knockin Htt allele, forward primer GCCCGGCTGTGGCTGA (SEQ ID NO:195) and reverse primer TTCACACGGTCTTTCTTGGTGG (SEQ ID NO:196) were used.

FIG. 3E show the result of testing the ZFP-TFs 30640 and 30657 in an HD patient-derived fibroblast line (GM21756, Coriell) that has 15 (SEQ ID NO: 239) and 70 (SEQ ID NO: 240) CAGs on the normal and mutant Htt allele, respectively. A SNP-based allele-specific real-time PCR assay was first established to allow specific detection from the wild type or the mutant Htt allele. The phasing of the SNP (r5363099 T/C) was determined by Carroll, et al. (2011) *Mol Ther.* 19:2178-85; "T" is on the normal allele and "C" is on the mutant allele. To detect Htt expression from the mutant allele (099C), cDNA from the fibroblast was amplified by real-time PCR (SsoFast EvaGreen Supermix, Bio-Rad) using forward primer 099C.F (5'AGTTTG-GAGGGTTTCTC, SEQ ID NO:143) and reverse primer 099.R5 (5' TCGACTAAAGCAGGATTTCAGG, SEQ ID NO:144); the annealing/extension temperature was 55.6° C. To detect Htt expression from the wild type allele (099T), real-time PCR of the fibroblast cDNA were done using forward primer 099T.F (5'AGTTTGGAGGGTTTCTT, SEQ ID NO:145), reverse primer 099.R5 and the 3'phosphorylated blocker oligo 099T.BL (5'AGGGTTTCTCCGCTCAGC-3'phos, SEQ ID NO:146); the annealing/extension temperature was 58.3° C. Total human Huntingtin (hHtt, both wt and mutant allele) levels and normalization control beta-actin (ACTB) levels were analyzed by real-time PCR using primer/probe Hs00918176_m1 and 4352935E (Applied Biosystems), respectively. For the experiment shown in FIG. 3E, mRNA for indicated ZFPs were generated using the mMessage mMachine kit (Ambion), 1 ug of mRNA was transfected using Amaxa nucleofector as above. Cells were harvested 48 hours after transfection; mRNA levels from the normal (CAG15 (SEQ ID NO: 239), 099T), the mutant (CAG70 (SEQ ID NO: 240), 099C) Htt allele and total Htt (hHtt) were quantified as described above and normalized to the levels of ACTB; the Htt/ACTB ratios for each sample was further normalized to that of the mock-transfected sample. The "strong" CAG-targeted ZFP 30657 repressed both alleles, as expected (based on its activity in HEK293 cells FIG. 3A). ZFP 30640, which showed CAG repeat length-dependent repression of the reporters, gave <10% repression of the wild-type allele while repressed the mutant allele >90%. The levels of total Htt in each sample were consistent with those of wt and mutant Htt levels in the same sample.

Figure 3F:
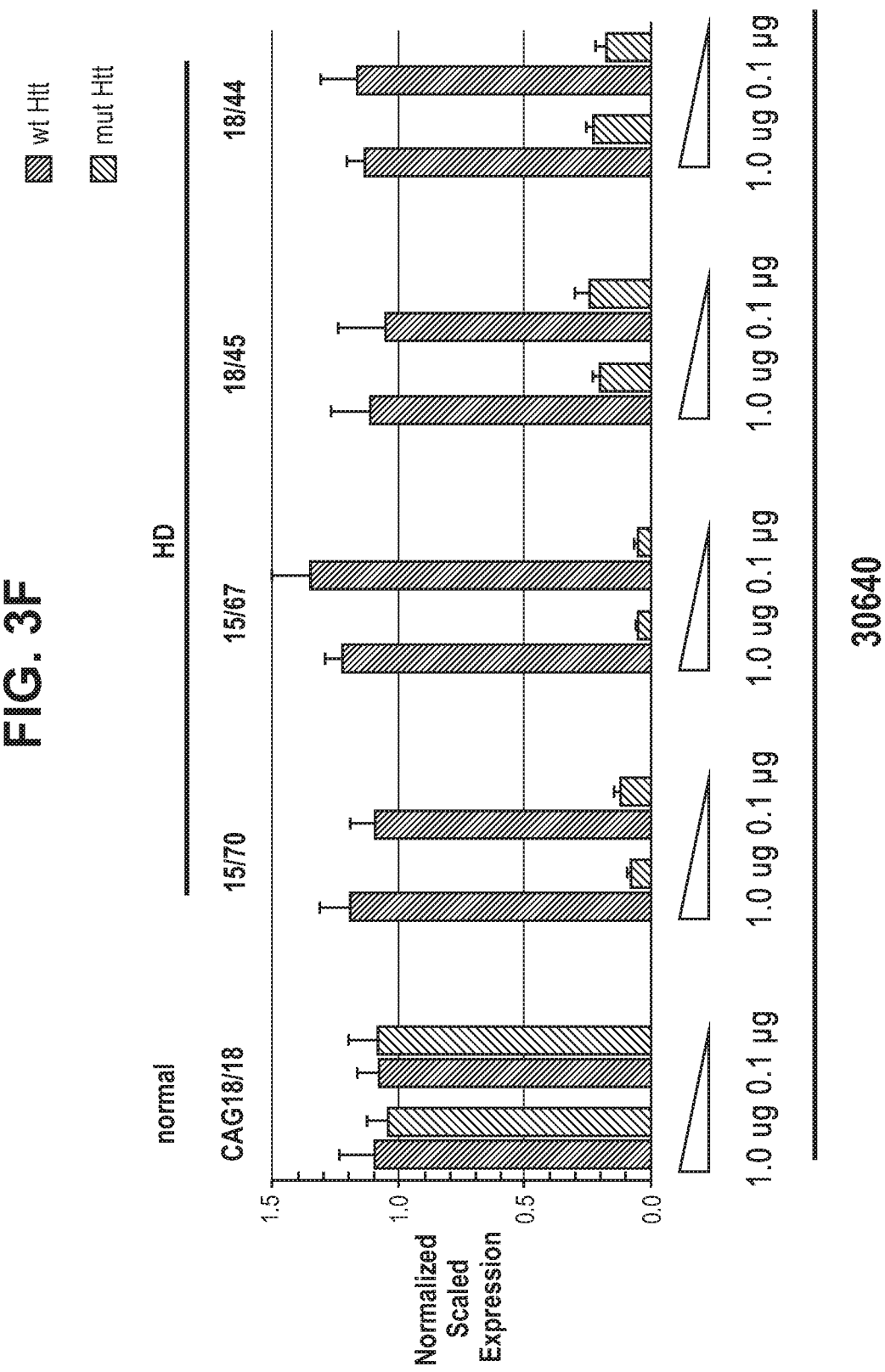

ZFP-30640 was also tested in a normal fibroblast line as well as other HD fibroblast lines that contain different CAG repeat length in the Htt gene (see FIG. 3F). Htt expression from each allele was detected as described above. No Htt repression was observed in the normal fibroblast line (CAG18/18 (SEQ ID NOS 245 and 245)). In contrast, excellent allelic discrimination was observed in the CAG 15/67 (SEQ ID NOS 239 and 242) and CAG15/70 (SEQ ID NOS 239 and 240) lines at both a high and low dose of transfected 30640 mRNA; similar results were obtain for the two HD fibroblast lines with intermediate CAG repeat length on the mutant allele (CAG 18/44 (SEQ ID NOS 245 and 244) and CAG 18/45 (SEQ ID NOS 245 and 243))—wherein the expanded allele is repressed by ~80% at both the high and low doses of 30640, yet the CAG18 (SEQ ID NO: 245) allele remained unaffected. Taken together, these data indicate that allele-specific repressors such as 30640 can maintain strong CAG allele length selectivity in the context of more prevalent disease genotypes such as CAG18/44 (SEQ ID NOS 245 and 244) and CAG18/45 (SEQ ID NOS 245 and 243).

Western blot analysis was used to show that that ZFPs such as 30640 selectively down-regulated mutant Htt protein levels in two patient-derived fibroblast lines, confirming allele-specific regulation that was shown by qPCR assays (see FIG. 3G). ZFPs were delivered by mRNA transfection (Amaxa nucleofection) at a 300 ng dose into 4 replicates of 1.5e5 cells and pooled prior to plating in 12-well plates. At 48 hours, cells were washed and harvested for protein extract preparation. Approximately 2.5 ug of extract was loaded onto 5% Tris-acetate gels and detected by MAB2166 (Millipore). Additionally, the same samples were loaded on a 4-15% Tris-HCl gels (Bio-Rad) and transferred using standard methods for detection by an anti B-Actin (1:20,000, Sigma) as loading controls. Based on qPCR studies that measure Htt mRNA, 30640 is an allele-specific repressor targeting the CAG repeat; 32528 is biallelic repressors targeting the transcription start site (TSS), and 30657 is CAG-targeted repressor that repress both Htt alleles at the dose that was used. Western blot showed that 30640 specifically reduced the levels of mutant Htt (upper band) in both HD patient-derived cell lines, while 32528 and 30657 repressed both alleles similarly.

Example 4: Additional CAG-Targeted ZFP Designs that Drive Allele Specific Repression of Htt FIG. 4A shows the results of testing ZFP-TFs 30640, 30643, 30645 and 33074 (all targeted to the CAG repeat and uses the KRAB repression domain) in a CAG18/45 (SEQ ID NOS 245 and 243) HD fibroblast line. Different amounts of ZFP mRNA were transfected using Amaxa nucleofector as indicated, expression of the mutant Htt (right bar), wild type Htt (middle bar) and total Htt (both alleles, left bar) were measured as described above at 24 hours after transfection. ZFPs 30640, 30645 and 33074 drive allele-specific repression over the entire 3 ug-10 ng ZFP mRNA dose range; while 30643 appears to repress both alleles significantly at doses that are 30 ng or higher, and begins to exhibit allele selectivity at the 10 ng dose.

FIG. 4B shows the results of testing ZFP 30643, 30648, 30657 and 30658 (all targeted to CAG repeat and uses the KRAB repression domain) in a CAG15/70 (SEQ ID NOS 239 and 240) HD fibroblast line. Different amounts of ZFP mRNA were transfected using Amaxa nucleofector as indicated, expression of the mutant Htt (right bar), wild type Htt (middle bar) and total Htt (both alleles, left bar) were measured as described above at 24 hours after transfection. Compared to the ZFPs that were tested in the previous figure (30640, 30645 and 33074), these ZFPs drive mutant Htt-specific repression at lower doses. These results suggest that depend on ZFP expression levels that can be achieved in vivo (e.g. in the brains of HD patients), allele-specific repression of mutant Htt can be achieved using appropriate ZFP designs.

Example 5: Repression of Alternate CAG-Containing Genes

Figure 5:
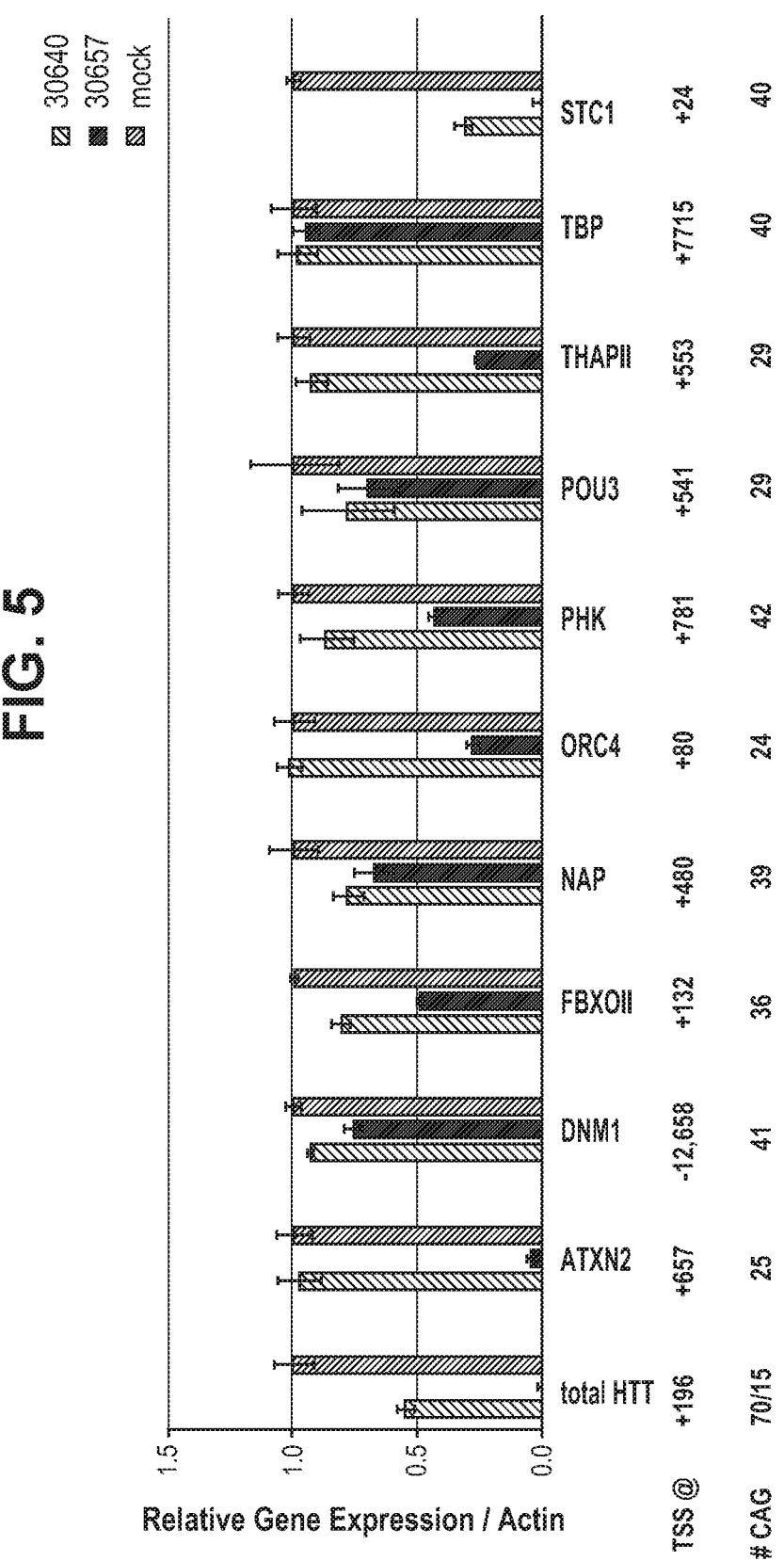
FIG. 5 shows the effect of CAG-targeted ZFP repressors on the expression of Htt and other CAG-containing genes in HD patient-derived fibroblasts. The left bar under each indicated condition shows results with 30640; the middle bar under each indicated condition shows results with 30675; and the right bar shows mock transfections.

Using the RNAs isolated in Example 3 (FIG. 3E), repression of other CAG repeat containing genes was analyzed, and the results are depicted in FIG. 5. The expression levels of the following genes was examined using real-time PCR and normalized to that of Actin: Ataxin 2 ("ATXN2"); Dynamin ("DNM1"); F-box only protein 11 ("FBXO11"), nitrate reductase ("NAP"); Origin recognition complex subunit 4 ("ORC4"); phosphokinase ("PHK"); OCT3/4 protein ("POU3"); THAP domain containing, apoptosis associated protein 2 ("THAPII"); TATA binding protein ("TBP"); and stanniocalcin 1("STC1"). In addition, the location of the CAG repeat sequence relative to the transcriptional start site (TSS) was noted, and is indicated in FIG. 3F as "TSS@", where "+" indicates base position of CAG repeats that are downstream of TSS, and "−" indicates base position of CAG repeats that are upstream of TSS. Also, the number of CAG repeats ("# CAG") is indicated for each gene.

The data demonstrate that repression of the mutant expanded Htt allele by 30640 is highly specific, and only a subset of CAG repeat-containing genes whose CAG repeats are relatively close to their respective transcroption start sites maybe repression targets of ZFPs such as 30640.

Example 6: Genome-Wide Specificity of Allele-Specific ZFP Repressors of Htt

Figures 6A, 6B:
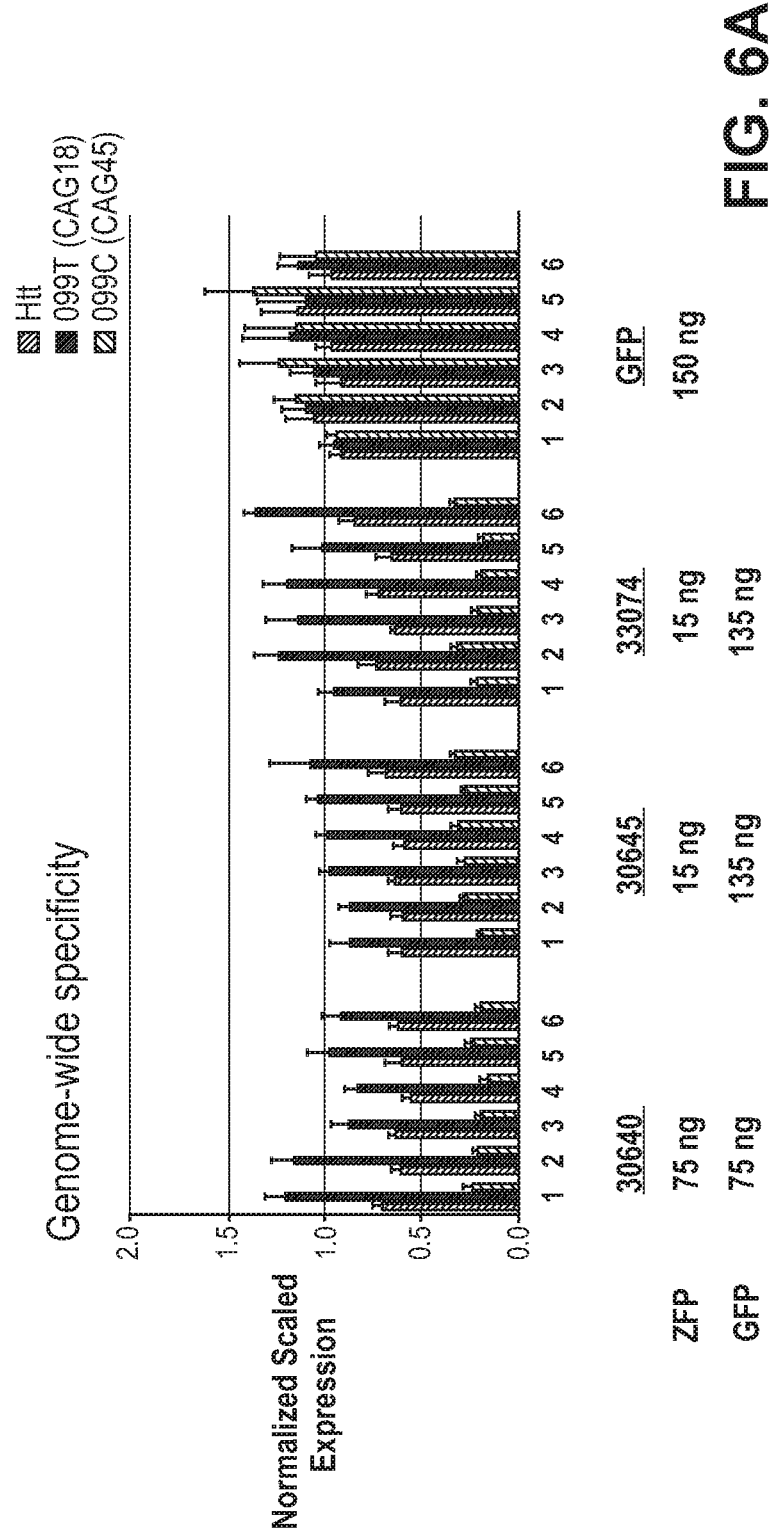
FIGS. 6A and 6B depict an experiment that examines the genome-wide specificity of three CAG-targeted ZFPs.

HD fibroblasts (CAG18/45 (SEQ ID NOS 245 and 243)) were transfected to study genome-wide specificity of CAG-targeted ZFPs by microarray analysis (FIG. 6). ZFPs were delivered by mRNA transfection (Amaxa nucleofection) at the indicated doses—ZFPs 30640, 30645 and 33074 were transfected in sextuplicate at the 75 ng, 15 ng and 15 ng dose, respectively; GFP-Kox mRNA (150 ng) was transfected as a control, and was used as carrier to bring the total amount of transfected mRNA to 150 ng in all samples. Expression from CAG18 (SEQ ID NO: 245) (099T, middle bars) and CAG45 (SEQ ID NO: 243) (099C, right bars) alleles was measured by allele-specific qPCR reagents at 24 hours after transfection as described above where each of the samples (1-6) are biological replicates (separate transfections). Htt levels were normalized to those of GAPDH. Mutant allele-specific repression of Htt was observed for all three ZFPs. The four most similar replicates were then chosen for microarray analysis (Affymetrix HGU133plus2.0) as follows: GFP replicate 1, 3, 4 and 6; 30640 replicate 2, 3, 5 and 6; 30645 replicate 2, 3, 5 and 6; and 33074 replicate 1, 3, 4 and 5 were used for microarray analysis. Robust Multi-array Average (RMA) was used to normalize raw signals from each probe set; ZFP-transfected samples were compared to GFP-transfected samples using T-test; "change" calls were made on genes (probe sets) with >2 fold difference relative to control samples and T-test P-value<0.05. Based on that criterion, 30640 repressed only two genes, stanniocalcin 1 (STC1) and extended synaptotagmin-like protein 1 (ESYT1); 30645 and 33074 only repressed one gene each, STC1 and interleukin 17 receptor A (ILR17RA), respectively. Htt was not detected as a repressed (>2-fold repression) gene because the Htt probe set on the array detects both wt and mutant Htt mRNA. This experiment demonstrates that mutant Htt-specific ZFPs, when expressed at levels that drive efficient allele-specific repression of Htt, can operate with very high specificity genome-wide.

Example 7: Allele Specific Repression in HD Neural Stem Cells (NSCs)

HD iPSC/ESCs were passaged with accutase and cultured on matrigel coated plates in E8 media (Life Technologies). Neural stem cells were derived using StemPro Neural Induction Medium (Life Technologies). Briefly, iPSC/ESCs were seeded into geltrex coated 6 well dish with 200,000 cells/ well and when 10-20% confluent the medium was changed to StemPro Neural Induction Medium. Medium was changed every 2 days and NSC harvested and expanded on day 7. StemPro NSC SFM medium (Life Technologies) was used to culture NSCs. HD NSCs(CAG17/69 (SEQ ID NOS 236 and 246), derived from Coriell GM23225 iPSC) were transfected with 1.5 or 0.5 μg ZFP mRNA using nucleofection. Forty-eight hours post transfection cells were harvested and expression quantified by RT-PCR. Allele-specific detection of Htt expression was performed using a SNP (rs1143646)-based genotyping assay #4351376 (Applied Biosystems). At the ZFP doses that were tested, 30640 gave allele-specific repression of mutant Htt, 30643 gave ~50% repression of wt Htt and ~90% repression of mutant Htt, and 30648 repressed both alleles (FIG. 7); the behavior of these ZFPs is consistent with that in HD fibroblasts (FIG. 4). The total Htt levels (middle bars) for each sample is consistent with levels of mutant and wt Htt levels.

Example 8: Htt Repression in Differentiated HD Neurons

HD NSCs were passaged with accutase on geltrex coated plates. Neuron differentiation was induced by changing medium to neural differentiation medium containing Stem-PRO NSC SFM medium without (bFGF and EGF). Medium was changed every 3-4 days for up to 21 days. Neurons were derived from NSC (CAG17/48 (SEQ ID NOS 236 and 247), derived from HD ESCs) by culture in neural differentiation medium. On day 15 post neural induction cells were transfected with 1.0 or 0.5 µg ZFP mRNA using nucleofection. Forty-eight hours post transfection cells were harvested and gene expression quantified by RT-PCR. Because this patient line does not contain a SNP that allows qPCR-based allele-specific detection of wt and mutant Htt, only total Htt levels can be measured. Because we showed that 30640 and 33074 does not repress the CAG18 (SEQ ID NO: 245) or CAG17 (SEQ ID NO: 236) allele in HD fibroblasts and NSCs, the levels of total Htt observed in 30640- and 33074-treated samples are consistent with allele-specific repression of the mutant allele (CAG48 (SEQ ID NO: 247)). More potent repression by 30643 and 30648 at the ZFP doses tested is also consistent with the behavior of these ZFPs in HD fibroblasts (FIG. 8).

Example 9: A CAG Targeted Repressor Represses Mutant Htt Transgene in R6/2 Mice

Figure 9:
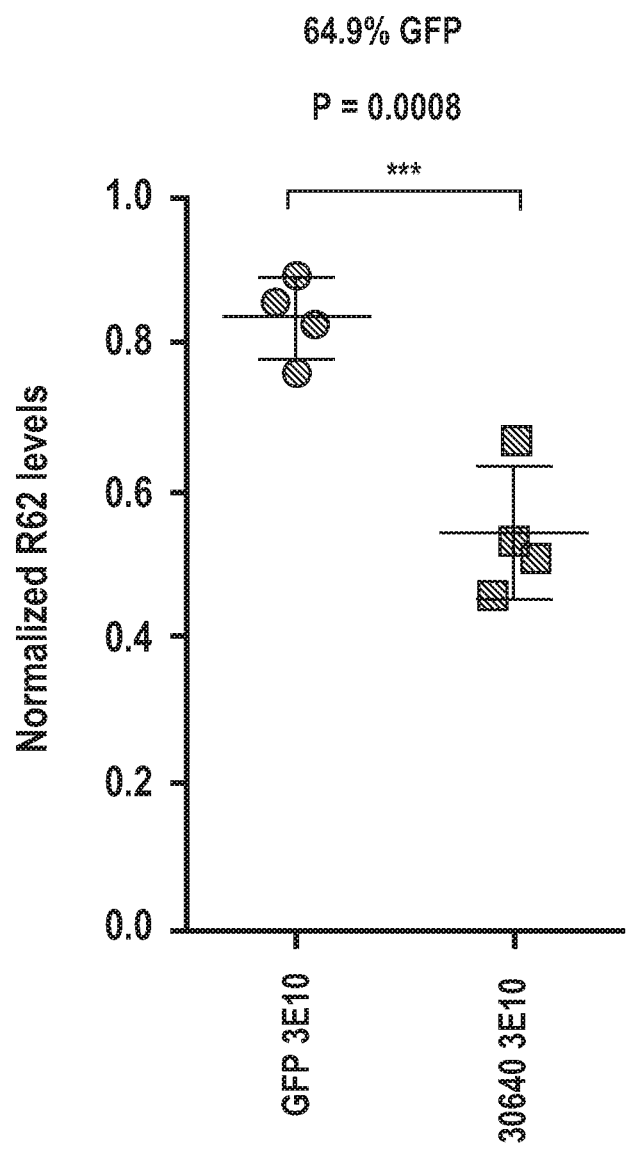
FIG. 9 depicts repression of a mutant Htt transgene expression in R6/2 mice following treatment with the ZFP TF 30640.

R6/2 mice (which carries a transgene of mutant human Htt exon 1 with ~120 CAG repeat (SEQ ID NO: 252), see Mangiarini, et al. (1996) *Cell* 15:197) received stereotactic, bilateral striatal injections of 3e10 vector genome of recombinant AAV2/6 encoding either ZFP 30640-KOX or GFP driven by a CMV promoter. Mice were injected at 5 weeks of age and sacrificed for molecular analysis at 8 weeks of age. Left and right striata were dissected from each hemisphere and snap frozen. To assess repression of the mutant Htt transgene, total RNA was extracted from each striatum with TRIzol Plus (Life Technologies) followed by cDNA synthesis using High Capacity RT (Life Technologies). Subsequently, R6/2 transgene expression was measured by qPCR and normalized to the geometric mean of three reference genes (Atp5b, Eif4a2, UbC) as previously described by Benn, et al. (2008) *Molecular Neurodegeneration:* 3:17. We observed statistically significant repression (P<0.001) of the mutant Htt transgene in four ZFP-treated striata relative to the four GFP-treated control striata (FIG. 9). The average R6/2 repression was 64.9% of the GFP-treated controls. Because complete coverage of the striatum was not achieved using a single stereotactic injection and AAV2/6 preferentially transduces neuronal cells, the fold of repression observed (~35%) is likely an underestimate of actual repression in cells that were transduced with the AAV vector.

Example 10: Selective Repression of Mutant Htt using ZFPs with Dimerization/Multimerization Domains In order to engineer zinc finger transcription factors to better discriminate between short CAG and long GAG repeats, we sought to both decrease the DNA-binding affinity of individual zinc finger transcription factors and increase the interaction strength between different copies of fusion protein bound to adjacent subsites within the CAG repeat. In order to decrease the DNA-binding affinity of individual zinc finger transcription factors, we generated zinc finger domains with fewer zinc fingers and/or with amino acid sequences expected to bind DNA with less than optimal affinity. In order increase the interaction strength between different copies of fusion protein bound to adjacent subsites within the CAG repeat, we fused various dimerization domains to our zinc finger transcription factors. The dimerization domains can interact in a "parallel" fashion and yield "head-to-head" or "tail-to-tail" dimers of fusion proteins that contain them. One potential dimerization strategy requires an array of identical ZFP-transcription factor fusions that bind in a "head-to-tail" orientation and thus this strategy requires dimerization domains that interact in an "anti-parallel" fashion. See, e.g., McClain, et al. (2001) *J. Am. Chem. Soc.* 123:3151-3152) and dimerizing zinc finger peptides (Giesecke, et al. (2006) *Molecular Systems Biology* 2:2006-2011).

Dimerization contructs CC1 and CC2 were based on pairs of antiparallel coiled coils (McClain, et al., ibid, Ghosh, et al. (2000) *J Am Chem Soc* 122:5658-5659). Dimerization constructs CC3 and CC4 were truncated versions of CC2 that lack either 4 residues or 7 residues respectively. Dimerization constructs DZ1, DZ2, DZ3, and DZ4 were based on pairs of dimerizing zinc finger domains (Giesecke, et al., ibid). In each case, one member of the pair was fused to the N-terminus of the zinc finger DNA binding domain and the other member of the pair was fused to the C-terminus of the zinc finger DNA binding domain. Short linkers rich in glycine and serine residues were used to fuse the dimerization domains to the zinc finger binding domain. Additional embodiments of the invention utilize linkers with alternate lengths and/or amino acid composition. Linkers with one or more residues removed or with one or more glycine or serine residues changes to other amino acid residues will reduce the flexibility of these linkers and may result in improved discrimination between long and short CAG repeats.

Figure 11A:
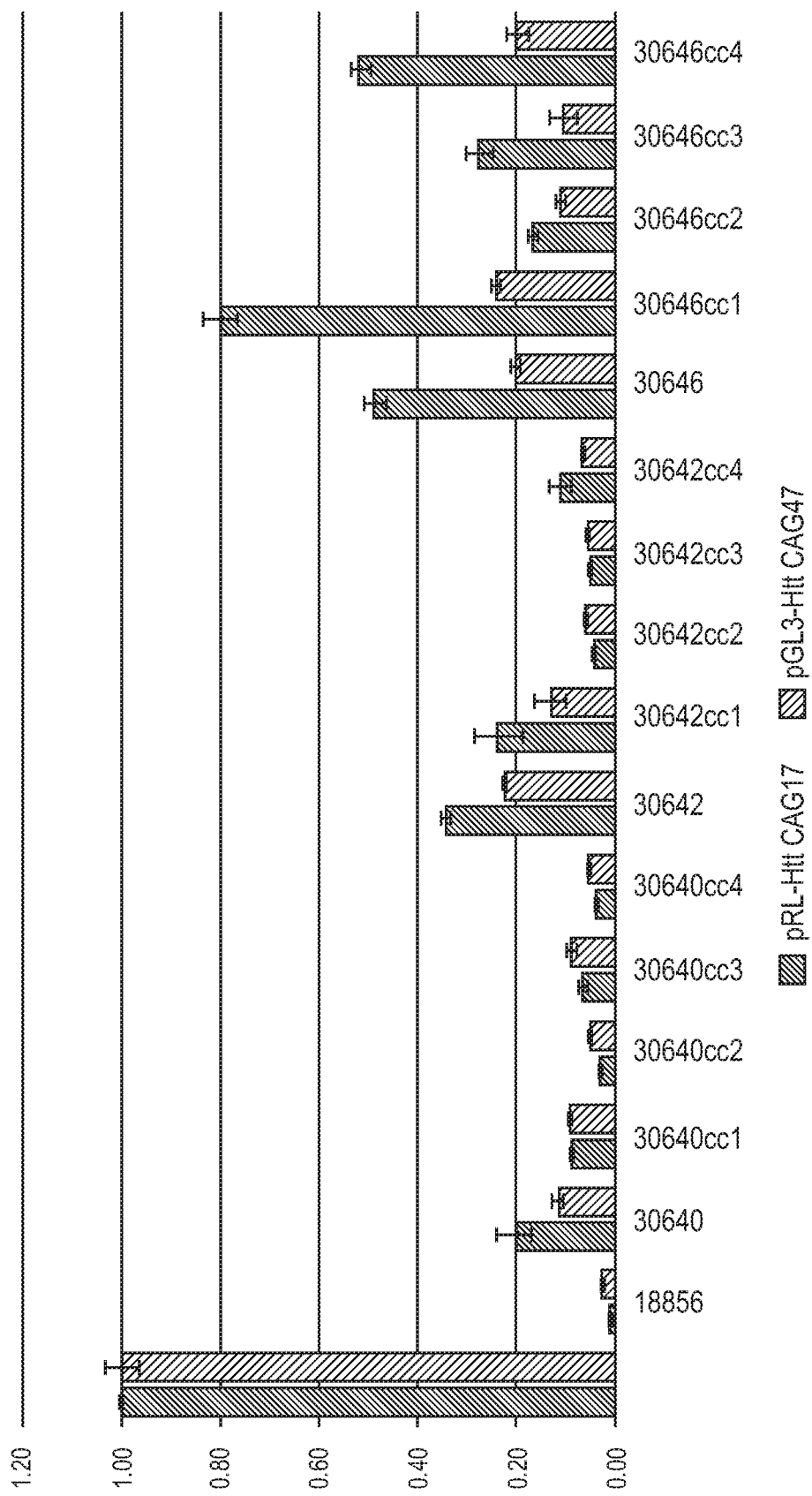

To achieve selective repression of the mutant Htt allele, ZFPs were designed as illustrated in FIG. 1D and FIGS. 10A and 4B. FIGS. 10C and 10D show the sequences of the multimerization domains. FIGS. 11A and 11B depict the results that experiments designed to measure the ability of the ZFP-TFs comprising the CC and DZ domains, respectively to repress their targets. For these experiments, indicated ZFP constructs (50 ng) were co-transfected with pRL-Htt-CAG17 ("CAG17" disclosed as SEQ ID NO: 236) (200 ng), pGL3-Htt-CAG47 ("CAG47" disclosed as SEQ ID NO: 235) (200 ng) and pVax-SEAP (secreted alkaline phosphatase, 10 ng, used as normalization control) into HEK293 cells. Luciferase activity and secreted alkaline phosphatase activities were measured 24 hours after transfection. The Renilla luciferase (CAG17 (SEQ ID NO: 236))/SEAP and firefly luciferase (CAG47 (SEQ ID NO: 235))/SEAP ratios for each sample were normalized to those of the reporter-only samples. The pGL3-Htt-CAG47 ("CAG47" disclosed as SEQ ID NO: 235) reporter was constructed in the same way as the pRL-Htt-CAG47 ("CAG47" disclosed as SEQ ID NO: 235) reporter (see Example 3), except the pGL-promoter construct (Promega) was used instead of the pRL-TK construct.

As shown in FIG. 11A, 3 ZFPs, when tested asone or more CC domain-containing constructs, enhanced repression of one or both reporters when compared to constructs with the same ZFP but no CC domains. FIG. 11B shows that DZ1 and DZ3 domains enhanced repression of 32220 on both reporters.

These results suggest that the CC and DZ domains can in general increase affinity of multimerized ZFPs and that design of the DNA binding domain and the dimerization domain may yield optimal CAG-repeat length discrimination.

Example 11: Selective Repression of Mutant Htt with ZFP-ZFP-Kox Designs

ZFP TFs were tested in HD fibroblasts that were of the ZFP-ZFP-KOX design. In these experiments, the two ZFP DNA binding domains were linked together with a flexible linker (LRQKDAARGSAAMAERPFQ, SEQ ID NO:179) and fused to a KOX repression domain. The linker was placed between the conserved histidines and cysteines. The proteins were tested as described above using ZFP mRNA at indicated doses. These results in the CAG18/45 (SEQ ID NOS 245 and 243) (FIG. 12A) and CAG20/41 (SEQ ID NOS 248 and 249) (FIG. 12B) HD fibroblast lines demonstrated that linking less active ZFP DNA binding domains in this fashion can result in composite ZFPs that drive allele-specific repression.

Example 12: Activation of Htt in Mouse Cells

ZFPs as described herein were also evaluated for their ability to activate Htt expression. ZFPs targeted to the +200 to +467 bp region (relative to the transcription start site) of mouse Htt were fused to the transcriptional activation domain of NFκB p65 subunit. This targeting region was chosen because this fragment was replaced by the corresponding sequence (majority of exon 1 and some intron 1 sequence) from human Htt in various knock-in mouse models of HD (Menalled, et al. (2003) *J. Comp. Neurol* 4651:11-26; Wheeler, et al. (2000) *Hum Mol Genet* 8:115-122), therefore ZFPs targeted to this region can selectively activate the wild type allele in those animals but not the knock-in allele.

ZFPs were transfected into Neuro2A cells (both Htt alleles are wild type in these cells), mouse Htt and ACTB mRNA levels were measured as described in Example 2 (duplicate transfections and multiple assays).

As shown in FIG. 13, an increase in Htt mRNA levels as compared to a mock transfection was detected using both ZFP-TFs. See, FIG. 13A. Increased Htt protein levels were confirmed by Western blot. See, FIG. 13B.

Figure 13A:
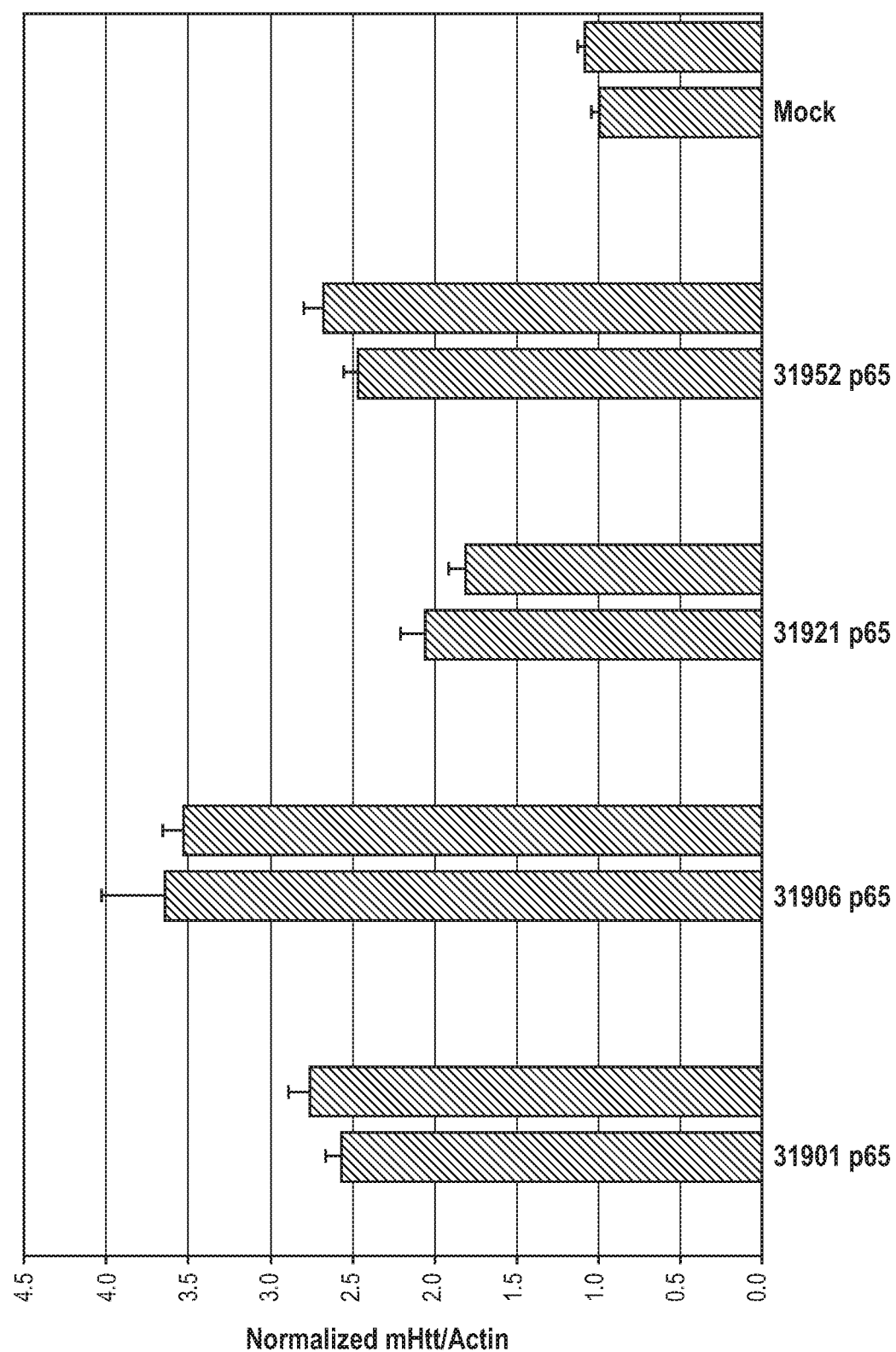
FIGS. 13A through 13E depict activation of mouse Htt.
Figure 13B:
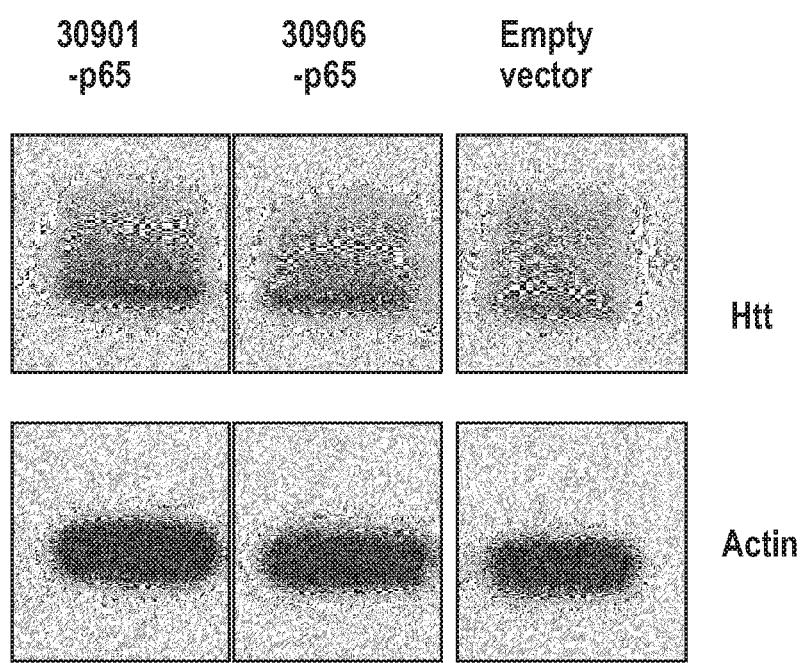
Figures 13C, 13D:
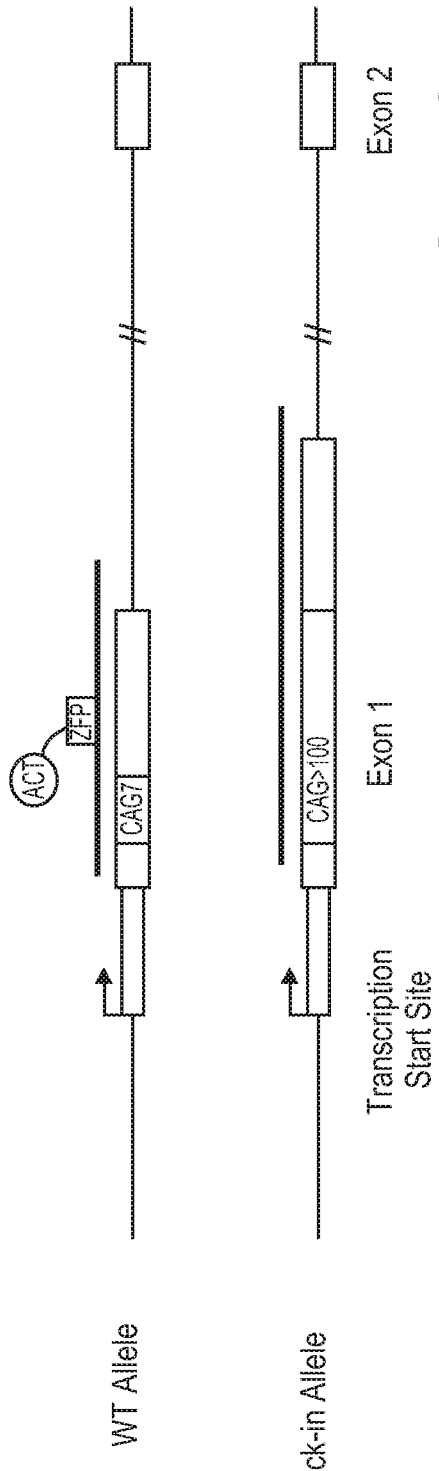
Figure 13E:
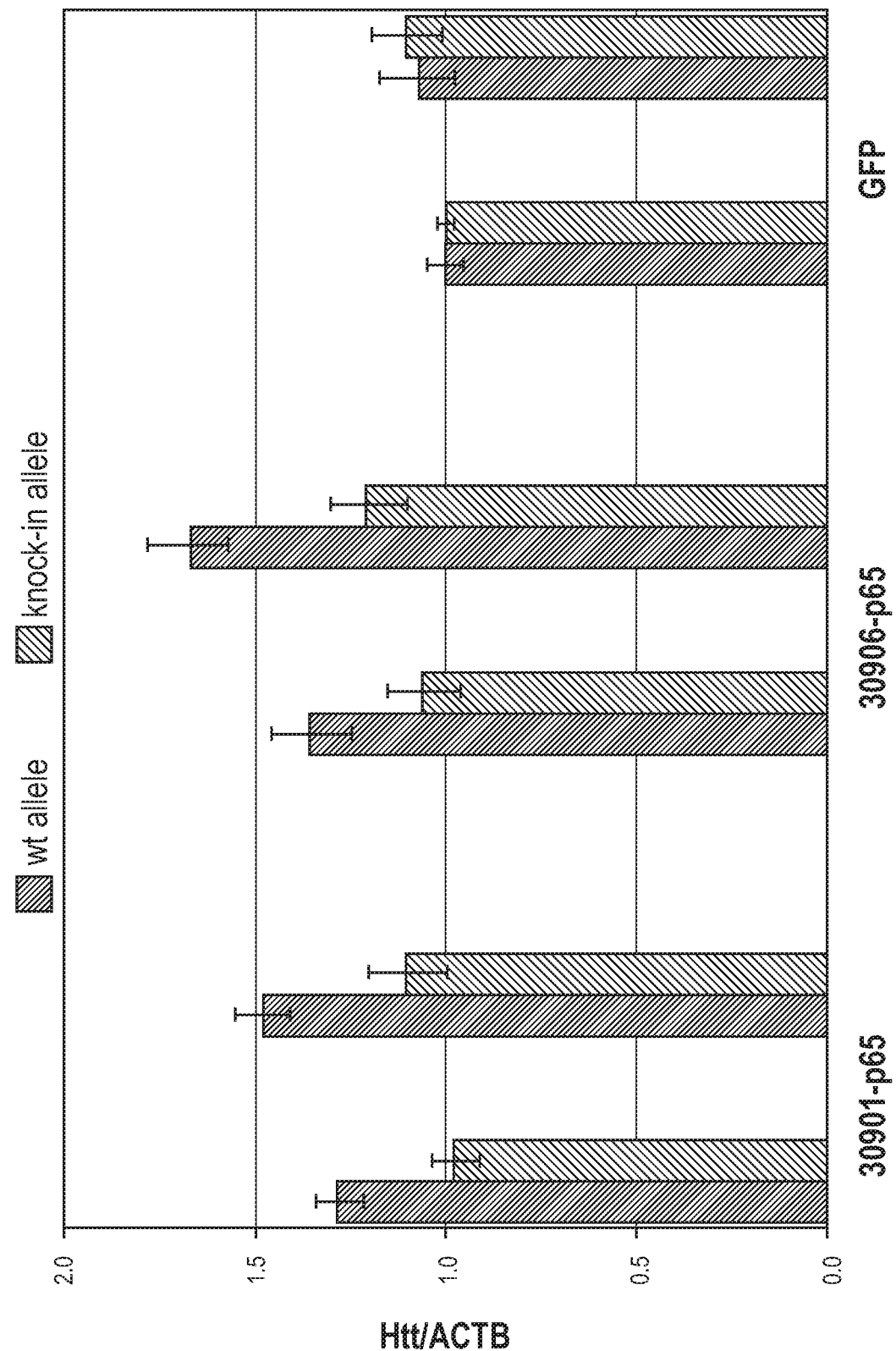

The generation of the knock-in Htt allele is illustrated in FIG. 13C; sequence alignment (FIG. 13D) shows divergence between the mouse sequence that was replaced and the corresponding human sequence. FIG. 13E shows that when such ZFP activators were transfected into immortalized striatal cells derived from HdhQ111/Q7 knock-in mice, only the wild type Htt was selectively activated.

Example 13: Regulation of Htt Expression In Vivo

To test efficacy of the Htt-specific ZFP TFs in vivo, AAV2 vectors encoding the ZFPs are produced. These AAV2 based constructs are then delivered to the brains of mice. For human Htt-specific ZFP TFs, AAV vectors are delivered to R6.2 mice or BAC HD mice (C57Bl/6 or FVB/N strains) to assess the repression of the human transgene, as well as change in HD-like phenotypes. For mouse Htt-specific ZFPs (activators or repressors), AAV vectors are delivered to wild-type mice (C57Bl/6 or FVB/N) or human Htt knock-in mice (HdhQ111/Q7, HdhQ140/Q7 or HdhQ175/Q7) to assess the activation or repression of the endogenous mouse Htt expression. For ZFPs that preferentially targeting the CAG-expanded allele, AAV vectors are delivered to R6.2 mice or human Htt knock-in mice (HdhQ111/Q7, HdhQ140/Q7 or HdhQ175/Q7) to examine the selective repression of wt vs. expanded Htt allele. Following sacrifice, brain tissues are analyzed for Htt expression by Taqman real-time RT-PCR, and demonstrate that the Htt genes are modulated by ZFP-TFs.

Example 14: Co-Transfection of a Neurotrophic Factor and a HD Htt Allele-Specific ZFP TF The Htt-specific ZFP TFs identified above are co-transfected with ZFP TFs-specific for a brain neurotrophic factor. The ZFP TF specific for brain neurotrophic factors used are specific for either GDNF or BDNF.

Example 15: Design and Construction of Htt-Targeted Zinc Finger Nucleases (ZFNs)

ZFNs targeting human Htt and mouse Htt were designed to target the sequences flanking the CAG repeats, sequences near the first coding ATG, the stop codon, as well as in early exons. ZFNs were designed and incorporated into plasmids or adenoviral vectors essentially as described in Urnov, et al. (2005) *Nature* 435(7042):646-651; Perez, et al. (2008) *Nature Biotechnology* 26(7):808-816; and U.S. Patent Publication No. 2008/0131962.

Example 16: Cleavage Activity of Htt-Specific ZFNs

To test cleavage activity, plasmids encoding the pairs of human Htt-specific ZFNs described above were transfected into K562 cells. K562 cells were obtained from the American Type Culture Collection and grown as recommended in F-12 medium (Invitrogen) supplemented with 10% qualified fetal calf serum (FCS, Cyclone). Cells were disassociated from plastic ware using TrypLE Select™ protease (Invitrogen). For transfection, one million K562 cells were mixed with 2 μg of the zinc-finger nuclease plasmid and 100 μL Amaxa Solution T. Cells were transfected in an Amaxa Nucleofector II™ using program U-23 and recovered into 1.4 mL warm F-12 medium+10% FCS.

Genomic DNA was harvested and a portion of the Htt locus encompassing the intended cleavage site was PCR amplified. PCR using the Accuprime HiFi polymerase from InVitrogen was performed as follows: after an initial 3 minute denaturation at 94° C., 30 cycles of PCR are performed with a 30 second denaturation step at 94° C. followed by a 30 second annealing step at 58° C. followed by a 30 second extension step at 68° C. After the completion of 30 cycles, the reaction was incubated at 68° C. for 7 minutes, then at 10° C. indefinitely.

The genomic DNA from the K562 Htt-specific ZFN treated cells was examined by the Surveyor™ nuclease (Transgenomic) as described, for example, in U.S. Patent Publication Nos. 2008/0015164; 2008/0131962; and 2008/0159996.

Plasmids encoding the pairs of mouse Htt-specific ZFNs were tested in similar fashion in Neuro-2a cells.

Figure 14A:
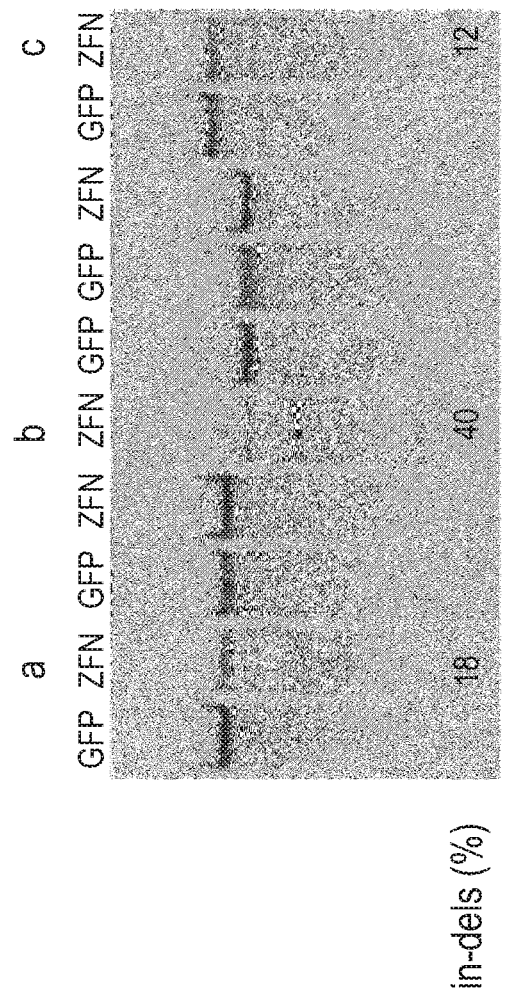
FIGS. 14A and 14B depict the results of Cel-I mismatch assays (Surveyor™, Transgenomics) following treatment of K562 cells with Htt specific ZFN pairs. The percent NHEJ activity (in-del) for an active ZFN is shown at the bottom of the corresponding lane. "GFP" indicates cells that have been transfected with a GFP encoding plasmid.

FIGS. 14A and B show that the ZFNs were capable of targeting the Htt genes with a gene modification efficiency of between 8-40%, assayed as described previously by the amount of indels observed.

Example 17: Targeted Integration of Varying Lengths of Trinucleotide Repeats The Htt-specific ZFNs with the greatest cleaving activity for sequences flanking the CAG repeat as described above are used in a targeted integration strategy to introduce varying lengths of CAG repeat into a wild-type copy of Htt. Donors are constructed that contain 50 (SEQ ID NO: 230), 80 (SEQ ID NO: 231), 109 (SEQ ID NO: 232) and 180 (SEQ ID NO: 233) repeat CAG units. These donors are then transfected into K562 cells with plasmids encoding the Htt-specific ZFNs as described above. Verification of donor integration is achieved by genomic DNA isolation, PCR amplification (as described above) followed by sequencing of the region of interest.

ZFNs identified in the K562 cells which result in targeted integration of the donor alleles into the Htt allele are used to insert the variable length donor nucleic acids into human embryonic stem cells (hESC). Successful donor integration is verified by genomic DNA isolation, PCR and sequencing as described above.

Example 18: Disruption/Knock-Out of Wild-Type and/or Mutant Htt

ZFNs that cleave in early exons can result in small insertion or deletions (in-dels) as a result non-homologous end joining (NHEJ), this can generate cell models with one or both alleles of Htt disrupted, Indicated ZFN pairs were prepared as described above and tested for cleavage activity using the Cel I mismatch as described for Example 8. These ZFN pairs target early exons of human Htt, and thus may be used to knock-out either the wild-type or a mutant Htt allele.

As shown in FIG. 14A, ZFP pairs 29627/29628, 29631/29632 (exon 12) and 29637/29638 (exon 18) cleaved the Htt gene and can thus be utilized for generating knock-out cell lines.

Example 19: Expression Tagging of Wild-Type and HD Htt Alleles

ZFNs with the greatest cleaving activity for the first or last coding exon are used to tag the wild-type and mutant Htt allele with different reporter proteins. Donor DNAs for each reporter (A and B) are designed based on the cleavage site of the lead ZFN pair(s) to allow targeted integration of the reporter gene to produce an in-frame fusion to Htt. Donor DNAs are co-transfected with the lead ZFN pair(s) into K562 cells for selecting the donor DNA construct that gives the highest frequency of integration.

Figure 14B:
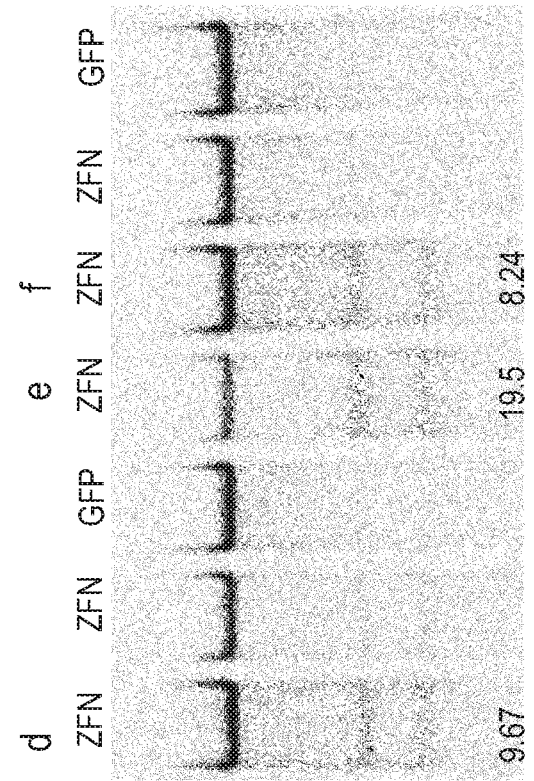

ZFN pairs were prepared as described above and tested for cleavage activity using the Cel I mismatch as described for Example 8. The ZFN pairs used target the 3' end of the Htt coding sequence, and thus may be used to target either a wild-type or a mutant Htt allele. As shown in FIG. 14B, ZFP pairs 25917/25916, 25920/25921 and 25923/25922 were capable of cleaving the Htt gene and can thus be utilized for the introduction of a reporter tag.

The selected donor DNA construct for reporter A along with corresponding ZFNs are delivered to cells derived from subjects carrying mutant Htt gene (e.g. fibroblasts, induced pluripotent cells) Clones are derived and screened for the target integration of the reporter A. Heterozygous events are desired and the targeted alleles are identified by PCR. Clones containing a single reporter-tagged Htt allele and unmodified ZFN target sequence on the other allele are selected; the donor construct for reporter B and corresponding ZFNs are transfected to tag the second allele with the reporter B.

The resulting mouse embryonic stem cell clone contains the wild-type Htt allele and mutant allele tagged with two different markers that allow tracking of expression from each allele; these cells are used to generate mouse models of trinucleotide repeat disorders using standard protocols.

Example 20: Construction of Active TALE-TF Proteins Against Htt

TALE DNA binding domains were linked to the KRAB repression domain from the Kox1 protein (TALE TF) and used to test repression of the Htt gene in HD patient (CAG 20/41 (SEQ ID NOS 248 and 249))-derived fibroblasts. The construction of the TALE proteins was done as described previously (see co-owned U.S. Patent Publication No. 2011/0301073 and co-owned U.S. Pat. No. 9,458,205, both of which are incorporated herein by reference), and were constructed with three different C-terminal architectures: +63, +231 and +278 as described in U.S. Patent Publication No. 2011/0301073. To construct the TALE TF expression plasmids, the TALEN expression plasmids described previously (see U.S. Patent Publication No. 2011/0301073) were used except that the Fok I domain used for in the TALENs was replaced with the KRAB repression domain. The linkages of the C-terminus of the TALE protein and the KRAB domain are shown below, where the KRAB domain sequence is indicated by underline. The bold and italicized text indicates the triple flag tag, the bold text indicates the nuclear localization sequence, "[repeats]" indicates the location of the TALE repeat unit array (full repeats plus the C-terminal half repeat), and the wavy underlined portion shows the sequence of the KRAB domain:

```
TALE-C63-Kox1:
                                                    (SEQ ID NOS 197 & 210)
M*DYKDHDGDYKDHDIDYKDDDDK*MAPKKKRKVGIHGVPMVDLRTGYSQQQQEKIKPKVRSRVAQHHEALVGHGF

THAHIVALSQHPAALGTVAVKYQDMIAALPEATHEAIVGVGKQWSGARALEALLTVAGELRGPPLQLDTGQLLKI

AKRGGVTAVEAVHAWRNALTGAPLN[repeats]GGRPALESIVAQLSRPDPALAALTNDHLVALACLGGRPALD

AVKKGLPHAPALIKRTNRRIPERTSHRVAGSGMDAKSLTAWSRTLVTFKDVFVDFTREEWKLLDTAQQIVYRNVM

LENYKNLVSLGYQLTKPDVILRLEKGEEPWLVEREIHQETHPDSETAFEIKSSV
```

TALE-C63-Kox1:
(SEQ ID NOS 198 & 211)
M*DYKDHDGDYKDHDIDYKDDDDK*MAPKKKRKVGIHGVP<u>MVDLRTLGYSQQQEKIKPKVRSTVAQHHEALVGHGF</u>

<u>THAHIVALSQHPAALGTVAVKYQDMIAALPEATHEAIVGVGKQWSGARALEALLTVAGELRGPPLQLDTGQLLKI</u>

<u>AKRGGVTAVEAVHAWRNALTGAPLN</u>[repeats]GGRPALE<u>SIVAQLSRPDPALAALTNDHLVALACLGGRPALD</u>

<u>AVKKGLPHAPALIKRTNRRIPERTSHRVADHAQVVRVLGFFQCHSHPAQAFDDAMTQFGMSRHGLLQLFRRVGVT</u>

<u>ELEARSGTLPPASQRWDRILQASGMERAKPSPTSTQTPDQASLHAFADSLERDLDAPSPTHEGDQRRASSRKRSR</u>

<u>SDRAVTGPSAQQSFEVRAPEQRDALHLPLSWRVKRPRTSIGGGLPDPGSGMDAKSLTAWSRTLVTFKDVFVDFTR</u>

<u>EEWKLLDTAQQIVYRNVMLENYKNLVSLGYQLTKPDVILRLEKGEEPWLVEREIHQETHPDSETAFEIKSSV</u>

TALE-C278-Kox1
(SEQ ID NOS 199 & 212)
M*DYKDHDGDYKDHDIDYKDDDDK*MAPKKKRKVGIHGVP<u>MVDLRTLGYSQQQEKIKPKVRSTVAQHHEALVGHGE</u>

<u>THAHIVALSQHPAALGTVAVKYQDMIAALPEATHEAIVGVGKQWSGARALEALLTVAGELRGPPLQLDTGQLLKI</u>

<u>AKRGGVTAVEAVHAWRNALTGAPLN</u>[repeats]GGRPALE<u>SIVAQLSRPDPALAALTNDHLVALACLGGRPALD</u>

<u>AVKKGLPHAPALIKRTNRRIPERTSHRVADHAQVVRVLGFFQCHSHPAQAFDDAMTQFGMSRHGLLQLFRRVGVT</u>

<u>ELEARSGTLPPASQRWDRILQASGMERAKPSPTSTQTPDQASLHAFADSLERDLDAPSPTHEGDQRRASSRKRSR</u>

<u>SDRAVTGPSAQQSFEVRAPEQRDALHLPLSWRVKRPRTSIGGGLPDPTPTAADLAASSTVMREQDEDPFAGAADD</u>

<u>FPAFNEEELAWLMELLPQGSGMDAKSLTAWSRTLVTFEDVFVDFTREEWKLLDTAQQIVYRNVMLENYKNLVSLG</u>

<u>YQLTEPDVILRLEKGEEPWLVEREIHQETHPDSETAFEIESSV</u>

Base recognition was achieved using the canonical RVD-base correspondences (the "TALE code": NI for A, HD for C, NN for G (NK in half repeat), NG for T). In some of the TALE TFs, the protein is designed to bind the sense (5'-3') strand of the DNA, while in others, the TALE TF is designed to bind to the anti-sense (3'-5') strand. This set of TALE TFs was designed to target the CAG repeats of the Htt gene. TALE DNA binding proteins often preferentially interact with a 'T' nucleotide base at the 5' end of the target, and so since the targets are CAG repeat regions, it can be predicted that the proteins that bind to the anti-sense DNA strand, and thus CTG repeat sequences with the base 'T' at the 5' 3nd of the target, might have better binding affinity and specificity and thus repressor activity.

The targets and numeric identifiers for the TALE TFs tested are shown below in Table 4. Numeric identifiers are labeled "SBS #", specificity for the Sense or Antisense strand is indicated ("S/A"), as well as the target, the number of repeat units or RVDs and the type of C-terminus.

TABLE 4

Htt specific TALE-TFs

| SBS# | S/A | Target (5'-3') | SEQ ID NO | RVDs | C term |
|---|---|---|---|---|---|
| 102449 | S | gcAGCAGCAGCAGCAGCAGca | 200 | 17 | +63 |
| 102450 | S | gcAGCAGCAGCAGCAGca | 201 | 14 | +63 |
| 102451 | S | gcAGCAGCAGCAGca | 202 | 11 | +63 |
| 102452 | S | gcAGCAGCAGca | 203 | 8 | +63 |
| 102453 | A | ctGCTGCTGCTGCTGCTGctg | 204 | 17 | +63 |
| 102454 | A | ctGCTGCTGCTGCTGctg | 205 | 14 | +63 |
| 102455 | A | ctGCTGCTGCTGctg | 206 | 11 | +63 |
| 102456 | A | ctGCTGCTGctg | 207 | 8 | +63 |
| 102457 | S | gcAGCAGCAGCAGCAGCAGca | 200 | 17 | +231 |
| 102458 | S | gcAGCAGCAGCAGCAGca | 201 | 14 | +231 |
| 102459 | S | gcAGCAGCAGCAGca | 202 | 11 | +231 |
| 102460 | S | gcAGCAGCAGca | 203 | 8 | +231 |

TABLE 4-continued

Htt specific TALE-TFs

| SBS# | S/A | Target (5'-3') | SEQ ID NO | RVDs | C term |
|---|---|---|---|---|---|
| 102462 | A | ctGCTGCTGCTGCTGCtg | 205 | 14 | +231 |
| 102463 | A | ctGCTGCTGCTGCtg | 206 | 11 | +231 |
| 102464 | A | ctGCTGCTGCtg | 207 | 8 | +231 |
| 102466 | S | gcAGCAGCAGCAGCAGca | 201 | 14 | +278 |
| 102467 | S | gcAGCAGCAGCAGca | 202 | 11 | +278 |
| 102468 | S | gcAGCAGCAGca | 203 | 8 | +278 |
| 102469 | A | ctGCTGCTGCTGCTGCTGCtg | 204 | 17 | +278 |
| 102470 | A | ctGCTGCTGCTGCTGCtg | 205 | 14 | +278 |
| 102471 | A | ctGCTGCTGCTGCtg | 206 | 11 | +278 |
| 102472 | A | ctGCTGCTGCtg | 207 | 8 | +278 |

Figure 15:
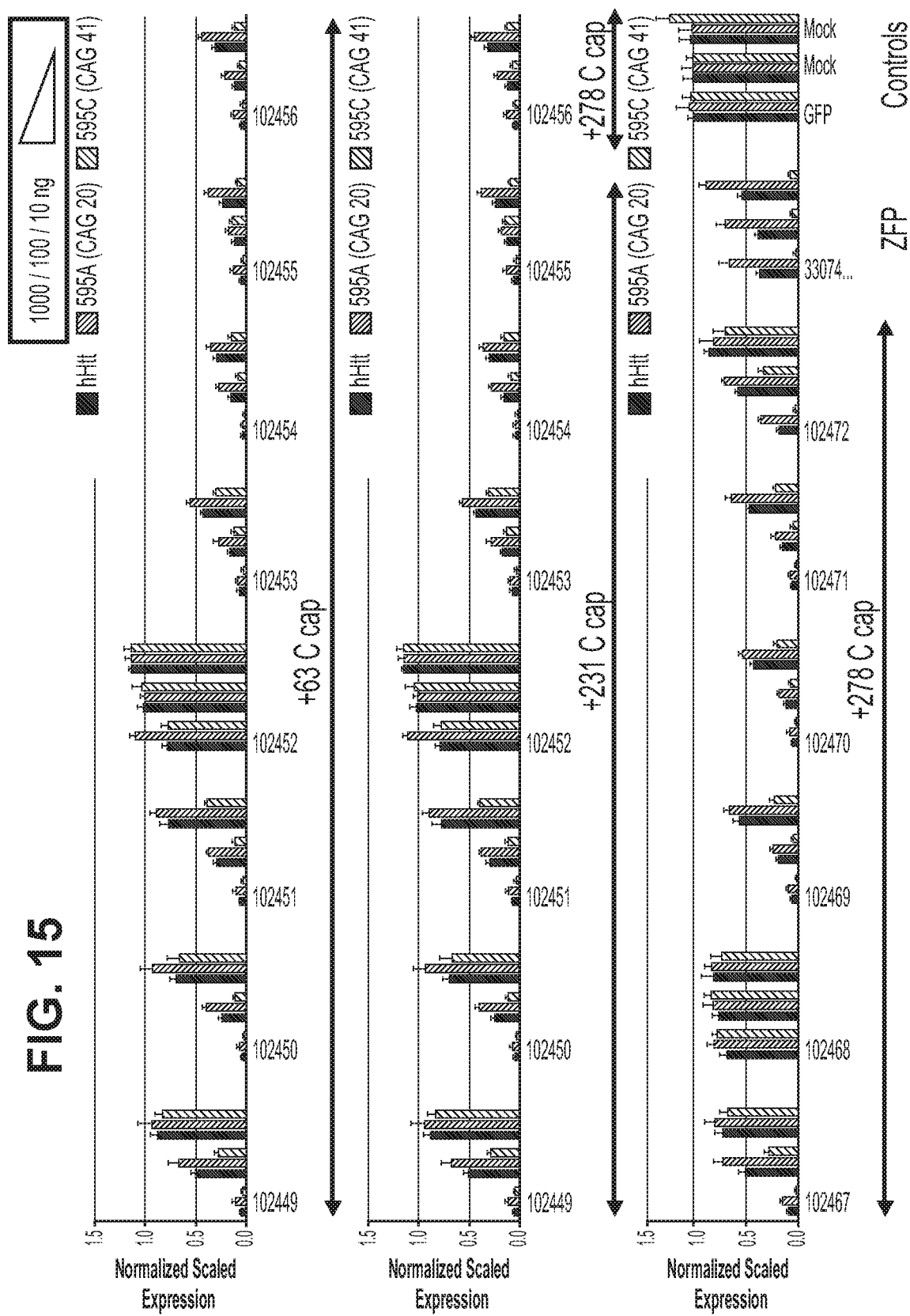
FIG. 15 depicts graphs of the Htt repression results for several candidate TALE-TF proteins. The TALE-TFs were tested in HD patient derived fibroblasts (CAG 20/41 (SEQ ID NOS 248 and 246)). The results demonstrate that some of the TALE TFs were active in repressing overall Htt expression, while others exhibited mutant Htt-preferential repression.

The TALE TFs in the table were then tested for Htt repression in HD patient (CAG 20/41 (SEQ ID NOS 248 and 249)) derived fibroblasts, and the results are shown in FIG. 15. In this experiment, the cells were transfected with either 1000, 100 or 10 ng of TALE-TF encoding mRNA. The results for each TALE TF assayed are shown in groups of three, representing the three transfected mRNA amounts. In each grouping, there are also three samples: the left bar indicates the total Htt expression, the middle bar indicates the expression from the CAG20 (SEQ ID NO: 248) Htt allele, and the right bar indicates the expression from the CAG41 (SEQ ID NO: 249) Htt allele. The data demonstrates that there are some TALE TFs that were able to repress both Htt alleles (see for example 102454), while other TALE TFs were able to selectively inhibit the mutant Htt with the extended CAG repeat (see for example 102451 and 102472).

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. An mRNA encoding a fusion protein comprising a transcriptional repression domain and a non-naturally occurring zinc finger protein comprising 6 zinc finger domains ordered F1 to F6, respectively, wherein the zinc finger protein specifically binds to mutant Huntington's gene allele (mHtt) gene and comprises the recognition helix regions as follows:

F1: RSDNLSE; (SEQ ID NO: 60)

F2: KRCNLRC; (SEQ ID NO: 61)

F3: QSGDLTR; (SEQ ID NO: 18)

F4: QSGDLTR; (SEQ ID NO: 18)

F5: RSDNLSE; (SEQ ID NO: 60)

and

F6: KRCNLRC. (SEQ ID NO: 61)

2. The mRNA of claim 1, wherein the zinc finger protein binds to sequences within the CAG repeat region of the mHtt gene.

3. A host cell comprising one or more mRNAs of claim 1.

4. A method of modifying expression of an mHtt gene in a cell, the method comprising administering to the cell one or more polynucleotides encoding one or more mRNAs according to claim 1.

5. A method of treating Huntington's Disease, the method comprising administering one or more mRNAs according to claim 1 to a subject in need thereof.

6. A pharmaceutical composition comprising one or more mRNAs according to claim 1.

7. A method of treating Huntington's Disease, the method comprising administering the pharmaceutical composition according to claim 6 to a subject in need thereof.

* * * * *

SEQUENCE LISTING

```
<160> NUMBER OF SEQ ID NOS: 261

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Ser Asp Asp Leu Ser Arg
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Asn Asp Asn Arg Thr Lys
1               5

<210> SEQ ID NO 3
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Ser Asp Asp Leu Thr Arg
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ser Asp Asp Arg Lys Thr
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Ser Ala Asp Leu Thr Arg
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Ser Ser Asp Leu Arg Arg
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Ser Asp Asn Leu Ala Arg
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Trp Arg Gly Asp Arg Val Lys
```

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asp Arg Ser Asn Leu Ser Arg
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Thr Ser Gly Ser Leu Thr Arg
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Glu Arg Gly Thr Leu Ala Arg
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Ser Asp Ala Leu Ser Arg
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Arg Ser His Leu Ala Arg
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 14

Arg Ser Asp His Leu Ser Arg
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Ser Ser Asp Leu Thr Arg
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Thr Ser Gly Asn Leu Thr Arg
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gln Ser Gly His Leu Gln Arg
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Ser Gly Asp Leu Thr Arg
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Ser Asp Val Leu Ser Thr
1               5

<210> SEQ ID NO 20

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Val Arg Ser Arg Leu Arg Arg
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asp Arg Ser Thr Leu Arg Gln
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asp Arg Ser Asp Leu Ser Arg
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gln Ser Ser Thr Arg Ala Arg
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Ser Asp Thr Leu Ser Glu
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25
```

```
His Arg Arg Ser Arg Trp Gly
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Arg Asp Thr Leu Arg Ser
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Ser Asp His Leu Ser Thr
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gln Ser Ala His Arg Ile Thr
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Ser Asp His Leu Ser Glu
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gln Asn Ala His Arg Lys Thr
1               5

<210> SEQ ID NO 31
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 31

Gln Ser Ser Asp Leu Ser Arg
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

His Arg Ser Thr Arg Asn Arg
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Leu Arg Gln Asp Leu Lys Arg
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asp Arg Ser His Leu Thr Arg
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Asp Arg Ser Asn Leu Thr Arg
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Leu Lys Gln Met Leu Ala Val
1               5
```

```
<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Ser Asp Ser Leu Ser Ala
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Arg Ser Asp Ala Leu Ser Thr
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Asp Arg Ser Thr Arg Thr Lys
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asp Arg Ser Ala Leu Ala Arg
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gln Ser Gly His Leu Ser Arg
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42
```

Arg Ser Asp Val Leu Ser Glu
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Thr Ser Gly His Leu Ser Arg
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Lys Leu Cys Asn Arg Lys Cys
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

His Arg Thr Ser Leu Thr Asp
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Ser Ala His Leu Ser Arg
1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gln Ser Gly Asn Leu Ala Arg
1               5

<210> SEQ ID NO 48
<211> LENGTH: 7
<212> TYPE: PRT
<213> ORGANISM: Artificial Sequence -continued

```
<220> FEATURE:
<223> OTHER INFORMATION: Description of Artificial Sequence: Synthetic
      peptide

<400> SEQUENCE: 48

Leu Lys His His Leu Thr Asp
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Tyr Arg Trp Leu Arg Asn Asn
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Arg Ser Asp His Leu Ser Gln
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Arg Ser Ala Val Arg Lys Asn
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Trp Ser Thr Ser Leu Arg Ala
1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gln Arg Thr His Leu Thr Gln
1               5
```

```
<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Arg Ser Ser His Leu Ser Arg
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Thr Ser Gly Ser Leu Ser Arg
1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Thr Arg Gln Asn Arg Asp Thr
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Asp Gln Ser Thr Leu Arg Asn
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Arg Ser Ala Ala Leu Ser Arg
1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 59

Arg Ser Asp Ala Leu Ala Arg
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Arg Ser Asp Asn Leu Ser Glu
1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Lys Arg Cys Asn Leu Arg Cys
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Trp Arg Ser Cys Arg Ser Ala
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gln Trp Ser Thr Arg Lys Arg
1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Arg Arg Trp Thr Leu Val Gly
1               5

<210> SEQ ID NO 65
<211> LENGTH: 7
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 65

Arg Ser Asp Asn Leu Arg Glu
1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Tyr Arg Trp Leu Leu Arg Ser
1               5

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Arg Lys Asp Ala Leu Val Ala
1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Arg Arg Ala Asp Leu Ser Arg
1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Leu Ala Gln Pro Arg Asn Lys
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Arg Ser Asp His Leu Ser Ala
1               5

```
<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Arg Ser Ala Asp Arg Thr Arg
1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Thr Ser Ser Asp Arg Lys Lys
1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Arg Ser Ala Asn Leu Ala Arg
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

His His Ser Ala Arg Arg Cys
1               5

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Asp Asn Ser Ser Arg Thr Arg
1               5

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 76

His Lys Gln His Arg Asp Ala
1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Arg Arg Thr Asp Leu Arg Arg
1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Asp Pro Ser Asn Arg Val Gly
1               5

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Arg Ser Ala Asp Leu Ser Arg
1               5

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Arg Asn Asp Asp Arg Lys Lys
1               5

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gln Lys Val Thr Leu Ala Ala
1               5

<210> SEQ ID NO 82
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Arg Arg Ser Thr Leu Arg Ser
1               5

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Asp Arg Ser Ala Leu Ser Arg
1               5

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gln Ser Gly Ser Leu Thr Arg
1               5

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Leu Lys Trp Asn Leu Arg Thr
1               5

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Leu Lys Trp Asp Arg Gln Thr
1               5

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Asp Arg Ser His Leu Ser Arg
```

<210> SEQ ID NO 88
<211> LENGTH: 28
<212> TYPE: DNA
<213> ORGANISM: Unknown
<220> FEATURE:
<223> OTHER INFORMATION: Description of Unknown: Human or mouse
      target sequence

<400> SEQUENCE: 88
acgctgcgcc ggcggaggcg gggccgcg                                        28

<210> SEQ ID NO 89
<211> LENGTH: 28
<212> TYPE: DNA
<213> ORGANISM: Unknown
<220> FEATURE:
<223> OTHER INFORMATION: Description of Unknown: Human or mouse
      target sequence

<400> SEQUENCE: 89
agccggccgt ggactctgag ccgaggtg                                        28

<210> SEQ ID NO 90
<211> LENGTH: 28
<212> TYPE: DNA
<213> ORGANISM: Unknown
<220> FEATURE:
<223> OTHER INFORMATION: Description of Unknown: Human or mouse
      target sequence

<400> SEQUENCE: 90
gtggcgatgc gggggcgtg gtgaggta                                         28

<210> SEQ ID NO 91
<211> LENGTH: 28
<212> TYPE: DNA
<213> ORGANISM: Unknown
<220> FEATURE:
<223> OTHER INFORMATION: Description of Unknown: Human or mouse
      target sequence

<400> SEQUENCE: 91
ccgggacggg tccaagatgg acggccgc                                        28

<210> SEQ ID NO 92
<211> LENGTH: 28
<212> TYPE: DNA
<213> ORGANISM: Unknown
<220> FEATURE:
<223> OTHER INFORMATION: Description of Unknown: Human or mouse
      target sequence

<400> SEQUENCE: 92
ccgtcccggc agcccccacg gcgccttg                                        28

<210> SEQ ID NO 93
<211> LENGTH: 28
<212> TYPE: DNA
<213> ORGANISM: Unknown
<220> FEATURE:
<223> OTHER INFORMATION: Description of Unknown: Human or mouse
      target sequence

<400> SEQUENCE: 93
cgggtccaag atggacggcc gctcaggt                                        28

```
<210> SEQ ID NO 94
<211> LENGTH: 28
<212> TYPE: DNA
<213> ORGANISM: Unknown
<220> FEATURE:
<223> OTHER INFORMATION: Description of Unknown: Human or mouse
      target sequence

<400> SEQUENCE: 94
ctgctgctgc tgctggaagg acttgagg                                              28

<210> SEQ ID NO 95
<211> LENGTH: 28
<212> TYPE: DNA
<213> ORGANISM: Unknown
<220> FEATURE:
<223> OTHER INFORMATION: Description of Unknown: Human or mouse
      target sequence

<400> SEQUENCE: 95
tcagatggga cggcgctgac ctggctgg                                              28

<210> SEQ ID NO 96
<211> LENGTH: 28
<212> TYPE: DNA
<213> ORGANISM: Unknown
<220> FEATURE:
<223> OTHER INFORMATION: Description of Unknown: Human or mouse
      target sequence

<400> SEQUENCE: 96
ctgccatgga cctgaatgat gggaccca                                              28

<210> SEQ ID NO 97
<211> LENGTH: 28
<212> TYPE: DNA
<213> ORGANISM: Unknown
<220> FEATURE:
<223> OTHER INFORMATION: Description of Unknown: Human or mouse
      target sequence

<400> SEQUENCE: 97
gtggtctggg agctgtcgct gatgggcg                                              28

<210> SEQ ID NO 98
<211> LENGTH: 28
<212> TYPE: DNA
<213> ORGANISM: Unknown
<220> FEATURE:
<223> OTHER INFORMATION: Description of Unknown: Human or mouse
      target sequence

<400> SEQUENCE: 98
ccgaagggcc tgattcagct gttacccc                                              28

<210> SEQ ID NO 99
<211> LENGTH: 28
<212> TYPE: DNA
<213> ORGANISM: Unknown
<220> FEATURE:
<223> OTHER INFORMATION: Description of Unknown: Human or mouse
      target sequence

<400> SEQUENCE: 99
aacttgcaag taacagaaga ctcatcct                                              28
```

<210> SEQ ID NO 100
<211> LENGTH: 28
<212> TYPE: DNA
<213> ORGANISM: Unknown
<220> FEATURE:
<223> OTHER INFORMATION: Description of Unknown: Human or mouse
      target sequence

<400> SEQUENCE: 100
cttgtacagc tgtgagggtg agcataat                                      28

<210> SEQ ID NO 101
<211> LENGTH: 28
<212> TYPE: DNA
<213> ORGANISM: Unknown
<220> FEATURE:
<223> OTHER INFORMATION: Description of Unknown: Human or mouse
      target sequence

<400> SEQUENCE: 101
gccatggtgg gagagactgt gaggcggc                                      28

<210> SEQ ID NO 102
<211> LENGTH: 28
<212> TYPE: DNA
<213> ORGANISM: Unknown
<220> FEATURE:
<223> OTHER INFORMATION: Description of Unknown: Human or mouse
      target sequence

<400> SEQUENCE: 102
ctcagcaggt ggtgaccttg tggacatt                                      28

<210> SEQ ID NO 103
<211> LENGTH: 28
<212> TYPE: DNA
<213> ORGANISM: Unknown
<220> FEATURE:
<223> OTHER INFORMATION: Description of Unknown: Human or mouse
      target sequence

<400> SEQUENCE: 103
gcgctcagca ggtggtgacc ttgtggac                                      28

<210> SEQ ID NO 104
<211> LENGTH: 28
<212> TYPE: DNA
<213> ORGANISM: Unknown
<220> FEATURE:
<223> OTHER INFORMATION: Description of Unknown: Human or mouse
      target sequence

<400> SEQUENCE: 104
atggtgggag agactgtgag gcggcagc                                      28

<210> SEQ ID NO 105
<211> LENGTH: 28
<212> TYPE: DNA
<213> ORGANISM: Unknown
<220> FEATURE:
<223> OTHER INFORMATION: Description of Unknown: Human or mouse
      target sequence

<400> SEQUENCE: 105
tgggagagac tgtgaggcgg cagctggg                                      28

-continued

```
<210> SEQ ID NO 106
<211> LENGTH: 28
<212> TYPE: DNA
<213> ORGANISM: Unknown
<220> FEATURE:
<223> OTHER INFORMATION: Description of Unknown: Human or mouse
      target sequence

<400> SEQUENCE: 106
atggcgctca gcaggtggtg accttgtg                                      28

<210> SEQ ID NO 107
<211> LENGTH: 28
<212> TYPE: DNA
<213> ORGANISM: Unknown
<220> FEATURE:
<223> OTHER INFORMATION: Description of Unknown: Human or mouse
      target sequence

<400> SEQUENCE: 107
cagcagcagc agcagcagca gcagcagc                                      28

<210> SEQ ID NO 108
<211> LENGTH: 28
<212> TYPE: DNA
<213> ORGANISM: Unknown
<220> FEATURE:
<223> OTHER INFORMATION: Description of Unknown: Human or mouse
      target sequence

<400> SEQUENCE: 108
ctgctgctgc tgctgctgct ggaaggac                                      28

<210> SEQ ID NO 109
<211> LENGTH: 28
<212> TYPE: DNA
<213> ORGANISM: Unknown
<220> FEATURE:
<223> OTHER INFORMATION: Description of Unknown: Human or mouse
      target sequence

<400> SEQUENCE: 109
tgctgctgct gctgctgctg ctggaagg                                      28

<210> SEQ ID NO 110
<211> LENGTH: 28
<212> TYPE: DNA
<213> ORGANISM: Unknown
<220> FEATURE:
<223> OTHER INFORMATION: Description of Unknown: Human or mouse
      target sequence

<400> SEQUENCE: 110
agcagcagca gcagcagcag cagcagca                                      28

<210> SEQ ID NO 111
<211> LENGTH: 28
<212> TYPE: DNA
<213> ORGANISM: Unknown
<220> FEATURE:
<223> OTHER INFORMATION: Description of Unknown: Human or mouse
      target sequence

<400> SEQUENCE: 111
tgctgctgct gctgctgctg ctggaagg                                      28

<210> SEQ ID NO 112
```

```
<211> LENGTH: 28
<212> TYPE: DNA
<213> ORGANISM: Unknown
<220> FEATURE:
<223> OTHER INFORMATION: Description of Unknown: Human or mouse
      target sequence

<400> SEQUENCE: 112
ggctggcttt tgcgggaagg ggcggggc                                          28

<210> SEQ ID NO 113
<211> LENGTH: 28
<212> TYPE: DNA
<213> ORGANISM: Unknown
<220> FEATURE:
<223> OTHER INFORMATION: Description of Unknown: Human or mouse
      target sequence

<400> SEQUENCE: 113
gaattgacag gcggatgcgt cgtcctct                                          28

<210> SEQ ID NO 114
<211> LENGTH: 28
<212> TYPE: DNA
<213> ORGANISM: Unknown
<220> FEATURE:
<223> OTHER INFORMATION: Description of Unknown: Human or mouse
      target sequence

<400> SEQUENCE: 114
attctgcggg tctggcgtgg cctcgtct                                          28

<210> SEQ ID NO 115
<211> LENGTH: 28
<212> TYPE: DNA
<213> ORGANISM: Unknown
<220> FEATURE:
<223> OTHER INFORMATION: Description of Unknown: Human or mouse
      target sequence

<400> SEQUENCE: 115
gtgacgtcat gccggcggag acgaggcc                                          28

<210> SEQ ID NO 116
<211> LENGTH: 28
<212> TYPE: DNA
<213> ORGANISM: Unknown
<220> FEATURE:
<223> OTHER INFORMATION: Description of Unknown: Human or mouse
      target sequence

<400> SEQUENCE: 116
gtgcgtcccg tgacgtcatg ccggcgga                                          28

<210> SEQ ID NO 117
<211> LENGTH: 28
<212> TYPE: DNA
<213> ORGANISM: Unknown
<220> FEATURE:
<223> OTHER INFORMATION: Description of Unknown: Human or mouse
      target sequence

<400> SEQUENCE: 117
gccgcgaggg ttgccgggac gggcccaa                                          28

<210> SEQ ID NO 118
<211> LENGTH: 28
```

```
<212> TYPE: DNA
<213> ORGANISM: Unknown
<220> FEATURE:
<223> OTHER INFORMATION: Description of Unknown: Human or mouse
      target sequence

<400> SEQUENCE: 118
ccgcgagggt tgccgggacg ggcccaag                                            28

<210> SEQ ID NO 119
<211> LENGTH: 28
<212> TYPE: DNA
<213> ORGANISM: Unknown
<220> FEATURE:
<223> OTHER INFORMATION: Description of Unknown: Human or mouse
      target sequence

<400> SEQUENCE: 119
catcgggcag gaagccgtca tggcaacc                                            28

<210> SEQ ID NO 120
<211> LENGTH: 28
<212> TYPE: DNA
<213> ORGANISM: Unknown
<220> FEATURE:
<223> OTHER INFORMATION: Description of Unknown: Human or mouse
      target sequence

<400> SEQUENCE: 120
tcctgcccga tgggacagac cctgaaga                                            28

<210> SEQ ID NO 121
<211> LENGTH: 28
<212> TYPE: DNA
<213> ORGANISM: Unknown
<220> FEATURE:
<223> OTHER INFORMATION: Description of Unknown: Human or mouse
      target sequence

<400> SEQUENCE: 121
gtactgagca atgctgtagt cagcaatc                                            28

<210> SEQ ID NO 122
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Thr Lys Cys Val His Cys Gly Ile Val Phe Leu Asp Glu Val Met Tyr
1               5                   10                  15

Ala Leu His Met Ser Cys His Gly Phe Arg Asp Pro Phe Glu Cys Asn
            20                  25                  30

Ile Cys Gly Tyr His Ser Gln Asp Arg Tyr Glu Phe Ser Ser His Ile
        35                  40                  45

Val Arg Gly Glu His
    50

<210> SEQ ID NO 123
<211> LENGTH: 53
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 123

Phe Lys Cys Glu His Cys Arg Ile Leu Phe Leu Asp His Val Met Phe
1               5                   10                  15

Thr Ile His Met Gly Cys His Gly Phe Arg Asp Pro Phe Lys Cys Asn
            20                  25                  30

Met Cys Gly Glu Lys Cys Asp Gly Pro Val Gly Leu Phe Val His Met
        35                  40                  45

Ala Arg Asn Ala His
    50

<210> SEQ ID NO 124
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

His His Cys Gln His Cys Asp Met Tyr Phe Ala Asp Asn Ile Leu Tyr
1               5                   10                  15

Thr Ile His Met Gly Cys His Gly Tyr Glu Asn Pro Phe Glu Cys Asn
            20                  25                  30

Ile Cys Gly Tyr His Ser Gln Asp Arg Tyr Glu Phe Ser Ser His Ile
        35                  40                  45

Val Arg Gly Glu His
    50

<210> SEQ ID NO 125
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

His His Cys Gln His Cys Asp Met Tyr Phe Ala Asp Asn Ile Leu Tyr
1               5                   10                  15

Thr Ile His Met Gly Cys His Ser Cys Asp Asp Val Phe Lys Cys Asn
            20                  25                  30

Met Cys Gly Glu Lys Cys Asp Gly Pro Val Gly Leu Phe Val His Met
        35                  40                  45

Ala Arg Asn Ala His Gly Glu Lys Pro Thr Lys Cys Val His Cys Gly
    50                  55                  60

Ile Val Phe Leu Asp Glu Val Met Tyr Ala Leu His Met Ser Cys His
65                  70                  75                  80

Gly Phe Arg Asp Pro Phe Glu Cys Asn Ile Cys Gly Tyr His Ser Gln
                85                  90                  95

Asp Arg Tyr Glu Phe Ser Ser His Ile Val Arg Gly Glu His
                100                 105                 110

<210> SEQ ID NO 126
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Phe Lys Cys Glu His Cys Arg Ile Leu Phe Leu Asp His Val Met Phe
1               5                   10                  15

Thr Ile His Met Gly Cys His Gly Phe Arg Asp Pro Phe Lys Cys Asn
            20                  25                  30

Met Cys Gly Glu Lys Cys Asp Gly Pro Val Gly Leu Phe Val His Met
        35                  40                  45

Ala Arg Asn Ala His Gly Glu Lys Pro Phe Tyr Cys Glu His Cys Glu
    50                  55                  60

Ile Thr Phe Arg Asp Val Val Met Tyr Ser Leu His Lys Gly Tyr His
65                  70                  75                  80

Gly Phe Arg Asp Pro Phe Glu Cys Asn Ile Cys Gly Tyr His Ser Gln
                85                  90                  95

Asp Arg Tyr Glu Phe Ser Ser His Ile Val Arg Gly Glu His
            100                 105                 110

<210> SEQ ID NO 127
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Ala Gln Leu Glu Lys Glu Leu Gln Ala Leu Glu Lys Lys Leu Ala Gln
1               5                   10                  15

Leu Glu Trp Glu Asn Gln Ala Leu Glu Lys Glu Leu Ala Gln
            20                  25                  30

<210> SEQ ID NO 128
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Ala Gln Leu Lys Lys Lys Leu Gln Ala Asn Lys Lys Glu Leu Ala Gln
1               5                   10                  15

Leu Lys Trp Lys Leu Gln Ala Leu Lys Lys Lys Leu Ala Gln
            20                  25                  30

<210> SEQ ID NO 129
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Glu Gln Leu Glu Lys Lys Leu Gln Ala Leu Glu Lys Lys Leu Ala Gln
1               5                   10                  15

Leu Glu Trp Lys Asn Gln Ala Leu Glu Lys Lys Leu Ala Gln
            20                  25                  30

<210> SEQ ID NO 130
<211> LENGTH: 29
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 130

Ala Leu Lys Lys Glu Leu Gln Ala Asn Lys Lys Glu Leu Ala Gln Leu
1               5                   10                  15

Lys Trp Glu Leu Gln Ala Leu Lys Lys Glu Leu Ala Gln
            20                  25

<210> SEQ ID NO 131
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Glu Gln Leu Glu Lys Lys Leu Gln Ala Leu Glu Lys Lys Leu Ala Gln
1               5                   10                  15

Leu Glu Trp Lys Asn Gln Ala Leu Glu Lys
            20                  25

<210> SEQ ID NO 132
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Glu Leu Gln Ala Asn Lys Lys Glu Leu Ala Gln Leu Lys Trp Glu Leu
1               5                   10                  15

Gln Ala Leu Lys Lys Glu Leu Ala Gln
            20                  25

<210> SEQ ID NO 133
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Glu Gln Leu Glu Lys Lys Leu Gln Ala Leu Glu Lys Lys Leu Ala Gln
1               5                   10                  15

Leu Glu Trp Lys Asn Gln Ala
            20

<210> SEQ ID NO 134
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Gln Ala Asn Lys Lys Glu Leu Ala Gln Leu Lys Trp Glu Leu Gln Ala
1               5                   10                  15

Leu Lys Lys Glu Leu Ala Gln

```
<210> SEQ ID NO 135
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Thr Gly Glu Lys Pro
1               5

<210> SEQ ID NO 136
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Thr Gly Gly Gln Arg Pro
1               5

<210> SEQ ID NO 137
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Thr Gly Gln Lys Pro
1               5

<210> SEQ ID NO 138
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Thr Gly Ser Gln Lys Pro
1               5

<210> SEQ ID NO 139
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
gaagatctca cttggggtcc tcaggtcgtg ccgac                               35

<210> SEQ ID NO 140
<211> LENGTH: 41
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 140
gtatccaagc ttcagctttt ccagggtcgc ctaggcggtc t                41

<210> SEQ ID NO 141
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
gcctaggcga ccctggaaaa gctgatgaag gcc                33

<210> SEQ ID NO 142
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
gtatccaagc ttgagctgca gcgggcccaa actcacg                37

<210> SEQ ID NO 143
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
agtttggagg gtttctc                17

<210> SEQ ID NO 144
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
tcgactaaag caggatttca gg                22

<210> SEQ ID NO 145
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
agtttggagg gtttctt                17

<210> SEQ ID NO 146
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 146
agggtttctc cgctcagc                                                    18

<210> SEQ ID NO 147
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Gln Ser Gly Ala Leu Ala Arg
1               5

<210> SEQ ID NO 148
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Arg Ser Ala Val Leu Ser Glu
1               5

<210> SEQ ID NO 149
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Arg Ser Asp Asp Leu Ser Lys
1               5

<210> SEQ ID NO 150
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Asp Asn Ser Asn Arg Ile Lys
1               5

<210> SEQ ID NO 151
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Asp Asp Ser His Arg Lys Asp
1               5

<210> SEQ ID NO 152
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 152

Arg Ser Asp His Leu Thr Gln
1               5

<210> SEQ ID NO 153
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Arg Ser Asp Ser Leu Leu Arg
1               5

<210> SEQ ID NO 154
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Arg Arg Asp Trp Leu Pro Gln
1               5

<210> SEQ ID NO 155
<211> LENGTH: 28
<212> TYPE: DNA
<213> ORGANISM: Unknown
<220> FEATURE:
<223> OTHER INFORMATION: Description of Unknown: Human or mouse
      target sequence

<400> SEQUENCE: 155
cgcactcgcc gcgagggttg ccgggacg                                           28

<210> SEQ ID NO 156

<400> SEQUENCE: 156

000

<210> SEQ ID NO 157
<211> LENGTH: 28
<212> TYPE: DNA
<213> ORGANISM: Unknown
<220> FEATURE:
<223> OTHER INFORMATION: Description of Unknown: Human or mouse
      target sequence

<400> SEQUENCE: 157
agcagcagca gcagcagcag cagcagca                                           28

<210> SEQ ID NO 158
<211> LENGTH: 28
<212> TYPE: DNA
<213> ORGANISM: Unknown
<220> FEATURE:
<223> OTHER INFORMATION: Description of Unknown: Human or mouse
      target sequence
```

<400> SEQUENCE: 158
ctgctgctgc tgctgctgct gctggaag    28

<210> SEQ ID NO 159
<211> LENGTH: 28
<212> TYPE: DNA
<213> ORGANISM: Unknown
<220> FEATURE:
<223> OTHER INFORMATION: Description of Unknown: Human or mouse
      target sequence

<400> SEQUENCE: 159
cctgtccaga gggtcgcggt acctccct    28

<210> SEQ ID NO 160
<211> LENGTH: 28
<212> TYPE: DNA
<213> ORGANISM: Unknown
<220> FEATURE:
<223> OTHER INFORMATION: Description of Unknown: Human or mouse
      target sequence

<400> SEQUENCE: 160
tgccggacct ggcagcggcg gtggtggc    28

<210> SEQ ID NO 161
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Arg Ser Asp Asn Leu Ser Glu Lys Arg Cys Asn Leu Arg Cys
1               5                   10

<210> SEQ ID NO 162
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Arg Ser Asp Asn Leu Ser Glu Lys Pro Tyr Asn Leu Arg Thr
1               5                   10

<210> SEQ ID NO 163
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Arg Ser Asp Asn Leu Ser Glu Arg Leu Trp Asn Arg Lys Gln
1               5                   10

<210> SEQ ID NO 164
<211> LENGTH: 14
<212> TYPE: PRT
<213> ORGANISM: Artificial Sequence
<220> FEATURE:
<223> OTHER INFORMATION: Description of Artificial Sequence: Synthetic

```
                                                    -continued
      peptide

<400> SEQUENCE: 164

Arg Ser Asp Asn Leu Ser Val Arg Arg Trp Asn Leu Arg Ala
1               5                   10

<210> SEQ ID NO 165
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Arg Ser Asp Asn Leu Ser Val Arg Lys Trp Asn Arg Asp Ser
1               5                   10

<210> SEQ ID NO 166
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Arg Ser Asp Asn Leu Ser Glu Asn Thr Ser Pro Leu Met Leu
1               5                   10

<210> SEQ ID NO 167
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Arg Ser Asp Asn Leu Ser Glu Arg Arg Tyr Asn Leu Val Lys
1               5                   10

<210> SEQ ID NO 168
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Arg Ser Asp Thr Leu Ser Glu Arg Arg Trp Thr Leu Val Gly
1               5                   10

<210> SEQ ID NO 169
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Gln Ser Ser Asp Leu Ser Arg Gln Trp Ser Thr Arg Lys Arg
1               5                   10

<210> SEQ ID NO 170
```

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Arg Ser Ala His Leu Ser Arg Gln Ser Gly Asp Leu Thr Arg
1               5                   10

<210> SEQ ID NO 171
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Gln Ser Gly Asp Leu Thr Arg Gln Ser Gly Asp Leu Thr Arg
1               5                   10

<210> SEQ ID NO 172
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Gln Ser Gly Asp Leu Thr Arg Gln Ser Ser Asp Leu Arg Arg
1               5                   10

<210> SEQ ID NO 173
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Gln Ser Ser Asp Leu Ser Arg Gln Ser Ser Asp Leu Arg Arg
1               5                   10

<210> SEQ ID NO 174
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Gln Ser Ser Asp Leu Ser Arg His Arg Ser Thr Arg Asn Arg
1               5                   10

<210> SEQ ID NO 175
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175
```

```
Met Ala Cys Cys Arg Tyr Ala
1               5
```

<210> SEQ ID NO 176
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

```
Arg Ser Ala Asn Leu Arg Glu
1               5
```

<210> SEQ ID NO 177
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

```
Arg Asn Ala Asp Arg Lys Lys
1               5
```

<210> SEQ ID NO 178
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

```
Gln Asn Ala Thr Arg Ile Lys
1               5
```

<210> SEQ ID NO 179
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

```
Leu Arg Gln Lys Asp Ala Ala Arg Gly Ser Ala Ala Met Ala Glu Arg
1               5                   10                  15

Pro Phe Gln
```

<210> SEQ ID NO 180
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

```
Met Ala Pro Lys Lys Lys Arg Lys Val Gly Ile His Gly Val Leu Arg
1               5                   10                  15

Gly Ala Ala Thr Lys Cys Val His Cys Gly Ile Val Phe Leu Asp Glu
                20                  25                  30

Val Met Tyr Ala Leu His Met Ser Cys His Gly Phe Arg Asp Pro Phe
```

```
                 35                  40                  45

Glu Cys Asn Ile Cys Gly Tyr His Ser Gln Asp Arg Tyr Glu Phe Ser
             50                  55                  60

Ser His Ile Val Arg Gly Glu His Ser Gly Val Pro
 65                  70                  75

<210> SEQ ID NO 181
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Met Ala Pro Lys Lys Arg Lys Val Gly Ile His Gly Val Leu Arg
 1               5                  10                  15

Gly Ala Ala Phe Lys Cys Glu His Cys Arg Ile Leu Phe Leu Asp His
                 20                  25                  30

Val Met Phe Thr Ile His Met Gly Cys His Gly Phe Arg Asp Pro Phe
             35                  40                  45

Lys Cys Asn Met Cys Gly Glu Lys Cys Asp Gly Pro Val Gly Leu Phe
         50                  55                  60

Val His Met Ala Arg Asn Ala His Ser Gly Val Pro
 65                  70                  75

<210> SEQ ID NO 182
<211> LENGTH: 76
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Met Ala Pro Lys Lys Arg Lys Val Gly Ile His Gly Val Leu Arg
 1               5                  10                  15

Gly Ala Ala Phe Lys Cys Glu His Cys Arg Ile Leu Phe Leu Asp His
                 20                  25                  30

Val Met Phe Thr Ile His Met Gly Cys His Gly Phe Arg Asp Pro Phe
             35                  40                  45

Lys Cys Asn Met Cys Gly Glu Lys Cys Asp Gly Pro Val Gly Leu Phe
         50                  55                  60

Val His Met Ala Arg Asn Ala His Ser Gly Val Pro
 65                  70                  75

<210> SEQ ID NO 183
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Met Ala Pro Lys Lys Arg Lys Val Gly Ile His Gly Val Leu Arg
 1               5                  10                  15

Gly Ala Ala His His Cys Gln His Cys Asp Met Tyr Phe Ala Asp Asn
                 20                  25                  30

Ile Leu Tyr Thr Ile His Met Gly Cys His Ser Cys Asp Asp Val Phe
             35                  40                  45
```

```
Lys Cys Asn Met Cys Gly Glu Lys Cys Asp Gly Pro Val Gly Leu Phe
    50                  55                  60

Val His Met Ala Arg Asn Ala His Gly Glu Lys Pro Thr Lys Cys Val
65                  70                  75                  80

His Cys Gly Ile Val Phe Leu Asp Glu Val Met Tyr Ala Leu His Met
                85                  90                  95

Ser Cys His Gly Phe Arg Asp Pro Phe Glu Cys Asn Ile Cys Gly Tyr
            100                 105                 110

His Ser Gln Asp Arg Tyr Glu Phe Ser Ser His Ile Val Arg Gly Glu
        115                 120                 125

His Ser Gly Val Pro
        130

<210> SEQ ID NO 184
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Met Ala Pro Lys Lys Arg Lys Val Gly Ile His Gly Val Leu Arg
1               5                   10                  15

Gly Ala Ala Gly Gly Ala Gln Leu Glu Lys Glu Leu Gln Ala Leu Glu
            20                  25                  30

Lys Lys Leu Ala Gln Leu Glu Trp Glu Asn Gln Ala Leu Glu Lys Glu
        35                  40                  45

Leu Ala Gln Gly Gly Ser Gly Val Pro
    50                  55

<210> SEQ ID NO 185
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Met Ala Pro Lys Lys Arg Lys Val Gly Ile His Gly Val Leu Arg
1               5                   10                  15

Gly Ala Ala Gly Gly Glu Gln Leu Glu Lys Lys Leu Gln Ala Leu Glu
            20                  25                  30

Lys Lys Leu Ala Gln Leu Glu Trp Lys Asn Gln Ala Leu Glu Lys Lys
        35                  40                  45

Leu Ala Gln Gly Gly Ser Gly Val Pro
    50                  55

<210> SEQ ID NO 186
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Met Ala Pro Lys Lys Arg Lys Val Gly Ile His Gly Val Leu Arg
1               5                   10                  15
```

-continued

Gly Ala Ala Gly Gly Glu Gln Leu Glu Lys Lys Leu Gln Ala Leu Glu
            20                  25                  30

Lys Lys Leu Ala Gln Leu Glu Trp Lys Asn Gln Ala Leu Glu Lys Gly
        35                  40                  45

Gly Ser Gly Val Pro
    50

<210> SEQ ID NO 187
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Met Ala Pro Lys Lys Lys Arg Lys Val Gly Ile His Gly Val Leu Arg
1               5                   10                  15

Gly Ala Ala Gly Gly Glu Gln Leu Glu Lys Lys Leu Gln Ala Leu Glu
            20                  25                  30

Lys Lys Leu Ala Gln Leu Glu Trp Lys Asn Gln Ala Gly Gly Ser Gly
        35                  40                  45

Val Pro
    50

<210> SEQ ID NO 188
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Met Ala Pro Lys Lys Lys Arg Lys Val Gly Ile His Gly Val Leu Ala
1               5                   10                  15

Ala Gly Gly Glu Gln Leu Glu Lys Lys Leu Gln Ala Leu Glu Lys Lys
            20                  25                  30

Leu Ala Gln Leu Glu Trp Lys Asn Gln Ala Leu Glu Lys Lys Leu Ala
        35                  40                  45

Gln Gly Val Pro
    50

<210> SEQ ID NO 189
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Met Ala Pro Lys Lys Lys Arg Lys Val Gly Ile His Gly Val Leu Ala
1               5                   10                  15

Ala Gly Gly Glu Gln Leu Glu Lys Lys Leu Gln Ala Leu Glu Lys Lys
            20                  25                  30

Leu Ala Gln Leu Glu Trp Lys Asn Gln Ala Leu Glu Lys Lys Leu Ala
        35                  40                  45

Gln Gly Gly Ser Gly Val Pro
    50                  55

```
<210> SEQ ID NO 190
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Met Ala Pro Lys Lys Arg Lys Val Gly Ile His Gly Val Leu Ala
1               5                   10                  15

Ala Gly Gly Glu Gln Leu Glu Lys Lys Leu Gln Ala Leu Glu Lys Lys
                20                  25                  30

Leu Ala Gln Leu Glu Trp Lys Asn Gln Ala Leu Glu Lys Lys Leu Ala
            35                  40                  45

Gln Gly Val Pro
    50

<210> SEQ ID NO 191
<211> LENGTH: 240
<212> TYPE: DNA
<213> ORGANISM: Mus sp.

<400> SEQUENCE: 191
tctgtcccat cgggcaggaa gccgtcatgg caaccctgga aaagctgatg aaggctttcg      60
agtcgctcaa gtcgtttcag cagcaacagc agcagcagcc accgccgcag cgccgccgc     120 caccgccgcc gccgcctccg cctcaacccc ctcagccgcc gcctcagggg cagccgccgc     180
cgccaccacc gccgctgcca ggtccggcag aggaaccgct gcaccgaccg tgagtccggg     240

<210> SEQ ID NO 192
<211> LENGTH: 300
<212> TYPE: DNA
<213> ORGANISM: Homo sapiens

<400> SEQUENCE: 192
actgccgtgc cgggcgggag accgccatgg cgaccctgga aaagctgatg aaggccttcg      60
agtccctcaa gtccttccag cagcagcagc agcagcagca gcagcagcag cagcagcagc     120
agcagcagca gcagcaacag ccgccaccgc cgccgccgcc gccgccgcct cctcagcttc     180
ctcagccgcc gccgcaggca cagccgctgc tgcctcagcc gcagccgccc cgccgccgc     240 ccccgccgcc acccggcccg gctgtggctg aggagccgct gcaccgaccg tgagtttggg     300

<210> SEQ ID NO 193
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
caggtccggc agaggaacc                                                    19

<210> SEQ ID NO 194
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
```

```
ttcacacggt ctttcttggt gg                                              22
```

<210> SEQ ID NO 195
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195

```
gcccggctgt ggctga                                                     16
```

<210> SEQ ID NO 196
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196

```
ttcacacggt ctttcttggt gg                                              22
```

<210> SEQ ID NO 197
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Ile His Gly Val Pro Met Val Asp Leu Arg Thr Leu Gly Tyr Ser
        35                  40                  45

Gln Gln Gln Gln Glu Lys Ile Lys Pro Lys Val Arg Ser Thr Val Ala
    50                  55                  60

Gln His His Glu Ala Leu Val Gly His Gly Phe Thr His Ala His Ile
65                  70                  75                  80

Val Ala Leu Ser Gln His Pro Ala Ala Leu Gly Thr Val Ala Val Lys
                85                  90                  95

Tyr Gln Asp Met Ile Ala Ala Leu Pro Glu Ala Thr His Glu Ala Ile
            100                 105                 110

Val Gly Val Gly Lys Gln Trp Ser Gly Ala Arg Ala Leu Glu Ala Leu
        115                 120                 125

Leu Thr Val Ala Gly Glu Leu Arg Gly Pro Pro Leu Gln Leu Asp Thr
    130                 135                 140

Gly Gln Leu Leu Lys Ile Ala Lys Arg Gly Gly Val Thr Ala Val Glu
145                 150                 155                 160

Ala Val His Ala Trp Arg Asn Ala Leu Thr Gly Ala Pro Leu Asn
                165                 170                 175

<210> SEQ ID NO 198
<211> LENGTH: 175
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 198

Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Lys Arg Lys Val
            20                  25                  30

Gly Ile His Gly Val Pro Met Val Asp Leu Arg Thr Leu Gly Tyr Ser
            35                  40                  45

Gln Gln Gln Gln Glu Lys Ile Lys Pro Lys Val Arg Ser Thr Val Ala
        50                  55                  60

Gln His His Glu Ala Leu Val Gly His Gly Phe Thr His Ala His Ile
65              70                  75                  80

Val Ala Leu Ser Gln His Pro Ala Ala Leu Gly Thr Val Ala Val Lys
                85                  90                  95

Tyr Gln Asp Met Ile Ala Ala Leu Pro Glu Ala Thr His Glu Ala Ile
            100                 105                 110

Val Gly Val Gly Lys Gln Trp Ser Gly Ala Arg Ala Leu Glu Ala Leu
        115                 120                 125

Leu Thr Val Ala Gly Glu Leu Arg Gly Pro Pro Leu Gln Leu Asp Thr
130             135                 140

Gly Gln Leu Leu Lys Ile Ala Lys Arg Gly Gly Val Thr Ala Val Glu
145                 150                 155                 160

Ala Val His Ala Trp Arg Asn Ala Leu Thr Gly Ala Pro Leu Asn
                165                 170                 175

<210> SEQ ID NO 199
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Lys Arg Lys Val
            20                  25                  30

Gly Ile His Gly Val Pro Met Val Asp Leu Arg Thr Leu Gly Tyr Ser
            35                  40                  45

Gln Gln Gln Gln Glu Lys Ile Lys Pro Lys Val Arg Ser Thr Val Ala
        50                  55                  60

Gln His His Glu Ala Leu Val Gly His Gly Phe Thr His Ala His Ile
65              70                  75                  80

Val Ala Leu Ser Gln His Pro Ala Ala Leu Gly Thr Val Ala Val Lys
                85                  90                  95

Tyr Gln Asp Met Ile Ala Ala Leu Pro Glu Ala Thr His Glu Ala Ile
            100                 105                 110

Val Gly Val Gly Lys Gln Trp Ser Gly Ala Arg Ala Leu Glu Ala Leu
        115                 120                 125

Leu Thr Val Ala Gly Glu Leu Arg Gly Pro Pro Leu Gln Leu Asp Thr
130             135                 140

Gly Gln Leu Leu Lys Ile Ala Lys Arg Gly Gly Val Thr Ala Val Glu
145                 150                 155                 160

```
Ala Val His Ala Trp Arg Asn Ala Leu Thr Gly Ala Pro Leu Asn
        165                 170                 175
```

<210> SEQ ID NO 200
<211> LENGTH: 21
<212> TYPE: DNA
<213> ORGANISM: Unknown
<220> FEATURE:
<223> OTHER INFORMATION: Description of Unknown: Target sequence

<400> SEQUENCE: 200
gcagcagcag cagcagcagc a                                          21

<210> SEQ ID NO 201
<211> LENGTH: 18
<212> TYPE: DNA
<213> ORGANISM: Unknown
<220> FEATURE:
<223> OTHER INFORMATION: Description of Unknown: Target sequence

<400> SEQUENCE: 201
gcagcagcag cagcagca                                              18

<210> SEQ ID NO 202
<211> LENGTH: 15
<212> TYPE: DNA
<213> ORGANISM: Unknown
<220> FEATURE:
<223> OTHER INFORMATION: Description of Unknown: Target sequence

<400> SEQUENCE: 202
gcagcagcag cagca                                                 15

<210> SEQ ID NO 203
<211> LENGTH: 12
<212> TYPE: DNA
<213> ORGANISM: Unknown
<220> FEATURE:
<223> OTHER INFORMATION: Description of Unknown: Target sequence

<400> SEQUENCE: 203
gcagcagcag ca                                                    12

<210> SEQ ID NO 204
<211> LENGTH: 21
<212> TYPE: DNA
<213> ORGANISM: Unknown
<220> FEATURE:
<223> OTHER INFORMATION: Description of Unknown: Target sequence

<400> SEQUENCE: 204
ctgctgctgc tgctgctgct g                                          21

<210> SEQ ID NO 205
<211> LENGTH: 18
<212> TYPE: DNA
<213> ORGANISM: Unknown
<220> FEATURE:
<223> OTHER INFORMATION: Description of Unknown: Target sequence

<400> SEQUENCE: 205
ctgctgctgc tgctgctg                                              18

<210> SEQ ID NO 206
<211> LENGTH: 15
<212> TYPE: DNA

```
<213> ORGANISM: Unknown
<220> FEATURE:
<223> OTHER INFORMATION: Description of Unknown: Target sequence

<400> SEQUENCE: 206
ctgctgctgc tgctg                                                          15

<210> SEQ ID NO 207
<211> LENGTH: 12
<212> TYPE: DNA
<213> ORGANISM: Unknown
<220> FEATURE:
<223> OTHER INFORMATION: Description of Unknown: Target sequence

<400> SEQUENCE: 207
ctgctgctgc tg                                                             12

<210> SEQ ID NO 208
<211> LENGTH: 29
<212> TYPE: DNA
<213> ORGANISM: Unknown
<220> FEATURE:
<223> OTHER INFORMATION: Description of Unknown: Human or mouse
      target sequence

<400> SEQUENCE: 208
ctgctgctgc tgctgctgct gctggaagg                                           29

<210> SEQ ID NO 209
<211> LENGTH: 28
<212> TYPE: DNA
<213> ORGANISM: Unknown
<220> FEATURE:
<223> OTHER INFORMATION: Description of Unknown: Human or mouse
      target sequence

<400> SEQUENCE: 209
gcggcgagtg cgtcccgtga cgtcatgc                                            28

<210> SEQ ID NO 210
<211> LENGTH: 170
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Gly Gly Arg Pro Ala Leu Glu Ser Ile Val Ala Gln Leu Ser Arg Pro
1               5                   10                  15

Asp Pro Ala Leu Ala Ala Leu Thr Asn Asp His Leu Val Ala Leu Ala
            20                  25                  30

Cys Leu Gly Gly Arg Pro Ala Leu Asp Ala Val Lys Lys Gly Leu Pro
        35                  40                  45

His Ala Pro Ala Leu Ile Lys Arg Thr Asn Arg Arg Ile Pro Glu Arg
    50                  55                  60

Thr Ser His Arg Val Ala Gly Ser Gly Met Asp Ala Lys Ser Leu Thr
65                  70                  75                  80

Ala Trp Ser Arg Thr Leu Val Thr Phe Lys Asp Val Phe Val Asp Phe
                85                  90                  95

Thr Arg Glu Glu Trp Lys Leu Leu Asp Thr Ala Gln Gln Ile Val Tyr
            100                 105                 110

Arg Asn Val Met Leu Glu Asn Tyr Lys Asn Leu Val Ser Leu Gly Tyr
```

```
                115                 120                 125
Gln Leu Thr Lys Pro Asp Val Ile Leu Arg Leu Glu Lys Gly Glu Glu
        130                 135                 140
Pro Trp Leu Val Glu Arg Glu Ile His Gln Glu Thr His Pro Asp Ser
145                 150                 155                 160
Glu Thr Ala Phe Glu Ile Lys Ser Ser Val
                165                 170
```

<210> SEQ ID NO 211
<211> LENGTH: 338
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 211

```
Gly Gly Arg Pro Ala Leu Glu Ser Ile Val Ala Gln Leu Ser Arg Pro
1               5                   10                  15
Asp Pro Ala Leu Ala Ala Leu Thr Asn Asp His Leu Val Ala Leu Ala
                20                  25                  30
Cys Leu Gly Gly Arg Pro Ala Leu Asp Ala Val Lys Lys Gly Leu Pro
            35                  40                  45
His Ala Pro Ala Leu Ile Lys Arg Thr Asn Arg Ile Pro Glu Arg
    50                  55                  60
Thr Ser His Arg Val Ala Asp His Ala Gln Val Val Arg Val Leu Gly
65                  70                  75                  80
Phe Phe Gln Cys His Ser His Pro Ala Gln Ala Phe Asp Asp Ala Met
                85                  90                  95
Thr Gln Phe Gly Met Ser Arg His Gly Leu Leu Gln Leu Phe Arg Arg
                100                 105                 110
Val Gly Val Thr Glu Leu Glu Ala Arg Ser Gly Thr Leu Pro Pro Ala
            115                 120                 125
Ser Gln Arg Trp Asp Arg Ile Leu Gln Ala Ser Gly Met Lys Arg Ala
        130                 135                 140
Lys Pro Ser Pro Thr Ser Thr Gln Thr Pro Asp Gln Ala Ser Leu His
145                 150                 155                 160
Ala Phe Ala Asp Ser Leu Glu Arg Asp Leu Asp Ala Pro Ser Pro Thr
                165                 170                 175
His Glu Gly Asp Gln Arg Arg Ala Ser Ser Arg Lys Arg Ser Arg Ser
                180                 185                 190
Asp Arg Ala Val Thr Gly Pro Ser Ala Gln Ser Phe Glu Val Arg
        195                 200                 205
Ala Pro Glu Gln Arg Asp Ala Leu His Leu Pro Leu Ser Trp Arg Val
    210                 215                 220
Lys Arg Pro Arg Thr Ser Ile Gly Gly Leu Pro Asp Pro Gly Ser
225                 230                 235                 240
Gly Met Asp Ala Lys Ser Leu Thr Ala Trp Ser Arg Thr Leu Val Thr
                245                 250                 255
Phe Lys Asp Val Phe Val Asp Phe Thr Arg Glu Glu Trp Lys Leu Leu
                260                 265                 270
Asp Thr Ala Gln Gln Ile Val Tyr Arg Asn Val Met Leu Glu Asn Tyr
        275                 280                 285
Lys Asn Leu Val Ser Leu Gly Tyr Gln Leu Thr Lys Pro Asp Val Ile
    290                 295                 300
```

Leu Arg Leu Glu Lys Gly Glu Glu Pro Trp Leu Val Glu Arg Glu Ile
305                 310                 315                 320

His Gln Glu Thr His Pro Asp Ser Glu Thr Ala Phe Glu Ile Lys Ser
            325                 330                 335

Ser Val

<210> SEQ ID NO 212
<211> LENGTH: 384
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Gly Gly Arg Pro Ala Leu Glu Ser Ile Val Ala Gln Leu Ser Arg Pro
1               5                   10                  15

Asp Pro Ala Leu Ala Ala Leu Thr Asn Asp His Leu Val Ala Leu Ala
            20                  25                  30

Cys Leu Gly Gly Arg Pro Ala Leu Asp Ala Val Lys Lys Gly Leu Pro
        35                  40                  45

His Ala Pro Ala Leu Ile Lys Arg Thr Asn Arg Arg Ile Pro Glu Arg
50                  55                  60

Thr Ser His Arg Val Ala Asp His Ala Gln Val Val Arg Val Leu Gly
65                  70                  75                  80

Phe Phe Gln Cys His Ser His Pro Ala Gln Ala Phe Asp Asp Ala Met
                85                  90                  95

Thr Gln Phe Gly Met Ser Arg His Gly Leu Leu Gln Leu Phe Arg Arg
            100                 105                 110

Val Gly Val Thr Glu Leu Glu Ala Arg Ser Gly Thr Leu Pro Pro Ala
        115                 120                 125

Ser Gln Arg Trp Asp Arg Ile Leu Gln Ala Ser Gly Met Lys Arg Ala
130                 135                 140

Lys Pro Ser Pro Thr Ser Thr Gln Thr Pro Asp Gln Ala Ser Leu His
145                 150                 155                 160

Ala Phe Ala Asp Ser Leu Glu Arg Asp Leu Asp Ala Pro Ser Pro Thr
                165                 170                 175

His Glu Gly Asp Gln Arg Arg Ala Ser Ser Arg Lys Arg Ser Arg Ser
            180                 185                 190

Asp Arg Ala Val Thr Gly Pro Ser Ala Gln Gln Ser Phe Glu Val Arg
        195                 200                 205

Ala Pro Glu Gln Arg Asp Ala Leu His Leu Pro Leu Ser Trp Arg Val
210                 215                 220

Lys Arg Pro Arg Thr Ser Ile Gly Gly Gly Leu Pro Asp Pro Thr Pro
225                 230                 235                 240

Thr Ala Ala Asp Leu Ala Ala Ser Ser Thr Val Met Arg Glu Gln Asp
                245                 250                 255

Glu Asp Pro Phe Ala Gly Ala Ala Asp Phe Pro Ala Phe Asn Glu
            260                 265                 270

Glu Glu Leu Ala Trp Leu Met Glu Leu Leu Pro Gln Gly Ser Gly Met
        275                 280                 285

Asp Ala Lys Ser Leu Thr Ala Trp Ser Arg Thr Leu Val Thr Phe Lys
290                 295                 300

Asp Val Phe Val Asp Phe Thr Arg Glu Glu Trp Lys Leu Leu Asp Thr
305                 310                 315                 320

```
Ala Gln Gln Ile Val Tyr Arg Asn Val Met Leu Glu Asn Tyr Lys Asn
            325                 330                 335

Leu Val Ser Leu Gly Tyr Gln Leu Thr Lys Pro Asp Val Ile Leu Arg
        340                 345                 350

Leu Glu Lys Gly Glu Pro Trp Leu Val Glu Arg Glu Ile His Gln
        355                 360                 365

Glu Thr His Pro Asp Ser Glu Thr Ala Phe Glu Ile Lys Ser Ser Val
        370                 375                 380

<210> SEQ ID NO 213
<211> LENGTH: 174
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Gly Ser Gly Gly Thr Lys Cys Val His Cys Gly Ile Val Phe Leu Asp
1               5                   10                  15

Glu Val Met Tyr Ala Leu His Met Ser Cys His Gly Phe Arg Asp Pro
            20                  25                  30

Phe Glu Cys Asn Ile Cys Gly Tyr His Ser Gln Asp Arg Tyr Glu Phe
        35                  40                  45

Ser Ser His Ile Val Arg Gly Glu His Leu Arg Gln Lys Asp Ala Ala
    50                  55                  60

Arg Ser Arg Ser Gly Met Asp Ala Lys Ser Leu Thr Ala Trp Ser Arg
65                  70                  75                  80

Thr Leu Val Thr Phe Lys Asp Val Phe Val Asp Phe Thr Arg Glu Glu
                85                  90                  95

Trp Lys Leu Leu Asp Thr Ala Gln Gln Ile Val Tyr Arg Asn Val Met
            100                 105                 110

Leu Glu Asn Tyr Lys Asn Leu Val Ser Leu Gly Tyr Gln Leu Thr Lys
        115                 120                 125

Pro Asp Val Ile Leu Arg Leu Glu Lys Gly Glu Pro Trp Leu Val
    130                 135                 140

Glu Arg Glu Ile His Gln Glu Thr His Pro Asp Ser Glu Thr Ala Phe
145                 150                 155                 160

Glu Ile Lys Ser Ser Val Asp Tyr Lys Asp Asp Asp Lys
                165                 170

<210> SEQ ID NO 214
<211> LENGTH: 174
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Gly Ser Gly Gly Thr Lys Cys Val His Cys Gly Ile Val Phe Leu Asp
1               5                   10                  15

Glu Val Met Tyr Ala Leu His Met Ser Cys His Gly Phe Arg Asp Pro
            20                  25                  30

Phe Glu Cys Asn Ile Cys Gly Tyr His Ser Gln Asp Arg Tyr Glu Phe
        35                  40                  45

Ser Ser His Ile Val Arg Gly Glu His Leu Arg Gln Lys Asp Ala Ala
    50                  55                  60
```

```
Arg Ser Arg Ser Gly Met Asp Ala Lys Ser Leu Thr Ala Trp Ser Arg
 65                  70                  75                  80

Thr Leu Val Thr Phe Lys Asp Val Phe Val Asp Phe Thr Arg Glu Glu
                 85                  90                  95

Trp Lys Leu Leu Asp Thr Ala Gln Gln Ile Val Tyr Arg Asn Val Met
            100                 105                 110

Leu Glu Asn Tyr Lys Asn Leu Val Ser Leu Gly Tyr Gln Leu Thr Lys
        115                 120                 125

Pro Asp Val Ile Leu Arg Leu Glu Lys Gly Glu Pro Trp Leu Val
    130                 135                 140

Glu Arg Glu Ile His Gln Glu Thr His Pro Asp Ser Glu Thr Ala Phe
145                 150                 155                 160

Glu Ile Lys Ser Ser Val Asp Tyr Lys Asp Asp Asp Lys
                165                 170

<210> SEQ ID NO 215
<211> LENGTH: 174
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

Gly Ser Gly Gly His His Cys Gln His Cys Asp Met Tyr Phe Ala Asp
 1               5                  10                  15

Asn Ile Leu Tyr Thr Ile His Met Gly Cys His Gly Tyr Glu Asn Pro
             20                  25                  30

Phe Glu Cys Asn Ile Cys Gly Tyr His Ser Gln Asp Arg Tyr Glu Phe
             35                  40                  45

Ser Ser His Ile Val Arg Gly Glu His Leu Arg Gln Lys Asp Ala Ala
         50                  55                  60

Arg Ser Arg Ser Gly Met Asp Ala Lys Ser Leu Thr Ala Trp Ser Arg
 65                  70                  75                  80

Thr Leu Val Thr Phe Lys Asp Val Phe Val Asp Phe Thr Arg Glu Glu
                 85                  90                  95

Trp Lys Leu Leu Asp Thr Ala Gln Gln Ile Val Tyr Arg Asn Val Met
            100                 105                 110

Leu Glu Asn Tyr Lys Asn Leu Val Ser Leu Gly Tyr Gln Leu Thr Lys
        115                 120                 125

Pro Asp Val Ile Leu Arg Leu Glu Lys Gly Glu Pro Trp Leu Val
    130                 135                 140

Glu Arg Glu Ile His Gln Glu Thr His Pro Asp Ser Glu Thr Ala Phe
145                 150                 155                 160

Glu Ile Lys Ser Ser Val Asp Tyr Lys Asp Asp Asp Lys
                165                 170

<210> SEQ ID NO 216
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Gly Ser Gly Gly Phe Lys Cys Glu His Cys Arg Ile Leu Phe Leu Asp
 1               5                  10                  15
```

His Val Met Phe Thr Ile His Met Gly Cys His Gly Phe Arg Asp Pro
            20                  25                  30

Phe Lys Cys Asn Met Cys Gly Glu Lys Cys Asp Gly Pro Val Gly Leu
            35                  40                  45

Phe Val His Met Ala Arg Asn Ala His Gly Glu Lys Pro Phe Tyr Cys
    50                  55                  60

Glu His Cys Glu Ile Thr Phe Arg Asp Val Val Met Tyr Ser Leu His
65                  70                  75                  80

Lys Gly Tyr His Gly Phe Arg Asp Pro Phe Glu Cys Asn Ile Cys Gly
                85                  90                  95

Tyr His Ser Gln Asp Arg Tyr Glu Phe Ser Ser His Ile Val Arg Gly
            100                 105                 110

Glu His Leu Arg Gln Lys Asp Ala Ala Arg Ser Arg Ser Gly Met Asp
            115                 120                 125

Ala Lys Ser Leu Thr Ala Trp Ser Arg Thr Leu Val Thr Phe Lys Asp
        130                 135                 140

Val Phe Val Asp Phe Thr Arg Glu Glu Trp Lys Leu Leu Asp Thr Ala
145                 150                 155                 160

Gln Gln Ile Val Tyr Arg Asn Val Met Leu Glu Asn Tyr Lys Asn Leu
                165                 170                 175

Val Ser Leu Gly Tyr Gln Leu Thr Lys Pro Asp Val Ile Leu Arg Leu
            180                 185                 190

Glu Lys Gly Glu Glu Pro Trp Leu Val Glu Arg Glu Ile His Gln Glu
            195                 200                 205

Thr His Pro Asp Ser Glu Thr Ala Phe Glu Ile Lys Ser Ser Val Asp
        210                 215                 220

Tyr Lys Asp Asp Asp Asp Lys
225                 230

<210> SEQ ID NO 217
<211> LENGTH: 153
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Gly Ser Gly Gly Ala Gln Leu Lys Lys Lys Leu Gln Ala Asn Lys Lys
1               5                   10                  15

Glu Leu Ala Gln Leu Lys Trp Lys Leu Gln Ala Leu Lys Lys Lys Leu
            20                  25                  30

Ala Gln Gly Gly Leu Arg Gln Lys Asp Ala Ala Arg Ser Arg Ser Gly
        35                  40                  45

Met Asp Ala Lys Ser Leu Thr Ala Trp Ser Arg Thr Leu Val Thr Phe
    50                  55                  60

Lys Asp Val Phe Val Asp Phe Thr Arg Glu Glu Trp Lys Leu Leu Asp
65                  70                  75                  80

Thr Ala Gln Gln Ile Val Tyr Arg Asn Val Met Leu Glu Asn Tyr Lys
                85                  90                  95

Asn Leu Val Ser Leu Gly Tyr Gln Leu Thr Lys Pro Asp Val Ile Leu
            100                 105                 110

Arg Leu Glu Lys Gly Glu Glu Pro Trp Leu Val Glu Arg Glu Ile His
        115                 120                 125

Gln Glu Thr His Pro Asp Ser Glu Thr Ala Phe Glu Ile Lys Ser Ser
    130                 135                 140

```
Val Asp Tyr Lys Asp Asp Asp Lys
145                 150

<210> SEQ ID NO 218
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

Gly Ser Gly Gly Ala Leu Lys Lys Glu Leu Gln Ala Asn Lys Lys Glu
1               5                   10                  15

Leu Ala Gln Leu Lys Trp Glu Leu Gln Ala Leu Lys Lys Glu Leu Ala
                20                  25                  30

Gln Gly Gly Leu Arg Gln Lys Asp Ala Ala Arg Ser Arg Ser Gly Met
            35                  40                  45

Asp Ala Lys Ser Leu Thr Ala Trp Ser Arg Thr Leu Val Thr Phe Lys
50                  55                  60

Asp Val Phe Val Asp Phe Thr Arg Glu Glu Trp Lys Leu Leu Asp Thr
65                  70                  75                  80

Ala Gln Gln Ile Val Tyr Arg Asn Val Met Leu Glu Asn Tyr Lys Asn
                85                  90                  95

Leu Val Ser Leu Gly Tyr Gln Leu Thr Lys Pro Asp Val Ile Leu Arg
            100                 105                 110

Leu Glu Lys Gly Glu Glu Pro Trp Leu Val Glu Arg Glu Ile His Gln
        115                 120                 125

Glu Thr His Pro Asp Ser Glu Thr Ala Phe Glu Ile Lys Ser Ser Val
    130                 135                 140

Asp Tyr Lys Asp Asp Asp Asp Lys
145                 150

<210> SEQ ID NO 219
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Gly Ser Gly Gly Glu Leu Gln Ala Asn Lys Lys Glu Leu Ala Gln Leu
1               5                   10                  15

Lys Trp Glu Leu Gln Ala Leu Lys Lys Glu Leu Ala Gln Gly Gly Leu
                20                  25                  30

Arg Gln Lys Asp Ala Ala Arg Ser Arg Ser Gly Met Asp Ala Lys Ser
            35                  40                  45

Leu Thr Ala Trp Ser Arg Thr Leu Val Thr Phe Lys Asp Val Phe Val
        50                  55                  60

Asp Phe Thr Arg Glu Glu Trp Lys Leu Leu Asp Thr Ala Gln Gln Ile
65                  70                  75                  80

Val Tyr Arg Asn Val Met Leu Glu Asn Tyr Lys Asn Leu Val Ser Leu
                85                  90                  95

Gly Tyr Gln Leu Thr Lys Pro Asp Val Ile Leu Arg Leu Glu Lys Gly
            100                 105                 110

Glu Glu Pro Trp Leu Val Glu Arg Glu Ile His Gln Glu Thr His Pro
        115                 120                 125
```

```
Asp Ser Glu Thr Ala Phe Glu Ile Lys Ser Ser Val Asp Tyr Lys Asp
        130                 135                 140

Asp Asp Asp Lys
145

<210> SEQ ID NO 220
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Gly Ser Gly Gly Gln Ala Asn Lys Lys Glu Leu Ala Gln Leu Lys Trp
1               5                   10                  15

Glu Leu Gln Ala Leu Lys Lys Glu Leu Ala Gln Gly Gly Leu Arg Gln
            20                  25                  30

Lys Asp Ala Ala Arg Ser Arg Ser Gly Met Asp Ala Lys Ser Leu Thr
        35                  40                  45

Ala Trp Ser Arg Thr Leu Val Thr Phe Lys Asp Val Phe Val Asp Phe
    50                  55                  60

Thr Arg Glu Glu Trp Lys Leu Leu Asp Thr Ala Gln Gln Ile Val Tyr
65                  70                  75                  80

Arg Asn Val Met Leu Glu Asn Tyr Lys Asn Leu Val Ser Leu Gly Tyr
                85                  90                  95

Gln Leu Thr Lys Pro Asp Val Ile Leu Arg Leu Glu Lys Gly Glu Glu
            100                 105                 110

Pro Trp Leu Val Glu Arg Glu Ile His Gln Glu Thr His Pro Asp Ser
        115                 120                 125

Glu Thr Ala Phe Glu Ile Lys Ser Ser Val Asp Tyr Lys Asp Asp Asp
    130                 135                 140

Asp Lys
145

<210> SEQ ID NO 221
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Met Ala Pro Lys Lys Lys Arg Lys Val Gly Ile His Gly Val Leu Ala
1               5                   10                  15

Ala Gly Gly Glu Gln Leu Glu Lys Leu Gln Ala Leu Glu Lys Lys
            20                  25                  30

Leu Ala Gln Leu Glu Trp Lys Asn Gln Ala Leu Glu Lys Lys Leu Ala
        35                  40                  45

Gln Gly Gly Ser Gly Val Pro
    50                  55

<210> SEQ ID NO 222
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 222

Gly Ser Gly Gly Ala Leu Lys Lys Glu Leu Gln Ala Asn Lys Lys Glu
1               5                   10                  15

Leu Ala Gln Leu Lys Trp Glu Leu Gln Ala Leu Lys Lys Glu Leu Ala
            20                  25                  30

Gln Gly Ser Gly Met Asp Ala Lys Ser Leu Thr Ala Trp Ser Arg Thr
        35                  40                  45

Leu Val Thr Phe Lys Asp Val Phe Val Asp Phe Thr Arg Glu Glu Trp
50                  55                  60

Lys Leu Leu Asp Thr Ala Gln Gln Ile Val Tyr Arg Asn Val Met Leu
65                  70                  75                  80

Glu Asn Tyr Lys Asn Leu Val Ser Leu Gly Tyr Gln Leu Thr Lys Pro
                85                  90                  95

Asp Val Ile Leu Arg Leu Glu Lys Gly Glu Pro Trp Leu Val Glu
            100                 105                 110

Arg Glu Ile His Gln Glu Thr His Pro Asp Ser Glu Thr Ala Phe Glu
            115                 120                 125

Ile Lys Ser Ser Val Asp Tyr Lys Asp Asp Asp Lys
            130                 135                 140

<210> SEQ ID NO 223
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Gly Ser Gly Gly Ala Leu Lys Lys Glu Leu Gln Ala Asn Lys Lys Glu
1               5                   10                  15

Leu Ala Gln Leu Lys Trp Glu Leu Gln Ala Leu Lys Lys Glu Leu Ala
            20                  25                  30

Gln Gly Ser Gly Met Asp Ala Lys Ser Leu Thr Ala Trp Ser Arg Thr
        35                  40                  45

Leu Val Thr Phe Lys Asp Val Phe Val Asp Phe Thr Arg Glu Glu Trp
50                  55                  60

Lys Leu Leu Asp Thr Ala Gln Gln Ile Val Tyr Arg Asn Val Met Leu
65                  70                  75                  80

Glu Asn Tyr Lys Asn Leu Val Ser Leu Gly Tyr Gln Leu Thr Lys Pro
                85                  90                  95

Asp Val Ile Leu Arg Leu Glu Lys Gly Glu Pro Trp Leu Val Glu
            100                 105                 110

Arg Glu Ile His Gln Glu Thr His Pro Asp Ser Glu Thr Ala Phe Glu
            115                 120                 125

Ile Lys Ser Ser Val Asp Tyr Lys Asp Asp Asp Lys
            130                 135                 140

<210> SEQ ID NO 224
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

```
Gly Ser Ala Leu Lys Lys Glu Leu Gln Ala Asn Lys Lys Glu Leu Ala
1               5                   10                  15

Gln Leu Lys Trp Glu Leu Gln Ala Leu Lys Lys Glu Leu Ala Gln Gly
            20                  25                  30

Ser Gly Met Asp Ala Lys Ser Leu Thr Ala Trp Ser Arg Thr Leu Val
        35                  40                  45

Thr Phe Lys Asp Val Phe Val Asp Phe Thr Arg Glu Glu Trp Lys Leu
50                  55                  60

Leu Asp Thr Ala Gln Gln Ile Val Tyr Arg Asn Val Met Leu Glu Asn
65                  70                  75                  80

Tyr Lys Asn Leu Val Ser Leu Gly Tyr Gln Leu Thr Lys Pro Asp Val
                85                  90                  95

Ile Leu Arg Leu Glu Lys Gly Glu Glu Pro Trp Leu Val Glu Arg Glu
            100                 105                 110

Ile His Gln Glu Thr His Pro Asp Ser Glu Thr Ala Phe Glu Ile Lys
        115                 120                 125

Ser Ser Val Asp Tyr Lys Asp Asp Asp Lys
    130                 135
```

<210> SEQ ID NO 225
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

```
Gly Ser Ala Leu Lys Lys Glu Leu Gln Ala Asn Lys Lys Glu Leu Ala
1               5                   10                  15

Gln Leu Lys Trp Glu Leu Gln Ala Leu Lys Lys Glu Leu Ala Gln Gly
            20                  25                  30

Ser Gly Met Asp Ala Lys Ser Leu Thr Ala Trp Ser Arg Thr Leu Val
        35                  40                  45

Thr Phe Lys Asp Val Phe Val Asp Phe Thr Arg Glu Glu Trp Lys Leu
50                  55                  60

Leu Asp Thr Ala Gln Gln Ile Val Tyr Arg Asn Val Met Leu Glu Asn
65                  70                  75                  80

Tyr Lys Asn Leu Val Ser Leu Gly Tyr Gln Leu Thr Lys Pro Asp Val
                85                  90                  95

Ile Leu Arg Leu Glu Lys Gly Glu Glu Pro Trp Leu Val Glu Arg Glu
            100                 105                 110

Ile His Gln Glu Thr His Pro Asp Ser Glu Thr Ala Phe Glu Ile Lys
        115                 120                 125

Ser Ser Val Asp Tyr Lys Asp Asp Asp Lys
    130                 135
```

<210> SEQ ID NO 226
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(60)
<223> OTHER INFORMATION: This sequence may encompass 15-20 repeating
      "CAG" units

```
<400> SEQUENCE: 226
cagcagcagc agcagcagca gcagcagcag cagcagcagc agcagcagca gcagcagcag      60

<210> SEQ ID NO 227
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 227
cagcagcagc agcagcagca gcagcagcag cagcagcagc agcagcagca gcagcagcag      60
cagcagcagc agcagcagca gcagcagcag cagcagcagc agcag                     105

<210> SEQ ID NO 228
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(117)
<223> OTHER INFORMATION: This sequence may encompass 36-39 repeating
      "CAG" units

<400> SEQUENCE: 228
cagcagcagc agcagcagca gcagcagcag cagcagcagc agcagcagca gcagcagcag      60
cagcagcagc agcagcagca gcagcagcag cagcagcagc agcagcagca gcagcag        117

<210> SEQ ID NO 229
<211> LENGTH: 180
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 229
cagcagcagc agcagcagca gcagcagcag cagcagcagc agcagcagca gcagcagcag      60
cagcagcagc agcagcagca gcagcagcag cagcagcagc agcagcagca gcagcagcag     120
cagcagcagc agcagcagca gcagcagcag cagcagcagc agcagcagca gcagcagcag     180

<210> SEQ ID NO 230
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 230
cagcagcagc agcagcagca gcagcagcag cagcagcagc agcagcagca gcagcagcag      60
cagcagcagc agcagcagca gcagcagcag cagcagcagc agcagcagca gcagcagcag     120
cagcagcagc agcagcagca gcagcagcag                                      150

<210> SEQ ID NO 231
<211> LENGTH: 240
<212> TYPE: DNA
<213> ORGANISM: Artificial Sequence
<220> FEATURE:
```

<223> OTHER INFORMATION: Description of Artificial Sequence: Synthetic
      polynucleotide

<400> SEQUENCE: 231
cagcagcagc agcagcagca gcagcagcag cagcagcagc agcagcagca gcagcagcag    60
cagcagcagc agcagcagca gcagcagcag cagcagcagc agcagcagca gcagcagcag   120
cagcagcagc agcagcagca gcagcagcag cagcagcagc agcagcagca gcagcagcag   180
cagcagcagc agcagcagca gcagcagcag cagcagcagc agcagcagca gcagcagcag   240

<210> SEQ ID NO 232
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 232
cagcagcagc agcagcagca gcagcagcag cagcagcagc agcagcagca gcagcagcag    60
cagcagcagc agcagcagca gcagcagcag cagcagcagc agcagcagca gcagcagcag   120
cagcagcagc agcagcagca gcagcagcag cagcagcagc agcagcagca gcagcagcag   180
cagcagcagc agcagcagca gcagcagcag cagcagcagc agcagcagca gcagcagcag   240
cagcagcagc agcagcagca gcagcagcag cagcagcagc agcagcagca gcagcagcag   300
cagcagcagc agcagcagca gcagcag                                       327

<210> SEQ ID NO 233
<211> LENGTH: 540
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 233
cagcagcagc agcagcagca gcagcagcag cagcagcagc agcagcagca gcagcagcag    60
cagcagcagc agcagcagca gcagcagcag cagcagcagc agcagcagca gcagcagcag   120
cagcagcagc agcagcagca gcagcagcag cagcagcagc agcagcagca gcagcagcag   180
cagcagcagc agcagcagca gcagcagcag cagcagcagc agcagcagca gcagcagcag   240
cagcagcagc agcagcagca gcagcagcag cagcagcagc agcagcagca gcagcagcag   300
cagcagcagc agcagcagca gcagcagcag cagcagcagc agcagcagca gcagcagcag   360
cagcagcagc agcagcagca gcagcagcag cagcagcagc agcagcagca gcagcagcag   420
cagcagcagc agcagcagca gcagcagcag cagcagcagc agcagcagca gcagcagcag   480
cagcagcagc agcagcagca gcagcagcag cagcagcagc agcagcagca gcagcagcag   540

<210> SEQ ID NO 234
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
cagcagcagc agcagcagca gcagcagcag                                     30

```
<210> SEQ ID NO 235
<211> LENGTH: 141
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 235
cagcagcagc agcagcagca gcagcagcag cagcagcagc agcagcagca gcagcagcag     60
cagcagcagc agcagcagca gcagcagcag cagcagcagc agcagcagca gcagcagcag    120
cagcagcagc agcagcagca g                                              141

<210> SEQ ID NO 236
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
cagcagcagc agcagcagca gcagcagcag cagcagcagc agcagcagca g              51

<210> SEQ ID NO 237
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
cagcagcagc agcagcagca gcagcagcag cagcagcagc agcagcagca gcagcagcag     60
cagcagcag                                                             69

<210> SEQ ID NO 238
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 238
cagcagcagc agcagcagca gcagcagcag cagcagcagc agcagcagca gcagcagcag     60
cagcagcagc agcagcagca gcagcagcag cagcagcagc agcagcagca gcagcagcag    120
cagcagcagc agcagcagca gcagcagcag cagcagcagc agcagcagca gcagcagcag    180
cagcagcagc agcagcagca gcagcagcag cagcagcagc agcagcagca gcagcagcag    240
cagcagcagc agcagcagca gcagcagcag cagcagcagc agcagcagca gcagcagcag    300
cagcagcagc agcagcagca gcagcagcag cag                                 333

<210> SEQ ID NO 239
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
cagcagcagc agcagcagca gcagcagcag cagcagcagc agcag                     45
```

-continued

<210> SEQ ID NO 240
<211> LENGTH: 210
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 240
cagcagcagc agcagcagca gcagcagcag cagcagcagc agcagcagca gcagcagcag    60
cagcagcagc agcagcagca gcagcagcag cagcagcagc agcagcagca gcagcagcag   120
cagcagcagc agcagcagca gcagcagcag cagcagcagc agcagcagca gcagcagcag   180
cagcagcagc agcagcagca gcagcagcag                                    210

<210> SEQ ID NO 241
<211> LENGTH: 300
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 241
cagcagcagc agcagcagca gcagcagcag cagcagcagc agcagcagca gcagcagcag    60
cagcagcagc agcagcagca gcagcagcag cagcagcagc agcagcagca gcagcagcag   120
cagcagcagc agcagcagca gcagcagcag cagcagcagc agcagcagca gcagcagcag   180
cagcagcagc agcagcagca gcagcagcag cagcagcagc agcagcagca gcagcagcag   240
cagcagcagc agcagcagca gcagcagcag cagcagcagc agcagcagca gcagcagcag   300

<210> SEQ ID NO 242
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 242
cagcagcagc agcagcagca gcagcagcag cagcagcagc agcagcagca gcagcagcag    60
cagcagcagc agcagcagca gcagcagcag cagcagcagc agcagcagca gcagcagcag   120
cagcagcagc agcagcagca gcagcagcag cagcagcagc agcagcagca gcagcagcag   180
cagcagcagc agcagcagca g                                             201

<210> SEQ ID NO 243
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 243
cagcagcagc agcagcagca gcagcagcag cagcagcagc agcagcagca gcagcagcag    60
cagcagcagc agcagcagca gcagcagcag cagcagcagc agcagcagca gcagcagcag   120
cagcagcagc agcag                                                    135

<210> SEQ ID NO 244

```
<211> LENGTH: 132
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 244
cagcagcagc agcagcagca gcagcagcag cagcagcagc agcagcagca gcagcagcag      60
cagcagcagc agcagcagca gcagcagcag cagcagcagc agcagcagca gcagcagcag     120
cagcagcagc ag                                                         132

<210> SEQ ID NO 245
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
cagcagcagc agcagcagca gcagcagcag cagcagcagc agcagcagca gcag            54

<210> SEQ ID NO 246
<211> LENGTH: 207
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 246
cagcagcagc agcagcagca gcagcagcag cagcagcagc agcagcagca gcagcagcag      60
cagcagcagc agcagcagca gcagcagcag cagcagcagc agcagcagca gcagcagcag     120
cagcagcagc agcagcagca gcagcagcag cagcagcagc agcagcagca gcagcagcag     180
cagcagcagc agcagcagca gcagcag                                         207

<210> SEQ ID NO 247
<211> LENGTH: 144
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 247
cagcagcagc agcagcagca gcagcagcag cagcagcagc agcagcagca gcagcagcag      60
cagcagcagc agcagcagca gcagcagcag cagcagcagc agcagcagca gcagcagcag     120
cagcagcagc agcagcagca gcag                                            144

<210> SEQ ID NO 248
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
cagcagcagc agcagcagca gcagcagcag cagcagcagc agcagcagca gcagcagcag      60

<210> SEQ ID NO 249
```

```
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 249
cagcagcagc agcagcagca gcagcagcag cagcagcagc agcagcagca gcagcagcag      60
cagcagcagc agcagcagca gcagcagcag cagcagcagc agcagcagca gcagcagcag     120
cag                                                                   123

<210> SEQ ID NO 250
<211> LENGTH: 9
<212> TYPE: PRT
<213> ORGANISM: Unknown
<220> FEATURE:
<223> OTHER INFORMATION: Description of Unknown: Unknown family peptide

<400> SEQUENCE: 250

Leu Ala Gly Leu Ile Asp Ala Asp Gly
1               5

<210> SEQ ID NO 251
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
cagcagcagc agcagcagca gcagcagcag cagcagcagc agcagcag                   48

<210> SEQ ID NO 252
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 252
cagcagcagc agcagcagca gcagcagcag cagcagcagc agcagcagca gcagcagcag      60
cagcagcagc agcagcagca gcagcagcag cagcagcagc agcagcagca gcagcagcag     120
cagcagcagc agcagcagca gcagcagcag cagcagcagc agcagcagca gcagcagcag     180
cagcagcagc agcagcagca gcagcagcag cagcagcagc agcagcagca gcagcagcag     240
cagcagcagc agcagcagca gcagcagcag cagcagcagc agcagcagca gcagcagcag     300
cagcagcagc agcagcagca gcagcagcag cagcagcagc agcagcagca gcagcagcag     360

<210> SEQ ID NO 253
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
cagcagcagc agcagcagca gcagcagcag cagcagcagc agcagcagca gcagcagcag      60
cagcagcagc agcag                                                       75
```

```
<210> SEQ ID NO 254
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 254
cagcagcagc agcagcagca gcagcagcag cagcagcagc agcagcagca gcagcagcag        60
cagcagcagc agcagcagca gcagcagcag cagcagcagc agcagcag                    108

<210> SEQ ID NO 255
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 255
cagcagcagc agcagcagca gcagcagcag cagcagcagc agcagcagca gcagcagcag        60
cagcagcagc agcagcagca gcagcagcag cagcagcagc agcagcagca gcagcag          117

<210> SEQ ID NO 256
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
cagcagcagc agcagcagca gcagcagcag cagcagcagc agcagcagca gcagcagcag        60
cagcagcagc ag                                                            72

<210> SEQ ID NO 257
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 257
cagcagcagc agcagcagca gcagcagcag cagcagcagc agcagcagca gcagcagcag        60
cagcagcagc agcagcagca gcagcagcag cagcagcagc agcagcagca gcagcagcag       120
cagcag                                                                  126

<210> SEQ ID NO 258
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
cagcagcagc agcagcagca gcagcagcag cagcagcagc agcagcagca gcagcagcag        60
cagcagcagc agcagcagca gcagcag                                            87

<210> SEQ ID NO 259
```

```
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 259
cagcagcagc agcagcagca gcagcagcag cagcagcagc agcagcagca gcagcagcag      60
cagcagcagc agcagcagca gcagcagcag cagcagcagc agcagcagca gcagcagcag     120

<210> SEQ ID NO 260
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
gcagcagcag cagcagcagc                                                  20

<210> SEQ ID NO 261
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
cagcagcagc agcagcagca g                                                21
```